United States Patent
Baas et al.

(10) Patent No.: US 9,089,555 B2
(45) Date of Patent: Jul. 28, 2015

(54) COMPLEMENT ANTAGONISTS AND USES THEREOF

(71) Applicant: Regenesance B.V., Amsterdam (NL)

(72) Inventors: Frank Baas, Hilversum (NL); Kees Fluiter, Amsterdam (NL)

(73) Assignee: Regenesance B.V., Amsterdam (NL)

( * ) Notice: Subject to any disclaimer, the term of this patent is extended or adjusted under 35 U.S.C. 154(b) by 233 days.

(21) Appl. No.: 14/206,022

(22) Filed: Mar. 12, 2014

(65) Prior Publication Data

US 2014/0301982 A1    Oct. 9, 2014

Related U.S. Application Data

(62) Division of application No. 13/003,062, filed as application No. PCT/NL2009/050418 on Jul. 10, 2009, now Pat. No. 8,703,730.

(60) Provisional application No. 61/079,051, filed on Jul. 8, 2008.

(51) Int. Cl.

| | |
|---|---|
| *A61K 31/70* | (2006.01) |
| *C07H 21/02* | (2006.01) |
| *C07H 21/04* | (2006.01) |
| *A61K 39/395* | (2006.01) |
| *A61K 31/136* | (2006.01) |
| *A61K 31/7088* | (2006.01) |
| *A61K 31/785* | (2006.01) |
| *A61K 38/21* | (2006.01) |
| *A61K 45/06* | (2006.01) |
| *C12N 15/113* | (2010.01) |
| *C12Q 1/68* | (2006.01) |
| *A61K 48/00* | (2006.01) |

(52) U.S. Cl.
CPC ........... *A61K 39/3955* (2013.01); *A61K 31/136* (2013.01); *A61K 31/7088* (2013.01); *A61K 31/785* (2013.01); *A61K 38/215* (2013.01); *A61K 39/39591* (2013.01); *A61K 45/06* (2013.01); *C12N 15/113* (2013.01); *A61K 48/00* (2013.01); *C12N 2310/11* (2013.01); *C12N 2310/14* (2013.01); *C12N 2310/315* (2013.01); *C12N 2310/3231* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 7,691,997 | B2 | 4/2010 | Khvorova et al. |
| 2007/0178068 | A1 | 8/2007 | Reich et al. |
| 2008/0113351 | A1 | 5/2008 | Naito et al. |
| 2009/0214538 | A1 | 8/2009 | Fung et al. |
| 2010/0143344 | A1 | 6/2010 | Baas et al. |

FOREIGN PATENT DOCUMENTS

| | | |
|---|---|---|
| WO | 03/066805 A2 | 8/2003 |
| WO | 2007/089375 A2 | 8/2007 |
| WO | 2008/044928 A1 | 4/2008 |

OTHER PUBLICATIONS

Barnum, Scott R. et al., "Complement and demyelinating disease: No MAC needed?" Brain Research Reviews, vol. 52:58-68 (2006).

Fluiter, Kees et al., "On the in vitro and in vivo Properties of Four Locked Nucleic Acid Nucleotides Incorporated into an Anti-H-Ras Antisense Oligonucleotide," ChemBioChem, vol. 6:1104-1109 (2005).

Kurreck, Jens et al., "Design of antisense oligonucleotides stabilized by locked nucleic acids," Nucleic Acids Research, vol. 30(9):1911-1918 (2002).

Rapozzi, Valentina et al., "Antisense locked nucleic acids efficiently suppress BCR/ABL and induce cell growth decline and apoptosis in leukemic cells," Mol. Cancer Ther., vol. 5(7):1683-1692 (2006).

Swayze, Eric E. et al., "Antisense oligonucleotides containing locked nucleic acid improve potency but cause significant hepatotoxicity in animals," Nucleic Acids Research, vol. 35(2):687-700 (2007).

International Search Report for Application No. PCT/NL2009/050418, 3 pages, dated Mar. 2, 2010.

*Primary Examiner* — Sean McGarry

(74) *Attorney, Agent, or Firm* — Nelson Mullins Riley & Scarborough LLP; Jane E. Remillard, Esq.; Jeanne M. DiGiorgio, Esq.

(57) ABSTRACT

Disclosed are antagonists designed to inhibit or block expression of a mammalian complement such as complement component 6 (C6). The invention has a wide range of uses including use in the preparation of a medicament for the enhancement of nerve regeneration following acute or chronic nerve damage in a mammal. Additional applications include use in the treatment of multiple sclerosis either alone or in combination with another drug.

20 Claims, 2 Drawing Sheets

SEQUENCE LISTING

<160> NUMBER OF SEQ ID NOS: 423

<210> SEQ ID NO 1
<211> LENGTH: 3606
<212> TYPE: DNA
<213> ORGANISM: Artificial
<220> FEATURE:
<223> OTHER INFORMATION: Synthetic nucleic acid

<400> SEQUENCE: 1

```
aacatttatt ttgacaaccc tctaggtgtt gctaggcttc tgggatatga cagcattgcc      60
ttgtgttagc tagcaataag aaaagaagct ttgtttggat taacatatat accctcttca     120
ttctgcatac ctatttttc cccaataatt tgcagcttag gtccgaggac accacaaact     180
ctgcttaaag ggcctggagg ctctcaaggc atggccagac gctctgtctt gtacttcatc     240
ctgctgaatg ctctgatcaa caagggccaa gcctgcttct gtgatcacta tgcatggact     300
cagtggacca gctgctcaaa aacttgcaat tctggaaccc agagcagaca cagacaaata     360
gtagtagata agtactacca ggaaaacttt tgtgaacaga tttgcagcaa gcaggagact     420
agagaatgta actggcaaag atgccccatc aactgcctcc tgggagattt tggaccatgg     480
tcagactgtg acccttgtat tgaaaaacag tctaaagtta gatctgtctt gcgtcccagt     540
cagtttgggg gacagccatg cactgcgcct ctggtagcct ttcaaccatg cattccatct     600
aagctctgca aaattgaaga ggctgactgc aagaataaat ttcgctgtga cagtggccgc     660
tgcattgcca gaaagttaga atgcaatgga gaaaatgact gtggagacaa ttcagatgaa     720
agggactgtg ggaggacaaa ggcagtatgc acacggaagt ataatcccat ccctagtgta     780
cagttgatgg gcaatggggtt tcattttctg gcaggagagc ccagaggaga agtccttgat     840
aactcttca ctggaggaat atgtaaaact gtcaaaagca gtaggacaag taatccatac     900
cgtgttccgg ccaatctgga aaatgtcggc tttgaggtac aaactgcaga agatgacttg     960
aaaacagatt tctacaagga tttaacttct cttggacaca atgaaaatca acaaggctca    1020
ttctcaagtc aggggggggag ctctttcagt gtaccaattt tttattcctc aaagagaagt    1080
gaaaatatca accataattc tgccttcaaa caagccattc aagcctctca caaaaaggat    1140
tctagtttta ttaggatcca taaagtgatg aaagtcttaa acttcacaac gaaagctaaa    1200
gatctgcacc tttctgatgt cttttttgaaa gcacttaacc atctgcctct agaatacaac    1260
tctgctttgt acagccgaat attcgatgac tttgggactc attacttcac ctctggctcc    1320
ctgggaggcg tgtatgacct tctctatcag tttagcagtg aggaactaaa gaactcaggt    1380
ttaaccgagg aagaagccaa acactgtgtc aggattgaaa caaagaaacg cgttttattt    1440
gctaagaaaa caaagtggaa acataggtgc accaccaaca agctgtcaga gaaacatgaa    1500
ggttcattta tacagggagc agagaaatcc atatccctga ttcgaggtgg aaggagtgaa    1560
tatggagcag cttttggcatg ggagaaaggg agctctggtc tggaggagaa gacattttct    1620
gagtggttag aatcagtgaa ggaaaatcct gctgtgattg actttgagct tgccccccatc    1680
gtggacttgg taagaaacat ccccctgtgca gtgacaaaac ggaacaacct caggaaagct    1740
ttgcaagagt atgcagccaa gttcgatcct tgccagtgtg ctccatgccc taataatggc    1800
cgacccaccc tctcagggac tgaatgtctg tgtgtgtgtc agagtggcac ctatggtgag    1860
aactgtgaga aacagtctcc agattataaa tccaatgcag tagacggaca gtggggttgt    1920
tggtcttcct ggagtacctg tgatgctact tataagagat cgagaacccg agaatgcaat    1980
aatcctgccc ccaacgagg agggaaacgt gtgaggggg agaagcgaca agaggaagac    2040
tgcacatttt caatcatgga aaacaatgga caaccatgta tcaatgatga tgaagaaatg    2100
aaagaggtcg atcttcctga gatagaagca gattccgggt gtcctcagcc agttcctcca    2160
gaaaatggat ttatccggaa tgaaaagcaa ctatacttgg ttggagaaga tgttgaaatt    2220
tcatgcctta ctggctttga aactgttgga taccagtact tcagatgctt accagacggg    2280
```

```
acctggagac aagggatgt ggaatgccaa cggacggagt gcatcaagcc agttgtgcag    2340
gaagtcctga caattacacc atttcagaga ttgtatagaa ttggtgaatc cattgagcta    2400
acttgcccca aaggctttgt tgttgctggg ccatcaaggt acacatgcca ggggaattcc    2460
tggacaccac ccatttcaaa ctctctcacc tgtgaaaaag atactctaac aaaattaaaa    2520
ggccattgtc agctgggaca gaaacaatca ggatctgaat gcatttgtat gtctccagaa    2580
gaagactgta gccatcattc agaagatctc tgtgtgtttg acacagactc caacgattac    2640
tttacttcac ccgcttgtaa gttttttggct gagaaatgtt taaataatca gcaactccat    2700
tttctacata ttggttcctg ccaagacggc cgccagttag aatggggtct tgaaaggaca    2760
agactttcat ccaacagcac aaagaaagaa tcctgtggct atgacacctg ctatgactgg    2820
gaaaaatgtt cagcctccac ttccaaatgt gtctgcctat tgcccccaca gtgcttcaag    2880
ggtggaaacc aactctactg tgtcaaaatg ggatcatcaa caagtgagaa acattgaac    2940 atctgtgaag tgggaactat aagatgtgca aacaggaaga tggaaatact gcatcctgga    3000
aagtgtttgg cctagcacaa ttactgctag gcccagcaca atgaacagat ttaccatccc    3060
gaagaaccaa ctcctacaaa tgagaattct tgcacaaaca gcagactggc atgctcaaag    3120
ttactgacaa aaattatttt ctgttagttt gagatcatta ttctcccctg actctcctgt    3180
ttgggcatgt cttattcagt tccagctcat gacgccctgt agcataccc taggtaccaa    3240 cttccacagc agtctcgtaa attcctcctgt tcacattgta caaaaataat gtgacttctg    3300
aggcccttat gtagcctgtg acattaagca ttctcgcaat tagaaataag aataaaaccc    3360
ataattttct tcaatgagtt aataaacaga aatctccaga acctctgaaa cacattcttg    3420
aagcccagct ttcatatctt cattcaacaa ataatttctg agtgtgtata caggatgtca    3480
agtactgacc aaagtcctga gaactcggca gataataaaa cagacaaaag cctttgcctt    3540
catgaagcat acattcattc aggggtagac acacaaaaaa tgaaataaac aggtaaaata    3600
tgtagc                                                               3606
```

<210> SEQ ID NO 2
<211> LENGTH: 25
<212> TYPE: DNA
<213> ORGANISM: Artificial
<220> FEATURE:
<223> OTHER INFORMATION: synthetic oligonucleotide

<400> SEQUENCE: 2
catctgcctc tagaatacaa ctctg                                          25

<210> SEQ ID NO 3
<211> LENGTH: 19
<212> TYPE: DNA
<213> ORGANISM: Artificial
<220> FEATURE:
<223> OTHER INFORMATION: synthetic oligonucleotide

<400> SEQUENCE: 3
atctgcctct agaatacaa                                                 19

<210> SEQ ID NO 4
<211> LENGTH: 19
<212> TYPE: DNA
<213> ORGANISM: Artificial
<220> FEATURE:
<223> OTHER INFORMATION: synthetic oligonucleotide

<400> SEQUENCE: 4

```
catctgcctc tagaataca                                                    19

<210> SEQ ID NO 5
<211> LENGTH: 19
<212> TYPE: DNA
<213> ORGANISM: Artificial
<220> FEATURE:
<223> OTHER INFORMATION: synthetic oligonucleotide

<400> SEQUENCE: 5
ctgcctctag aatacaact                                                    19

<210> SEQ ID NO 6
<211> LENGTH: 19
<212> TYPE: DNA
<213> ORGANISM: Artificial
<220> FEATURE:
<223> OTHER INFORMATION: synthetic oligonucleotide

<400> SEQUENCE: 6
gcctctagaa tacaactct                                                    19

<210> SEQ ID NO 7
<211> LENGTH: 19
<212> TYPE: DNA
<213> ORGANISM: Artificial
<220> FEATURE:
<223> OTHER INFORMATION: synthetic oligonucleotide

<400> SEQUENCE: 7
tctgcctcta gaatacaac                                                    19

<210> SEQ ID NO 8
<211> LENGTH: 19
<212> TYPE: DNA
<213> ORGANISM: Artificial
<220> FEATURE:
<223> OTHER INFORMATION: synthetic oligonucleotide

<400> SEQUENCE: 8
tgcctctaga atacaactc                                                    19

<210> SEQ ID NO 9
<211> LENGTH: 19
<212> TYPE: DNA
<213> ORGANISM: Artificial
<220> FEATURE:
<223> OTHER INFORMATION: synthetic oligonucleotide

<400> SEQUENCE: 9
cctctagaat acaactctg                                                    19

<210> SEQ ID NO 10
<211> LENGTH: 19
<212> TYPE: RNA
<213> ORGANISM: Artificial
<220> FEATURE:
<223> OTHER INFORMATION: synthetic oligonucleotide

<400> SEQUENCE: 10
aucugccucu agaauacaa                                                    19

<210> SEQ ID NO 11
<211> LENGTH: 19
<212> TYPE: RNA
```

```
<213> ORGANISM: Artificial
<220> FEATURE:
<223> OTHER INFORMATION: synthetic oligonucleotide

<400> SEQUENCE: 11
caucugccuc uagaauaca                                              19

<210> SEQ ID NO 12
<211> LENGTH: 19
<212> TYPE: RNA
<213> ORGANISM: Artificial
<220> FEATURE:
<223> OTHER INFORMATION: synthetic oligonucleotide

<400> SEQUENCE: 12
cugccucuag aauacaacu                                              19

<210> SEQ ID NO 13
<211> LENGTH: 19
<212> TYPE: RNA
<213> ORGANISM: Artificial
<220> FEATURE:
<223> OTHER INFORMATION: synthetic oligonucleotide

<400> SEQUENCE: 13
gccucuagaa uacaacucu                                              19

<210> SEQ ID NO 14
<211> LENGTH: 19
<212> TYPE: RNA
<213> ORGANISM: Artificial
<220> FEATURE:
<223> OTHER INFORMATION: synthetic oligonucleotide

<400> SEQUENCE: 14
ucugccucua gaauacaac                                              19

<210> SEQ ID NO 15
<211> LENGTH: 19
<212> TYPE: RNA
<213> ORGANISM: Artificial
<220> FEATURE:
<223> OTHER INFORMATION: synthetic oligonucleotide

<400> SEQUENCE: 15
ugccucuaga auacaacuc                                              19

<210> SEQ ID NO 16
<211> LENGTH: 19
<212> TYPE: RNA
<213> ORGANISM: Artificial
<220> FEATURE:
<223> OTHER INFORMATION: synthetic oligonucleotide

<400> SEQUENCE: 16
ccucuagaau acaacucug                                              19

<210> SEQ ID NO 17
<211> LENGTH: 19
<212> TYPE: RNA
<213> ORGANISM: Artificial
<220> FEATURE:
<223> OTHER INFORMATION: synthetic oligonucleotide

<400> SEQUENCE: 17
uuguauucua gaggcagau                                              19
```

```
<210> SEQ ID NO 18
<211> LENGTH: 19
<212> TYPE: RNA
<213> ORGANISM: Artificial
<220> FEATURE:
<223> OTHER INFORMATION: synthetic oligonucleotide

<400> SEQUENCE: 18
uguauucuag aggcagaug                                              19

<210> SEQ ID NO 19
<211> LENGTH: 19
<212> TYPE: RNA
<213> ORGANISM: Artificial
<220> FEATURE:
<223> OTHER INFORMATION: synthetic oligonucleotide

<400> SEQUENCE: 19
aguuguauuc uagaggcag                                              19

<210> SEQ ID NO 20
<211> LENGTH: 19
<212> TYPE: RNA
<213> ORGANISM: Artificial
<220> FEATURE:
<223> OTHER INFORMATION: synthetic oligonucleotide

<400> SEQUENCE: 20
agaguuguau ucuagaggc                                              19

<210> SEQ ID NO 21
<211> LENGTH: 19
<212> TYPE: RNA
<213> ORGANISM: Artificial
<220> FEATURE:
<223> OTHER INFORMATION: synthetic oligonucleotide

<400> SEQUENCE: 21
guuguauucu agaggcaga                                              19

<210> SEQ ID NO 22
<211> LENGTH: 19
<212> TYPE: RNA
<213> ORGANISM: Artificial
<220> FEATURE:
<223> OTHER INFORMATION: synthetic oligonucleotide

<400> SEQUENCE: 22
gaguuguauu cuagaggca                                              19

<210> SEQ ID NO 23
<211> LENGTH: 19
<212> TYPE: RNA
<213> ORGANISM: Artificial
<220> FEATURE:
<223> OTHER INFORMATION: synthetic oligonucleotide

<400> SEQUENCE: 23
cagaguugua uucuagagg                                              19

<210> SEQ ID NO 24
<211> LENGTH: 25
<212> TYPE: DNA
<213> ORGANISM: Artificial
<220> FEATURE:
```

-continued

<223> OTHER INFORMATION: synthetic oligonucleotide

<400> SEQUENCE: 24
tgggaggcgt gtatgacctt ctcta                                      25

<210> SEQ ID NO 25
<211> LENGTH: 19
<212> TYPE: DNA
<213> ORGANISM: Artificial
<220> FEATURE:
<223> OTHER INFORMATION: synthetic oligonucleotide

<400> SEQUENCE: 25
gcgtgtatga ccttctcta                                             19

<210> SEQ ID NO 26
<211> LENGTH: 19
<212> TYPE: DNA
<213> ORGANISM: Artificial
<220> FEATURE:
<223> OTHER INFORMATION: synthetic oligonucleotide

<400> SEQUENCE: 26
gaggcgtgta tgaccttct                                             19

<210> SEQ ID NO 27
<211> LENGTH: 19
<212> TYPE: DNA
<213> ORGANISM: Artificial
<220> FEATURE:
<223> OTHER INFORMATION: synthetic oligonucleotide

<400> SEQUENCE: 27
aggcgtgtat gaccttctc                                             19

<210> SEQ ID NO 28
<211> LENGTH: 19
<212> TYPE: DNA
<213> ORGANISM: Artificial
<220> FEATURE:
<223> OTHER INFORMATION: synthetic oligonucleotide

<400> SEQUENCE: 28
ggcgtgtatg accttctct                                             19

<210> SEQ ID NO 29
<211> LENGTH: 19
<212> TYPE: DNA
<213> ORGANISM: Artificial
<220> FEATURE:
<223> OTHER INFORMATION: synthetic oligonucleotide

<400> SEQUENCE: 29
tgggaggcgt gtatgacct                                             19

<210> SEQ ID NO 30
<211> LENGTH: 19
<212> TYPE: DNA
<213> ORGANISM: Artificial
<220> FEATURE:
<223> OTHER INFORMATION: synthetic oligonucleotide

<400> SEQUENCE: 30
gggaggcgtg tatgacctt                                             19

```
<210> SEQ ID NO 31
<211> LENGTH: 19
<212> TYPE: DNA
<213> ORGANISM: Artificial
<220> FEATURE:
<223> OTHER INFORMATION: synthetic oligonucleotide

<400> SEQUENCE: 31
ggaggcgtgt atgaccttc                                               19

<210> SEQ ID NO 32
<211> LENGTH: 19
<212> TYPE: RNA
<213> ORGANISM: Artificial
<220> FEATURE:
<223> OTHER INFORMATION: synthetic oligonucleotide

<400> SEQUENCE: 32
gcguguauga ccuucucua                                               19

<210> SEQ ID NO 33
<211> LENGTH: 19
<212> TYPE: RNA
<213> ORGANISM: Artificial
<220> FEATURE:
<223> OTHER INFORMATION: synthetic oligonucleotide

<400> SEQUENCE: 33
gaggcgugua ugaccuucu                                               19

<210> SEQ ID NO 34
<211> LENGTH: 19
<212> TYPE: RNA
<213> ORGANISM: Artificial
<220> FEATURE:
<223> OTHER INFORMATION: synthetic oligonucleotide

<400> SEQUENCE: 34
aggcguguau gaccuucuc                                               19

<210> SEQ ID NO 35
<211> LENGTH: 19
<212> TYPE: RNA
<213> ORGANISM: Artificial
<220> FEATURE:
<223> OTHER INFORMATION: synthetic oligonucleotide

<400> SEQUENCE: 35
ggcguguaug accuucucu                                               19

<210> SEQ ID NO 36
<211> LENGTH: 19
<212> TYPE: RNA
<213> ORGANISM: Artificial
<220> FEATURE:
<223> OTHER INFORMATION: synthetic oligonucleotide

<400> SEQUENCE: 36
ugggaggcgu guaugaccu                                               19

<210> SEQ ID NO 37
<211> LENGTH: 19
<212> TYPE: RNA
<213> ORGANISM: Artificial
<220> FEATURE:
<223> OTHER INFORMATION: synthetic oligonucleotide
```

-continued

```
<400> SEQUENCE: 37
gggaggcgug uaugaccuu                                                    19

<210> SEQ ID NO 38
<211> LENGTH: 19
<212> TYPE: RNA
<213> ORGANISM: Artificial
<220> FEATURE:
<223> OTHER INFORMATION: synthetic oligonucleotide

<400> SEQUENCE: 38
ggaggcgugu augaccuuc                                                    19

<210> SEQ ID NO 39
<211> LENGTH: 19
<212> TYPE: RNA
<213> ORGANISM: Artificial
<220> FEATURE:
<223> OTHER INFORMATION: synthetic oligonucleotide

<400> SEQUENCE: 39
uagagaaggu cauacacgc                                                    19

<210> SEQ ID NO 40
<211> LENGTH: 19
<212> TYPE: RNA
<213> ORGANISM: Artificial
<220> FEATURE:
<223> OTHER INFORMATION: synthetic oligonucleotide

<400> SEQUENCE: 40
agaaggucau acacgccuc                                                    19

<210> SEQ ID NO 41
<211> LENGTH: 18
<212> TYPE: RNA
<213> ORGANISM: Artificial
<220> FEATURE:
<223> OTHER INFORMATION: synthetic oligonucleotide

<400> SEQUENCE: 41
agaaggucau acacgccu                                                     18

<210> SEQ ID NO 42
<211> LENGTH: 19
<212> TYPE: RNA
<213> ORGANISM: Artificial
<220> FEATURE:
<223> OTHER INFORMATION: synthetic oligonucleotide

<400> SEQUENCE: 42
agagaagguc auacacgcc                                                    19

<210> SEQ ID NO 43
<211> LENGTH: 19
<212> TYPE: RNA
<213> ORGANISM: Artificial
<220> FEATURE:
<223> OTHER INFORMATION: synthetic oligonucleotide

<400> SEQUENCE: 43
aggucauaca cgccuccca                                                    19

<210> SEQ ID NO 44
<211> LENGTH: 19
```

```
<212> TYPE: RNA
<213> ORGANISM: Artificial
<220> FEATURE:
<223> OTHER INFORMATION: synthetic oligonucleotide

<400> SEQUENCE: 44
aaggucauac acgccuccc                                              19

<210> SEQ ID NO 45
<211> LENGTH: 19
<212> TYPE: RNA
<213> ORGANISM: Artificial
<220> FEATURE:
<223> OTHER INFORMATION: synthetic oligonucleotide

<400> SEQUENCE: 45
gaaggucaua cacgccucc                                              19

<210> SEQ ID NO 46
<211> LENGTH: 25
<212> TYPE: DNA
<213> ORGANISM: Artificial
<220> FEATURE:
<223> OTHER INFORMATION: synthetic oligonucleotide

<400> SEQUENCE: 46
gaggcgtgta tgaccttctc tatca                                       25

<210> SEQ ID NO 47
<211> LENGTH: 19
<212> TYPE: DNA
<213> ORGANISM: Artificial
<220> FEATURE:
<223> OTHER INFORMATION: synthetic oligonucleotide

<400> SEQUENCE: 47
tgtatgacct tctctatca                                              19

<210> SEQ ID NO 48
<211> LENGTH: 19
<212> TYPE: DNA
<213> ORGANISM: Artificial
<220> FEATURE:
<223> OTHER INFORMATION: synthetic oligonucleotide

<400> SEQUENCE: 48
gcgtgtatga ccttctcta                                              19

<210> SEQ ID NO 49
<211> LENGTH: 19
<212> TYPE: DNA
<213> ORGANISM: Artificial
<220> FEATURE:
<223> OTHER INFORMATION: synthetic oligonucleotide

<400> SEQUENCE: 49
cgtgtatgac cttctctat                                              19

<210> SEQ ID NO 50
<211> LENGTH: 19
<212> TYPE: DNA
<213> ORGANISM: Artificial
<220> FEATURE:
<223> OTHER INFORMATION: synthetic oligonucleotide

<400> SEQUENCE: 50
```
gaggcgtgta tgaccttct                                                    19

<210> SEQ ID NO 51
<211> LENGTH: 19
<212> TYPE: DNA
<213> ORGANISM: Artificial
<220> FEATURE:
<223> OTHER INFORMATION: synthetic oligonucleotide

<400> SEQUENCE: 51
aggcgtgtat gaccttctc                                                    19

<210> SEQ ID NO 52
<211> LENGTH: 19
<212> TYPE: DNA
<213> ORGANISM: Artificial
<220> FEATURE:
<223> OTHER INFORMATION: synthetic oligonucleotide

<400> SEQUENCE: 52
ggcgtgtatg accttctct                                                    19

<210> SEQ ID NO 53
<211> LENGTH: 19
<212> TYPE: DNA
<213> ORGANISM: Artificial
<220> FEATURE:
<223> OTHER INFORMATION: synthetic oligonucleotide

<400> SEQUENCE: 53
gtgtatgacc ttctctatc                                                    19

<210> SEQ ID NO 54
<211> LENGTH: 19
<212> TYPE: RNA
<213> ORGANISM: Artificial
<220> FEATURE:
<223> OTHER INFORMATION: synthetic oligonucleotide

<400> SEQUENCE: 54
uguaugaccu ucucuauca                                                    19

<210> SEQ ID NO 55
<211> LENGTH: 19
<212> TYPE: RNA
<213> ORGANISM: Artificial
<220> FEATURE:
<223> OTHER INFORMATION: synthetic oligonucleotide

<400> SEQUENCE: 55
gcguguauga ccuucucua                                                    19

<210> SEQ ID NO 56
<211> LENGTH: 19
<212> TYPE: RNA
<213> ORGANISM: Artificial
<220> FEATURE:
<223> OTHER INFORMATION: synthetic oligonucleotide

<400> SEQUENCE: 56
cguguaugac cuucucuau                                                    19

<210> SEQ ID NO 57
<211> LENGTH: 19
<212> TYPE: RNA
<213> ORGANISM: Artificial

```
<220> FEATURE:
<223> OTHER INFORMATION: synthetic oligonucleotide

<400> SEQUENCE: 57
gaggcgugua ugaccuucu                                                19

<210> SEQ ID NO 58
<211> LENGTH: 19
<212> TYPE: RNA
<213> ORGANISM: Artificial
<220> FEATURE:
<223> OTHER INFORMATION: synthetic oligonucleotide

<400> SEQUENCE: 58
aggcguguau gaccuucuc                                                19

<210> SEQ ID NO 59
<211> LENGTH: 19
<212> TYPE: RNA
<213> ORGANISM: Artificial
<220> FEATURE:
<223> OTHER INFORMATION: synthetic oligonucleotide

<400> SEQUENCE: 59
ggcguguaug accuucucu                                                19

<210> SEQ ID NO 60
<211> LENGTH: 19
<212> TYPE: RNA
<213> ORGANISM: Artificial
<220> FEATURE:
<223> OTHER INFORMATION: synthetic oligonucleotide

<400> SEQUENCE: 60
guguaugacc uucucuauc                                                19

<210> SEQ ID NO 61
<211> LENGTH: 19
<212> TYPE: RNA
<213> ORGANISM: Artificial
<220> FEATURE:
<223> OTHER INFORMATION: synthetic oligonucleotide

<400> SEQUENCE: 61
ugauagagaa ggucauaca                                                19

<210> SEQ ID NO 62
<211> LENGTH: 19
<212> TYPE: RNA
<213> ORGANISM: Artificial
<220> FEATURE:
<223> OTHER INFORMATION: synthetic oligonucleotide

<400> SEQUENCE: 62
uagagaaggu cauacacgc                                                19

<210> SEQ ID NO 63
<211> LENGTH: 19
<212> TYPE: RNA
<213> ORGANISM: Artificial
<220> FEATURE:
<223> OTHER INFORMATION: synthetic oligonucleotide

<400> SEQUENCE: 63
auagagaagg ucauacacg                                                19
```

```
<210> SEQ ID NO 64
<211> LENGTH: 19
<212> TYPE: RNA
<213> ORGANISM: Artificial
<220> FEATURE:
<223> OTHER INFORMATION: synthetic oligonucleotide

<400> SEQUENCE: 64
agaaggucau acacgccuc                                                19

<210> SEQ ID NO 65
<211> LENGTH: 19
<212> TYPE: RNA
<213> ORGANISM: Artificial
<220> FEATURE:
<223> OTHER INFORMATION: synthetic oligonucleotide

<400> SEQUENCE: 65
gagaagguca uacacgccu                                                19

<210> SEQ ID NO 66
<211> LENGTH: 19
<212> TYPE: RNA
<213> ORGANISM: Artificial
<220> FEATURE:
<223> OTHER INFORMATION: synthetic oligonucleotide

<400> SEQUENCE: 66
agagaagguc auacacgcc                                                19

<210> SEQ ID NO 67
<211> LENGTH: 19
<212> TYPE: RNA
<213> ORGANISM: Artificial
<220> FEATURE:
<223> OTHER INFORMATION: synthetic oligonucleotide

<400> SEQUENCE: 67
gauagagaag gucauacac                                                19

<210> SEQ ID NO 68
<211> LENGTH: 25
<212> TYPE: DNA
<213> ORGANISM: Artificial
<220> FEATURE:
<223> OTHER INFORMATION: synthetic oligonucleotide

<400> SEQUENCE: 68
gccaaacact gtgtcaggat tgaaa                                         25

<210> SEQ ID NO 69
<211> LENGTH: 19
<212> TYPE: DNA
<213> ORGANISM: Artificial
<220> FEATURE:
<223> OTHER INFORMATION: synthetic oligonucleotide

<400> SEQUENCE: 69
caaacactgt gtcaggatt                                                19

<210> SEQ ID NO 70
<211> LENGTH: 19
<212> TYPE: DNA
<213> ORGANISM: Artificial
<220> FEATURE:
<223> OTHER INFORMATION: synthetic oligonucleotide
```

<400> SEQUENCE: 70
aacactgtgt caggattga                                                    19

<210> SEQ ID NO 71
<211> LENGTH: 19
<212> TYPE: DNA
<213> ORGANISM: Artificial
<220> FEATURE:
<223> OTHER INFORMATION: synthetic oligonucleotide

<400> SEQUENCE: 71
acactgtgtc aggattgaa                                                    19

<210> SEQ ID NO 72
<211> LENGTH: 19
<212> TYPE: DNA
<213> ORGANISM: Artificial
<220> FEATURE:
<223> OTHER INFORMATION: synthetic oligonucleotide

<400> SEQUENCE: 72
cactgtgtca ggattgaaa                                                    19

<210> SEQ ID NO 73
<211> LENGTH: 19
<212> TYPE: DNA
<213> ORGANISM: Artificial
<220> FEATURE:
<223> OTHER INFORMATION: synthetic oligonucleotide

<400> SEQUENCE: 73
ccaaacactg tgtcaggat                                                    19

<210> SEQ ID NO 74
<211> LENGTH: 19
<212> TYPE: DNA
<213> ORGANISM: Artificial
<220> FEATURE:
<223> OTHER INFORMATION: synthetic oligonucleotide

<400> SEQUENCE: 74
gccaaacact gtgtcagga                                                    19

<210> SEQ ID NO 75
<211> LENGTH: 19
<212> TYPE: DNA
<213> ORGANISM: Artificial
<220> FEATURE:
<223> OTHER INFORMATION: synthetic oligonucleotide

<400> SEQUENCE: 75
aaacactgtg tcaggattg                                                    19

<210> SEQ ID NO 76
<211> LENGTH: 19
<212> TYPE: RNA
<213> ORGANISM: Artificial
<220> FEATURE:
<223> OTHER INFORMATION: synthetic oligonucleotide

<400> SEQUENCE: 76
caaacacugu gucaggauu                                                    19

<210> SEQ ID NO 77

```
<211> LENGTH: 19
<212> TYPE: RNA
<213> ORGANISM: Artificial
<220> FEATURE:
<223> OTHER INFORMATION: synthetic oligonucleotide

<400> SEQUENCE: 77
aacacugugu caggauuga                                                  19

<210> SEQ ID NO 78
<211> LENGTH: 19
<212> TYPE: RNA
<213> ORGANISM: Artificial
<220> FEATURE:
<223> OTHER INFORMATION: synthetic oligonucleotide

<400> SEQUENCE: 78
acacuguguc aggauugaa                                                  19

<210> SEQ ID NO 79
<211> LENGTH: 19
<212> TYPE: RNA
<213> ORGANISM: Artificial
<220> FEATURE:
<223> OTHER INFORMATION: synthetic oligonucleotide

<400> SEQUENCE: 79
cacuguguca ggauugaaa                                                  19

<210> SEQ ID NO 80
<211> LENGTH: 19
<212> TYPE: RNA
<213> ORGANISM: Artificial
<220> FEATURE:
<223> OTHER INFORMATION: synthetic oligonucleotide

<400> SEQUENCE: 80
ccaaacacug ugucaggau                                                  19

<210> SEQ ID NO 81
<211> LENGTH: 19
<212> TYPE: RNA
<213> ORGANISM: Artificial
<220> FEATURE:
<223> OTHER INFORMATION: synthetic oligonucleotide

<400> SEQUENCE: 81
gccaaacacu gugucagga                                                  19

<210> SEQ ID NO 82
<211> LENGTH: 19
<212> TYPE: RNA
<213> ORGANISM: Artificial
<220> FEATURE:
<223> OTHER INFORMATION: synthetic oligonucleotide

<400> SEQUENCE: 82
aaacacugug ucaggauug                                                  19

<210> SEQ ID NO 83
<211> LENGTH: 19
<212> TYPE: RNA
<213> ORGANISM: Artificial
<220> FEATURE:
<223> OTHER INFORMATION: synthetic oligonucleotide

<400> SEQUENCE: 83
```

```
aauccugaca caguguuug                                              19

<210> SEQ ID NO 84
<211> LENGTH: 19
<212> TYPE: RNA
<213> ORGANISM: Artificial
<220> FEATURE:
<223> OTHER INFORMATION: synthetic oligonucleotide

<400> SEQUENCE: 84
ucaauccuga cacaguguu                                              19

<210> SEQ ID NO 85
<211> LENGTH: 19
<212> TYPE: RNA
<213> ORGANISM: Artificial
<220> FEATURE:
<223> OTHER INFORMATION: synthetic oligonucleotide

<400> SEQUENCE: 85
uucaauccug acacagugu                                              19

<210> SEQ ID NO 86
<211> LENGTH: 19
<212> TYPE: RNA
<213> ORGANISM: Artificial
<220> FEATURE:
<223> OTHER INFORMATION: synthetic oligonucleotide

<400> SEQUENCE: 86
uuucaauccu gacacagug                                              19

<210> SEQ ID NO 87
<211> LENGTH: 19
<212> TYPE: RNA
<213> ORGANISM: Artificial
<220> FEATURE:
<223> OTHER INFORMATION: synthetic oligonucleotide

<400> SEQUENCE: 87
auccugacac aguguuugg                                              19

<210> SEQ ID NO 88
<211> LENGTH: 19
<212> TYPE: RNA
<213> ORGANISM: Artificial
<220> FEATURE:
<223> OTHER INFORMATION: synthetic oligonucleotide

<400> SEQUENCE: 88
uccugacaca guguuuggc                                              19

<210> SEQ ID NO 89
<211> LENGTH: 19
<212> TYPE: RNA
<213> ORGANISM: Artificial
<220> FEATURE:
<223> OTHER INFORMATION: synthetic oligonucleotide

<400> SEQUENCE: 89
caauccugac acaguguuu                                              19

<210> SEQ ID NO 90
<211> LENGTH: 25
<212> TYPE: DNA
```

```
<213> ORGANISM: Artificial
<220> FEATURE:
<223> OTHER INFORMATION: synthetic oligonucleotide

<400> SEQUENCE: 90
gcaccaccaa caagctgtca gagaa                                          25

<210> SEQ ID NO 91
<211> LENGTH: 19
<212> TYPE: DNA
<213> ORGANISM: Artificial
<220> FEATURE:
<223> OTHER INFORMATION: synthetic oligonucleotide

<400> SEQUENCE: 91
ccaacaagct gtcagagaa                                                 19

<210> SEQ ID NO 92
<211> LENGTH: 19
<212> TYPE: DNA
<213> ORGANISM: Artificial
<220> FEATURE:
<223> OTHER INFORMATION: synthetic oligonucleotide

<400> SEQUENCE: 92
ccaccaacaa gctgtcaga                                                 19

<210> SEQ ID NO 93
<211> LENGTH: 19
<212> TYPE: DNA
<213> ORGANISM: Artificial
<220> FEATURE:
<223> OTHER INFORMATION: synthetic oligonucleotide

<400> SEQUENCE: 93
accaacaagc tgtcagaga                                                 19

<210> SEQ ID NO 94
<211> LENGTH: 19
<212> TYPE: DNA
<213> ORGANISM: Artificial
<220> FEATURE:
<223> OTHER INFORMATION: synthetic oligonucleotide

<400> SEQUENCE: 94
caccaccaac aagctgtca                                                 19

<210> SEQ ID NO 95
<211> LENGTH: 19
<212> TYPE: DNA
<213> ORGANISM: Artificial
<220> FEATURE:
<223> OTHER INFORMATION: synthetic oligonucleotide

<400> SEQUENCE: 95
accaccaaca agctgtcag                                                 19

<210> SEQ ID NO 96
<211> LENGTH: 19
<212> TYPE: DNA
<213> ORGANISM: Artificial
<220> FEATURE:
<223> OTHER INFORMATION: synthetic oligonucleotide

<400> SEQUENCE: 96
gcaccaccaa caagctgtc                                                 19
```

```
<210> SEQ ID NO 97
<211> LENGTH: 19
<212> TYPE: DNA
<213> ORGANISM: Artificial
<220> FEATURE:
<223> OTHER INFORMATION: synthetic oligonucleotide

<400> SEQUENCE: 97
caccaacaag ctgtcagag                                                19

<210> SEQ ID NO 98
<211> LENGTH: 19
<212> TYPE: RNA
<213> ORGANISM: Artificial
<220> FEATURE:
<223> OTHER INFORMATION: synthetic oligonucleotide

<400> SEQUENCE: 98
ccaacaagcu gucagagaa                                                19

<210> SEQ ID NO 99
<211> LENGTH: 19
<212> TYPE: RNA
<213> ORGANISM: Artificial
<220> FEATURE:
<223> OTHER INFORMATION: synthetic oligonucleotide

<400> SEQUENCE: 99
ccaccaacaa gcugucaga                                                19

<210> SEQ ID NO 100
<211> LENGTH: 19
<212> TYPE: RNA
<213> ORGANISM: Artificial
<220> FEATURE:
<223> OTHER INFORMATION: synthetic oligonucleotide

<400> SEQUENCE: 100
accaacaagc ugucagaga                                                19

<210> SEQ ID NO 101
<211> LENGTH: 19
<212> TYPE: RNA
<213> ORGANISM: Artificial
<220> FEATURE:
<223> OTHER INFORMATION: synthetic oligonucleotide

<400> SEQUENCE: 101
caccaccaac aagcuguca                                                19

<210> SEQ ID NO 102
<211> LENGTH: 19
<212> TYPE: RNA
<213> ORGANISM: Artificial
<220> FEATURE:
<223> OTHER INFORMATION: synthetic oligonucleotide

<400> SEQUENCE: 102
accaccaaca agcugucag                                                19

<210> SEQ ID NO 103
<211> LENGTH: 19
<212> TYPE: RNA
<213> ORGANISM: Artificial
<220> FEATURE:
```

```
<223> OTHER INFORMATION: synthetic oligonucleotide

<400> SEQUENCE: 103
gcaccaccaa caagcuguc                                                19

<210> SEQ ID NO 104
<211> LENGTH: 19
<212> TYPE: RNA
<213> ORGANISM: Artificial
<220> FEATURE:
<223> OTHER INFORMATION: synthetic oligonucleotide

<400> SEQUENCE: 104
caccaacaag cugucagag                                                19

<210> SEQ ID NO 105
<211> LENGTH: 19
<212> TYPE: RNA
<213> ORGANISM: Artificial
<220> FEATURE:
<223> OTHER INFORMATION: synthetic oligonucleotide

<400> SEQUENCE: 105
uucucugaca gcuuguugg                                                19

<210> SEQ ID NO 106
<211> LENGTH: 19
<212> TYPE: RNA
<213> ORGANISM: Artificial
<220> FEATURE:
<223> OTHER INFORMATION: synthetic oligonucleotide

<400> SEQUENCE: 106
ucugacagcu uguuggugg                                                19

<210> SEQ ID NO 107
<211> LENGTH: 19
<212> TYPE: RNA
<213> ORGANISM: Artificial
<220> FEATURE:
<223> OTHER INFORMATION: synthetic oligonucleotide

<400> SEQUENCE: 107
ucucugacag cuuguuggu                                                19

<210> SEQ ID NO 108
<211> LENGTH: 19
<212> TYPE: RNA
<213> ORGANISM: Artificial
<220> FEATURE:
<223> OTHER INFORMATION: synthetic oligonucleotide

<400> SEQUENCE: 108
ugacagcuug uugguggug                                                19

<210> SEQ ID NO 109
<211> LENGTH: 19
<212> TYPE: RNA
<213> ORGANISM: Artificial
<220> FEATURE:
<223> OTHER INFORMATION: synthetic oligonucleotide

<400> SEQUENCE: 109
cugacagcuu guuggggu                                                 19
```

```
<210> SEQ ID NO 110
<211> LENGTH: 19
<212> TYPE: RNA
<213> ORGANISM: Artificial
<220> FEATURE:
<223> OTHER INFORMATION: synthetic oligonucleotide

<400> SEQUENCE: 110
gacagcuugu ugguggugc                                                   19

<210> SEQ ID NO 111
<211> LENGTH: 19
<212> TYPE: RNA
<213> ORGANISM: Artificial
<220> FEATURE:
<223> OTHER INFORMATION: synthetic oligonucleotide

<400> SEQUENCE: 111
cucugacagc uuguuggug                                                   19

<210> SEQ ID NO 112
<211> LENGTH: 25
<212> TYPE: DNA
<213> ORGANISM: Artificial
<220> FEATURE:
<223> OTHER INFORMATION: synthetic oligonucleotide

<400> SEQUENCE: 112
gggacagaaa caatcaggat ctgaa                                            25

<210> SEQ ID NO 113
<211> LENGTH: 19
<212> TYPE: DNA
<213> ORGANISM: Artificial
<220> FEATURE:
<223> OTHER INFORMATION: synthetic oligonucleotide

<400> SEQUENCE: 113
gaaacaatca ggatctgaa                                                   19

<210> SEQ ID NO 114
<211> LENGTH: 19
<212> TYPE: DNA
<213> ORGANISM: Artificial
<220> FEATURE:
<223> OTHER INFORMATION: synthetic oligonucleotide

<400> SEQUENCE: 114
ggacagaaac aatcaggat                                                   19

<210> SEQ ID NO 115
<211> LENGTH: 19
<212> TYPE: DNA
<213> ORGANISM: Artificial
<220> FEATURE:
<223> OTHER INFORMATION: synthetic oligonucleotide

<400> SEQUENCE: 115
acagaaacaa tcaggatct                                                   19

<210> SEQ ID NO 116
<211> LENGTH: 19
<212> TYPE: DNA
<213> ORGANISM: Artificial
<220> FEATURE:
<223> OTHER INFORMATION: synthetic oligonucleotide
```

```
<400> SEQUENCE: 116
agaaacaatc aggatctga                                                     19

<210> SEQ ID NO 117
<211> LENGTH: 19
<212> TYPE: DNA
<213> ORGANISM: Artificial
<220> FEATURE:
<223> OTHER INFORMATION: synthetic oligonucleotide

<400> SEQUENCE: 117
gggacagaaa caatcagga                                                     19

<210> SEQ ID NO 118
<211> LENGTH: 19
<212> TYPE: DNA
<213> ORGANISM: Artificial
<220> FEATURE:
<223> OTHER INFORMATION: synthetic oligonucleotide

<400> SEQUENCE: 118
cagaaacaat caggatctg                                                     19

<210> SEQ ID NO 119
<211> LENGTH: 19
<212> TYPE: DNA
<213> ORGANISM: Artificial
<220> FEATURE:
<223> OTHER INFORMATION: synthetic oligonucleotide

<400> SEQUENCE: 119
gacagaaaca atcaggatc                                                     19

<210> SEQ ID NO 120
<211> LENGTH: 19
<212> TYPE: RNA
<213> ORGANISM: Artificial
<220> FEATURE:
<223> OTHER INFORMATION: synthetic oligonucleotide

<400> SEQUENCE: 120
gaaacaauca ggaucugaa                                                     19

<210> SEQ ID NO 121
<211> LENGTH: 19
<212> TYPE: RNA
<213> ORGANISM: Artificial
<220> FEATURE:
<223> OTHER INFORMATION: synthetic oligonucleotide

<400> SEQUENCE: 121
ggacagaaac aaucaggau                                                     19

<210> SEQ ID NO 122
<211> LENGTH: 19
<212> TYPE: RNA
<213> ORGANISM: Artificial
<220> FEATURE:
<223> OTHER INFORMATION: synthetic oligonucleotide

<400> SEQUENCE: 122
acagaaacaa ucaggaucu                                                     19

<210> SEQ ID NO 123
<211> LENGTH: 19
```

```
<212> TYPE: RNA
<213> ORGANISM: Artificial
<220> FEATURE:
<223> OTHER INFORMATION: synthetic oligonucleotide

<400> SEQUENCE: 123
acagaaacaa ucaggaucu                                                19

<210> SEQ ID NO 124
<211> LENGTH: 19
<212> TYPE: RNA
<213> ORGANISM: Artificial
<220> FEATURE:
<223> OTHER INFORMATION: synthetic oligonucleotide

<400> SEQUENCE: 124
gggacagaaa caaucagga                                                19

<210> SEQ ID NO 125
<211> LENGTH: 19
<212> TYPE: RNA
<213> ORGANISM: Artificial
<220> FEATURE:
<223> OTHER INFORMATION: synthetic oligonucleotide

<400> SEQUENCE: 125
cagaaacaau caggaucug                                                19

<210> SEQ ID NO 126
<211> LENGTH: 19
<212> TYPE: RNA
<213> ORGANISM: Artificial
<220> FEATURE:
<223> OTHER INFORMATION: synthetic oligonucleotide

<400> SEQUENCE: 126
gacagaaaca aucaggauc                                                19

<210> SEQ ID NO 127
<211> LENGTH: 19
<212> TYPE: RNA
<213> ORGANISM: Artificial
<220> FEATURE:
<223> OTHER INFORMATION: synthetic oligonucleotide

<400> SEQUENCE: 127
uucagauccu gauuguuuc                                                19

<210> SEQ ID NO 128
<211> LENGTH: 19
<212> TYPE: RNA
<213> ORGANISM: Artificial
<220> FEATURE:
<223> OTHER INFORMATION: synthetic oligonucleotide

<400> SEQUENCE: 128 auccgauug uuucugucc                                                 19

<210> SEQ ID NO 129
<211> LENGTH: 19
<212> TYPE: RNA
<213> ORGANISM: Artificial
<220> FEATURE:
<223> OTHER INFORMATION: synthetic oligonucleotide

<400> SEQUENCE: 129
```
agauccugau uguuucugu				19

<210> SEQ ID NO 130
<211> LENGTH: 19
<212> TYPE: RNA
<213> ORGANISM: Artificial
<220> FEATURE:
<223> OTHER INFORMATION: synthetic oligonucleotide

<400> SEQUENCE: 130
ucagauccug auuguuucu				19

<210> SEQ ID NO 131
<211> LENGTH: 19
<212> TYPE: RNA
<213> ORGANISM: Artificial
<220> FEATURE:
<223> OTHER INFORMATION: synthetic oligonucleotide

<400> SEQUENCE: 131
uccugauugu uucuguccc				19

<210> SEQ ID NO 132
<211> LENGTH: 19
<212> TYPE: RNA
<213> ORGANISM: Artificial
<220> FEATURE:
<223> OTHER INFORMATION: synthetic oligonucleotide

<400> SEQUENCE: 132
cagauccuga uuguuucug				19

<210> SEQ ID NO 133
<211> LENGTH: 19
<212> TYPE: RNA
<213> ORGANISM: Artificial
<220> FEATURE:
<223> OTHER INFORMATION: synthetic oligonucleotide

<400> SEQUENCE: 133
gauccugauu guuucuguc				19

<210> SEQ ID NO 134
<211> LENGTH: 25
<212> TYPE: DNA
<213> ORGANISM: Artificial
<220> FEATURE:
<223> OTHER INFORMATION: Synthetic oligonucleotide

<400> SEQUENCE: 134
gaaacaatca ggatctgaat gcatt				25

<210> SEQ ID NO 135
<211> LENGTH: 19
<212> TYPE: DNA
<213> ORGANISM: Artificial
<220> FEATURE:
<223> OTHER INFORMATION: Synthetic oligonucleotide

<400> SEQUENCE: 135
gaaacaatca ggatctgaa				19

<210> SEQ ID NO 136
<211> LENGTH: 19
<212> TYPE: DNA
<213> ORGANISM: Artificial

<220> FEATURE:
<223> OTHER INFORMATION: Synthetic oligonucleotide

<400> SEQUENCE: 136
aaacaatcag gatctgaat                                                      19

<210> SEQ ID NO 137
<211> LENGTH: 19
<212> TYPE: DNA
<213> ORGANISM: Artificial
<220> FEATURE:
<223> OTHER INFORMATION: Synthetic oligonucleotide

<400> SEQUENCE: 137
caatcaggat ctgaatgca                                                      19

<210> SEQ ID NO 138
<211> LENGTH: 19
<212> TYPE: DNA
<213> ORGANISM: Artificial
<220> FEATURE:
<223> OTHER INFORMATION: Synthetic oligonucleotide

<400> SEQUENCE: 138
atcaggatct gaatgcatt                                                      19

<210> SEQ ID NO 139
<211> LENGTH: 19
<212> TYPE: DNA
<213> ORGANISM: Artificial
<220> FEATURE:
<223> OTHER INFORMATION: Synthetic oligonucleotide

<400> SEQUENCE: 139
acaatcagga tctgaatgc                                                      19

<210> SEQ ID NO 140
<211> LENGTH: 19
<212> TYPE: DNA
<213> ORGANISM: Artificial
<220> FEATURE:
<223> OTHER INFORMATION: Synthetic oligonucleotide

<400> SEQUENCE: 140
aatcaggatc tgaatgcat                                                      19

<210> SEQ ID NO 141
<211> LENGTH: 19
<212> TYPE: DNA
<213> ORGANISM: Artificial
<220> FEATURE:
<223> OTHER INFORMATION: Synthetic oligonucleotide

<400> SEQUENCE: 141
aacaatcagg atctgaatg                                                      19

<210> SEQ ID NO 142
<211> LENGTH: 19
<212> TYPE: RNA
<213> ORGANISM: Artificial
<220> FEATURE:
<223> OTHER INFORMATION: Synthetic oligonucleotide

<400> SEQUENCE: 142
gaaacaauca ggaucugaa                                                      19

-continued

<210> SEQ ID NO 143
<211> LENGTH: 19
<212> TYPE: RNA
<213> ORGANISM: Artificial
<220> FEATURE:
<223> OTHER INFORMATION: Synthetic oligonucleotide

<400> SEQUENCE: 143
aaacaaucag gaucugaau                                                      19

<210> SEQ ID NO 144
<211> LENGTH: 19
<212> TYPE: RNA
<213> ORGANISM: Artificial
<220> FEATURE:
<223> OTHER INFORMATION: Synthetic oligonucleotide

<400> SEQUENCE: 144
caaucaggau cugaaugca                                                      19

<210> SEQ ID NO 145
<211> LENGTH: 19
<212> TYPE: RNA
<213> ORGANISM: Artificial
<220> FEATURE:
<223> OTHER INFORMATION: Synthetic oligonucleotide

<400> SEQUENCE: 145
aucaggaucu gaaugcauu                                                      19

<210> SEQ ID NO 146
<211> LENGTH: 19
<212> TYPE: RNA
<213> ORGANISM: Artificial
<220> FEATURE:
<223> OTHER INFORMATION: Synthetic oligonucleotide

<400> SEQUENCE: 146
acaaucagga ucugaaugc                                                      19

<210> SEQ ID NO 147
<211> LENGTH: 19
<212> TYPE: RNA
<213> ORGANISM: Artificial
<220> FEATURE:
<223> OTHER INFORMATION: Synthetic oligonucleotide

<400> SEQUENCE: 147
aaucaggauc ugaaugcau                                                      19

<210> SEQ ID NO 148
<211> LENGTH: 19
<212> TYPE: RNA
<213> ORGANISM: Artificial
<220> FEATURE:
<223> OTHER INFORMATION: Synthetic oligonucleotide

<400> SEQUENCE: 148
aacaaucagg aucugaaug                                                      19

<210> SEQ ID NO 149
<211> LENGTH: 19
<212> TYPE: RNA
<213> ORGANISM: Artificial
<220> FEATURE:
<223> OTHER INFORMATION: Synthetic oligonucleotide

```
<400> SEQUENCE: 149
uucagauccu gauuguuuc                                                  19

<210> SEQ ID NO 150
<211> LENGTH: 19
<212> TYPE: RNA
<213> ORGANISM: Artificial
<220> FEATURE:
<223> OTHER INFORMATION: Synthetic oligonucleotide

<400> SEQUENCE: 150
auucagaucc ugauuguuu                                                  19

<210> SEQ ID NO 151
<211> LENGTH: 19
<212> TYPE: RNA
<213> ORGANISM: Artificial
<220> FEATURE:
<223> OTHER INFORMATION: Synthetic oligonucleotide

<400> SEQUENCE: 151
ugcauucaga uccugauug                                                  19

<210> SEQ ID NO 152
<211> LENGTH: 19
<212> TYPE: RNA
<213> ORGANISM: Artificial
<220> FEATURE:
<223> OTHER INFORMATION: Synthetic oligonucleotide

<400> SEQUENCE: 152
aaugcauuca gauccugau                                                  19

<210> SEQ ID NO 153
<211> LENGTH: 19
<212> TYPE: RNA
<213> ORGANISM: Artificial
<220> FEATURE:
<223> OTHER INFORMATION: Synthetic oligonucleotide

<400> SEQUENCE: 153
gcauucagau ccugauugu                                                  19

<210> SEQ ID NO 154
<211> LENGTH: 19
<212> TYPE: RNA
<213> ORGANISM: Artificial
<220> FEATURE:
<223> OTHER INFORMATION: Synthetic oligonucleotide

<400> SEQUENCE: 154
augcauucag auccugauu                                                  19

<210> SEQ ID NO 155
<211> LENGTH: 19
<212> TYPE: RNA
<213> ORGANISM: Artificial
<220> FEATURE:
<223> OTHER INFORMATION: Synthetic oligonucleotide

<400> SEQUENCE: 155
cauucagauc cugauuguu                                                  19

<210> SEQ ID NO 156
```

```
<211> LENGTH: 25
<212> TYPE: DNA
<213> ORGANISM: Artificial
<220> FEATURE:
<223> OTHER INFORMATION: synthetic oligonucleotide

<400> SEQUENCE: 156
caatcaggat ctgaatgcat ttgta                                          25

<210> SEQ ID NO 157
<211> LENGTH: 19
<212> TYPE: DNA
<213> ORGANISM: Artificial
<220> FEATURE:
<223> OTHER INFORMATION: synthetic oligonucleotide

<400> SEQUENCE: 157
ggatctgaat gcatttgta                                                 19

<210> SEQ ID NO 158
<211> LENGTH: 19
<212> TYPE: DNA
<213> ORGANISM: Artificial
<220> FEATURE:
<223> OTHER INFORMATION: synthetic oligonucleotide

<400> SEQUENCE: 158
caatcaggat ctgaatgca                                                 19

<210> SEQ ID NO 159
<211> LENGTH: 19
<212> TYPE: DNA
<213> ORGANISM: Artificial
<220> FEATURE:
<223> OTHER INFORMATION: synthetic oligonucleotide

<400> SEQUENCE: 159
tcaggatctg aatgcattt                                                 19

<210> SEQ ID NO 160
<211> LENGTH: 19
<212> TYPE: DNA
<213> ORGANISM: Artificial
<220> FEATURE:
<223> OTHER INFORMATION: synthetic oligonucleotide

<400> SEQUENCE: 160
atcaggatct gaatgcatt                                                 19

<210> SEQ ID NO 161
<211> LENGTH: 19
<212> TYPE: DNA
<213> ORGANISM: Artificial
<220> FEATURE:
<223> OTHER INFORMATION: synthetic oligonucleotide

<400> SEQUENCE: 161
aggatctgaa tgcatttgt                                                 19

<210> SEQ ID NO 162
<211> LENGTH: 19
<212> TYPE: DNA
<213> ORGANISM: Artificial
<220> FEATURE:
<223> OTHER INFORMATION: synthetic oligonucleotide

<400> SEQUENCE: 162
```
aatcaggatc tgaatgcat                                                19

<210> SEQ ID NO 163
<211> LENGTH: 19
<212> TYPE: DNA
<213> ORGANISM: Artificial
<220> FEATURE:
<223> OTHER INFORMATION: synthetic oligonucleotide

<400> SEQUENCE: 163
caggatctga atgcatttg                                                19

<210> SEQ ID NO 164
<211> LENGTH: 19
<212> TYPE: RNA
<213> ORGANISM: Artificial
<220> FEATURE:
<223> OTHER INFORMATION: synthetic oligonucleotide

<400> SEQUENCE: 164
ggaucugaau gcauuugua                                                19

<210> SEQ ID NO 165
<211> LENGTH: 19
<212> TYPE: RNA
<213> ORGANISM: Artificial
<220> FEATURE:
<223> OTHER INFORMATION: synthetic oligonucleotide

<400> SEQUENCE: 165
caaucaggau cugaaugca                                                19

<210> SEQ ID NO 166
<211> LENGTH: 19
<212> TYPE: RNA
<213> ORGANISM: Artificial
<220> FEATURE:
<223> OTHER INFORMATION: synthetic oligonucleotide

<400> SEQUENCE: 166
ucaggaucug aaugcauuu                                                19

<210> SEQ ID NO 167
<211> LENGTH: 19
<212> TYPE: RNA
<213> ORGANISM: Artificial
<220> FEATURE:
<223> OTHER INFORMATION: synthetic oligonucleotide

<400> SEQUENCE: 167
aucaggaucu gaaugcauu                                                19

<210> SEQ ID NO 168
<211> LENGTH: 19
<212> TYPE: RNA
<213> ORGANISM: Artificial
<220> FEATURE:
<223> OTHER INFORMATION: synthetic oligonucleotide

<400> SEQUENCE: 168
aggaucugaa ugcauuugu                                                19

<210> SEQ ID NO 169
<211> LENGTH: 19
<212> TYPE: RNA

<213> ORGANISM: Artificial
<220> FEATURE:
<223> OTHER INFORMATION: synthetic oligonucleotide

<400> SEQUENCE: 169
aaucaggauc ugaaugcau                                                   19

<210> SEQ ID NO 170
<211> LENGTH: 19
<212> TYPE: RNA
<213> ORGANISM: Artificial
<220> FEATURE:
<223> OTHER INFORMATION: synthetic oligonucleotide

<400> SEQUENCE: 170
caggaucuga augcauuug                                                   19

<210> SEQ ID NO 171
<211> LENGTH: 19
<212> TYPE: RNA
<213> ORGANISM: Artificial
<220> FEATURE:
<223> OTHER INFORMATION: synthetic oligonucleotide

<400> SEQUENCE: 171
uacaaaugca uucagaucc                                                   19

<210> SEQ ID NO 172
<211> LENGTH: 19
<212> TYPE: RNA
<213> ORGANISM: Artificial
<220> FEATURE:
<223> OTHER INFORMATION: synthetic oligonucleotide

<400> SEQUENCE: 172
ugcauucaga uccugauug                                                   19

<210> SEQ ID NO 173
<211> LENGTH: 19
<212> TYPE: RNA
<213> ORGANISM: Artificial
<220> FEATURE:
<223> OTHER INFORMATION: synthetic oligonucleotide

<400> SEQUENCE: 173
aaaugcauuc agauccuga                                                   19

<210> SEQ ID NO 174
<211> LENGTH: 19
<212> TYPE: RNA
<213> ORGANISM: Artificial
<220> FEATURE:
<223> OTHER INFORMATION: synthetic oligonucleotide

<400> SEQUENCE: 174
aaugcauuca gauccugau                                                   19

<210> SEQ ID NO 175
<211> LENGTH: 19
<212> TYPE: RNA
<213> ORGANISM: Artificial
<220> FEATURE:
<223> OTHER INFORMATION: synthetic oligonucleotide

<400> SEQUENCE: 175
acaaaugcau ucagauccu                                                   19

<210> SEQ ID NO 176
<211> LENGTH: 19
<212> TYPE: RNA
<213> ORGANISM: Artificial
<220> FEATURE:
<223> OTHER INFORMATION: synthetic oligonucleotide

<400> SEQUENCE: 176
augcauucag auccugauu                                               19

<210> SEQ ID NO 177
<211> LENGTH: 19
<212> TYPE: RNA
<213> ORGANISM: Artificial
<220> FEATURE:
<223> OTHER INFORMATION: synthetic oligonucleotide

<400> SEQUENCE: 177
caaaugcauu cagauccug                                               19

<210> SEQ ID NO 178
<211> LENGTH: 25
<212> TYPE: DNA
<213> ORGANISM: Artificial
<220> FEATURE:
<223> OTHER INFORMATION: synthetic oligonucleotide

<400> SEQUENCE: 178
gcttcaaggg tggaaaccaa ctcta                                        25

<210> SEQ ID NO 179
<211> LENGTH: 19
<212> TYPE: DNA
<213> ORGANISM: Artificial
<220> FEATURE:
<223> OTHER INFORMATION: synthetic oligonucleotide

<400> SEQUENCE: 179
cttcaagggt ggaaaccaa                                               19

<210> SEQ ID NO 180
<211> LENGTH: 19
<212> TYPE: DNA
<213> ORGANISM: Artificial
<220> FEATURE:
<223> OTHER INFORMATION: synthetic oligonucleotide

<400> SEQUENCE: 180
tcaagggtgg aaaccaact                                               19

<210> SEQ ID NO 181
<211> LENGTH: 19
<212> TYPE: DNA
<213> ORGANISM: Artificial
<220> FEATURE:
<223> OTHER INFORMATION: synthetic oligonucleotide

<400> SEQUENCE: 181
agggtggaaa ccaactcta                                               19

<210> SEQ ID NO 182
<211> LENGTH: 19
<212> TYPE: DNA
<213> ORGANISM: Artificial
<220> FEATURE:

<223> OTHER INFORMATION: synthetic oligonucleotide

<400> SEQUENCE: 182
gcttcaaggg tggaaacca                                            19

<210> SEQ ID NO 183
<211> LENGTH: 19
<212> TYPE: DNA
<213> ORGANISM: Artificial
<220> FEATURE:
<223> OTHER INFORMATION: synthetic oligonucleotide

<400> SEQUENCE: 183
caagggtgga aaccaactc                                            19

<210> SEQ ID NO 184
<211> LENGTH: 19
<212> TYPE: DNA
<213> ORGANISM: Artificial
<220> FEATURE:
<223> OTHER INFORMATION: synthetic oligonucleotide

<400> SEQUENCE: 184
aagggtggaa accaactct                                            19

<210> SEQ ID NO 185
<211> LENGTH: 19
<212> TYPE: DNA
<213> ORGANISM: Artificial
<220> FEATURE:
<223> OTHER INFORMATION: synthetic oligonucleotide

<400> SEQUENCE: 185
ttcaagggtg gaaaccaac                                            19

<210> SEQ ID NO 186
<211> LENGTH: 19
<212> TYPE: RNA
<213> ORGANISM: Artificial
<220> FEATURE:
<223> OTHER INFORMATION: synthetic oligonucleotide

<400> SEQUENCE: 186
cuucaagggu ggaaaccaa                                            19

<210> SEQ ID NO 187
<211> LENGTH: 19
<212> TYPE: RNA
<213> ORGANISM: Artificial
<220> FEATURE:
<223> OTHER INFORMATION: synthetic oligonucleotide

<400> SEQUENCE: 187
ucaagggugg aaaccaacu                                            19

<210> SEQ ID NO 188
<211> LENGTH: 19
<212> TYPE: RNA
<213> ORGANISM: Artificial
<220> FEATURE:
<223> OTHER INFORMATION: synthetic oligonucleotide

<400> SEQUENCE: 188
aggguggaaa ccaacucua                                            19

```
<210> SEQ ID NO 189
<211> LENGTH: 19
<212> TYPE: RNA
<213> ORGANISM: Artificial
<220> FEATURE:
<223> OTHER INFORMATION: synthetic oligonucleotide

<400> SEQUENCE: 189
gcuucaaggg uggaaacca                                              19

<210> SEQ ID NO 190
<211> LENGTH: 19
<212> TYPE: RNA
<213> ORGANISM: Artificial
<220> FEATURE:
<223> OTHER INFORMATION: synthetic oligonucleotide

<400> SEQUENCE: 190
caagggugga aaccaacuc                                              19

<210> SEQ ID NO 191
<211> LENGTH: 19
<212> TYPE: RNA
<213> ORGANISM: Artificial
<220> FEATURE:
<223> OTHER INFORMATION: synthetic oligonucleotide

<400> SEQUENCE: 191
aaggguggaa accaacucu                                              19

<210> SEQ ID NO 192
<211> LENGTH: 19
<212> TYPE: RNA
<213> ORGANISM: Artificial
<220> FEATURE:
<223> OTHER INFORMATION: synthetic oligonucleotide

<400> SEQUENCE: 192
uucaagggug gaaaccaac                                              19

<210> SEQ ID NO 193
<211> LENGTH: 19
<212> TYPE: RNA
<213> ORGANISM: Artificial
<220> FEATURE:
<223> OTHER INFORMATION: synthetic oligonucleotide

<400> SEQUENCE: 193
uugguuucca cccuugaag                                              19

<210> SEQ ID NO 194
<211> LENGTH: 19
<212> TYPE: RNA
<213> ORGANISM: Artificial
<220> FEATURE:
<223> OTHER INFORMATION: synthetic oligonucleotide

<400> SEQUENCE: 194
aguugguuuc cacccuuga                                              19

<210> SEQ ID NO 195
<211> LENGTH: 19
<212> TYPE: RNA
<213> ORGANISM: Artificial
<220> FEATURE:
<223> OTHER INFORMATION: synthetic oligonucleotide
```

```
<400> SEQUENCE: 195
uagaguuggu uuccacccu                                                    19

<210> SEQ ID NO 196
<211> LENGTH: 19
<212> TYPE: RNA
<213> ORGANISM: Artificial
<220> FEATURE:
<223> OTHER INFORMATION: synthetic oligonucleotide

<400> SEQUENCE: 196
ugguuuccac ccuugaagc                                                    19

<210> SEQ ID NO 197
<211> LENGTH: 19
<212> TYPE: RNA
<213> ORGANISM: Artificial
<220> FEATURE:
<223> OTHER INFORMATION: synthetic oligonucleotide

<400> SEQUENCE: 197
gaguugguuu ccacccuug                                                    19

<210> SEQ ID NO 198
<211> LENGTH: 19
<212> TYPE: RNA
<213> ORGANISM: Artificial
<220> FEATURE:
<223> OTHER INFORMATION: synthetic oligonucleotide

<400> SEQUENCE: 198
agaguugguu uccacccuu                                                    19

<210> SEQ ID NO 199
<211> LENGTH: 19
<212> TYPE: RNA
<213> ORGANISM: Artificial
<220> FEATURE:
<223> OTHER INFORMATION: synthetic oligonucleotide

<400> SEQUENCE: 199
guugguuucc acccuugaa                                                    19

<210> SEQ ID NO 200
<211> LENGTH: 25
<212> TYPE: DNA
<213> ORGANISM: Artificial
<220> FEATURE:
<223> OTHER INFORMATION: synthetic oligonucleotide

<400> SEQUENCE: 200
gaacatctgt gaagtgggaa ctata                                             25

<210> SEQ ID NO 201
<211> LENGTH: 19
<212> TYPE: DNA
<213> ORGANISM: Artificial
<220> FEATURE:
<223> OTHER INFORMATION: synthetic oligonucleotide

<400> SEQUENCE: 201
gaacatctgt gaagtggga                                                    19

<210> SEQ ID NO 202
<211> LENGTH: 19
```

```
<212> TYPE: DNA
<213> ORGANISM: Artificial
<220> FEATURE:
<223> OTHER INFORMATION: synthetic oligonucleotide

<400> SEQUENCE: 202
ctgtgaagtg ggaactata                                              19

<210> SEQ ID NO 203
<211> LENGTH: 19
<212> TYPE: DNA
<213> ORGANISM: Artificial
<220> FEATURE:
<223> OTHER INFORMATION: synthetic oligonucleotide

<400> SEQUENCE: 203
atctgtgaag tgggaacta                                              19

<210> SEQ ID NO 204
<211> LENGTH: 19
<212> TYPE: DNA
<213> ORGANISM: Artificial
<220> FEATURE:
<223> OTHER INFORMATION: synthetic oligonucleotide

<400> SEQUENCE: 204
tctgtgaagt gggaactat                                              19

<210> SEQ ID NO 205
<211> LENGTH: 19
<212> TYPE: DNA
<213> ORGANISM: Artificial
<220> FEATURE:
<223> OTHER INFORMATION: synthetic oligonucleotide

<400> SEQUENCE: 205
aacatctgtg aagtgggaa                                              19

<210> SEQ ID NO 206
<211> LENGTH: 19
<212> TYPE: DNA
<213> ORGANISM: Artificial
<220> FEATURE:
<223> OTHER INFORMATION: synthetic oligonucleotide

<400> SEQUENCE: 206
acatctgtga agtgggaac                                              19

<210> SEQ ID NO 207
<211> LENGTH: 19
<212> TYPE: DNA
<213> ORGANISM: Artificial
<220> FEATURE:
<223> OTHER INFORMATION: synthetic oligonucleotide

<400> SEQUENCE: 207
catctgtgaa gtgggaact                                              19

<210> SEQ ID NO 208
<211> LENGTH: 19
<212> TYPE: RNA
<213> ORGANISM: Artificial
<220> FEATURE:
<223> OTHER INFORMATION: synthetic oligonucleotide

<400> SEQUENCE: 208
```

```
gaacaucugu gaaguggga                                              19

<210> SEQ ID NO 209
<211> LENGTH: 19
<212> TYPE: RNA
<213> ORGANISM: Artificial
<220> FEATURE:
<223> OTHER INFORMATION: synthetic oligonucleotide

<400> SEQUENCE: 209
cugugaagug ggaacuaua                                              19

<210> SEQ ID NO 210
<211> LENGTH: 19
<212> TYPE: RNA
<213> ORGANISM: Artificial
<220> FEATURE:
<223> OTHER INFORMATION: synthetic oligonucleotide

<400> SEQUENCE: 210
aucugugaag ugggaacua                                              19

<210> SEQ ID NO 211
<211> LENGTH: 19
<212> TYPE: RNA
<213> ORGANISM: Artificial
<220> FEATURE:
<223> OTHER INFORMATION: synthetic oligonucleotide

<400> SEQUENCE: 211
ucugugaagu gggaacuau                                              19

<210> SEQ ID NO 212
<211> LENGTH: 19
<212> TYPE: RNA
<213> ORGANISM: Artificial
<220> FEATURE:
<223> OTHER INFORMATION: synthetic oligonucleotide

<400> SEQUENCE: 212
aacaucugug aagugggaa                                              19

<210> SEQ ID NO 213
<211> LENGTH: 19
<212> TYPE: RNA
<213> ORGANISM: Artificial
<220> FEATURE:
<223> OTHER INFORMATION: synthetic oligonucleotide

<400> SEQUENCE: 213
acaucuguga agugggaac                                              19

<210> SEQ ID NO 214
<211> LENGTH: 19
<212> TYPE: RNA
<213> ORGANISM: Artificial
<220> FEATURE:
<223> OTHER INFORMATION: synthetic oligonucleotide

<400> SEQUENCE: 214
caucugugaa gugggaacu                                              19

<210> SEQ ID NO 215
<211> LENGTH: 19
<212> TYPE: RNA
<213> ORGANISM: Artificial
```

```
<220> FEATURE:
<223> OTHER INFORMATION: synthetic oligonucleotide

<400> SEQUENCE: 215
ucccacuuca cagauguuc                                            19

<210> SEQ ID NO 216
<211> LENGTH: 19
<212> TYPE: RNA
<213> ORGANISM: Artificial
<220> FEATURE:
<223> OTHER INFORMATION: synthetic oligonucleotide

<400> SEQUENCE: 216
uauaguuccc acuucacag                                            19

<210> SEQ ID NO 217
<211> LENGTH: 19
<212> TYPE: RNA
<213> ORGANISM: Artificial
<220> FEATURE:
<223> OTHER INFORMATION: synthetic oligonucleotide

<400> SEQUENCE: 217
uaguucccac uucacagau                                            19

<210> SEQ ID NO 218
<211> LENGTH: 19
<212> TYPE: RNA
<213> ORGANISM: Artificial
<220> FEATURE:
<223> OTHER INFORMATION: synthetic oligonucleotide

<400> SEQUENCE: 218
auaguuccca cuucacaga                                            19

<210> SEQ ID NO 219
<211> LENGTH: 19
<212> TYPE: RNA
<213> ORGANISM: Artificial
<220> FEATURE:
<223> OTHER INFORMATION: synthetic oligonucleotide

<400> SEQUENCE: 219
uucccacuuc acagauguu                                            19

<210> SEQ ID NO 220
<211> LENGTH: 19
<212> TYPE: RNA
<213> ORGANISM: Artificial
<220> FEATURE:
<223> OTHER INFORMATION: synthetic oligonucleotide

<400> SEQUENCE: 220
guucccacuu cacagaugu                                            19

<210> SEQ ID NO 221
<211> LENGTH: 19
<212> TYPE: RNA
<213> ORGANISM: Artificial
<220> FEATURE:
<223> OTHER INFORMATION: synthetic oligonucleotide

<400> SEQUENCE: 221
aguucccacu ucacagaug                                            19
```

```
<210> SEQ ID NO 222
<211> LENGTH: 19
<212> TYPE: DNA
<213> ORGANISM: Artificial
<220> FEATURE:
<223> OTHER INFORMATION: synthetic oligonucleotide

<400> SEQUENCE: 222
gcaaacagga agatggaaa                                                19

<210> SEQ ID NO 223
<211> LENGTH: 19
<212> TYPE: RNA
<213> ORGANISM: Artificial
<220> FEATURE:
<223> OTHER INFORMATION: synthetic oligonucleotide

<400> SEQUENCE: 223
gcaaacagga agauggaaa                                                19

<210> SEQ ID NO 224
<211> LENGTH: 19
<212> TYPE: RNA
<213> ORGANISM: Artificial
<220> FEATURE:
<223> OTHER INFORMATION: synthetic oligonucleotide

<400> SEQUENCE: 224
uuuccaucuu ccuguuugc                                                19

<210> SEQ ID NO 225
<211> LENGTH: 19
<212> TYPE: DNA
<213> ORGANISM: Artificial
<220> FEATURE:
<223> OTHER INFORMATION: synthetic oligonucleotide

<400> SEQUENCE: 225
gagcagacac agacaaata                                                19

<210> SEQ ID NO 226
<211> LENGTH: 19
<212> TYPE: RNA
<213> ORGANISM: Artificial
<220> FEATURE:
<223> OTHER INFORMATION: synthetic oligonucleotide

<400> SEQUENCE: 226
gagcagacac agacaaaua                                                19

<210> SEQ ID NO 227
<211> LENGTH: 17
<212> TYPE: RNA
<213> ORGANISM: Artificial
<220> FEATURE:
<223> OTHER INFORMATION: synthetic oligonucleotide

<400> SEQUENCE: 227
uauuugucug ucugcug                                                  17

<210> SEQ ID NO 228
<211> LENGTH: 19
<212> TYPE: DNA
<213> ORGANISM: Artificial
<220> FEATURE:
<223> OTHER INFORMATION: synthetic oligonucleotide
```

```
<400> SEQUENCE: 228
ggtacaaact gcagaagat                                                19

<210> SEQ ID NO 229
<211> LENGTH: 19
<212> TYPE: RNA
<213> ORGANISM: Artificial
<220> FEATURE:
<223> OTHER INFORMATION: synthetic oligonucleotide

<400> SEQUENCE: 229
gguacaaacu gcagaagau                                                19

<210> SEQ ID NO 230
<211> LENGTH: 19
<212> TYPE: RNA
<213> ORGANISM: Artificial
<220> FEATURE:
<223> OTHER INFORMATION: synthetic oligonucleotide

<400> SEQUENCE: 230
aucuucugca guuuguacc                                                19

<210> SEQ ID NO 231
<211> LENGTH: 19
<212> TYPE: DNA
<213> ORGANISM: Artificial
<220> FEATURE:
<223> OTHER INFORMATION: synthetic oligonucleotide

<400> SEQUENCE: 231
caacaagctg tcagagaaa                                                19

<210> SEQ ID NO 232
<211> LENGTH: 19
<212> TYPE: RNA
<213> ORGANISM: Artificial
<220> FEATURE:
<223> OTHER INFORMATION: synthetic oligonucleotide

<400> SEQUENCE: 232
caacaagcug ucagagaaa                                                19

<210> SEQ ID NO 233
<211> LENGTH: 19
<212> TYPE: RNA
<213> ORGANISM: Artificial
<220> FEATURE:
<223> OTHER INFORMATION: synthetic oligonucleotide

<400> SEQUENCE: 233
uuucucuguc ugcuuguug                                                19

<210> SEQ ID NO 234
<211> LENGTH: 19
<212> TYPE: DNA
<213> ORGANISM: Artificial
<220> FEATURE:
<223> OTHER INFORMATION: synthetic oligonucleotide

<400> SEQUENCE: 234
tggagaagat gttgaaatt                                                19

<210> SEQ ID NO 235
```

```
<211> LENGTH: 19
<212> TYPE: RNA
<213> ORGANISM: Artificial
<220> FEATURE:
<223> OTHER INFORMATION: synthetic oligonucleotide

<400> SEQUENCE: 235
uggagaagau guugaaauu                                              19

<210> SEQ ID NO 236
<211> LENGTH: 19
<212> TYPE: RNA
<213> ORGANISM: Artificial
<220> FEATURE:
<223> OTHER INFORMATION: synthetic oligonucleotide

<400> SEQUENCE: 236 aauucuuca ucuucucca                                               19

<210> SEQ ID NO 237
<211> LENGTH: 19
<212> TYPE: DNA
<213> ORGANISM: Artificial
<220> FEATURE:
<223> OTHER INFORMATION: synthetic oligonucleotide

<400> SEQUENCE: 237
ctgcattgcc agaaagtta                                              19

<210> SEQ ID NO 238
<211> LENGTH: 19
<212> TYPE: RNA
<213> ORGANISM: Artificial
<220> FEATURE:
<223> OTHER INFORMATION: synthetic oligonucleotide

<400> SEQUENCE: 238
cugcauugcc agaaaguua                                              19

<210> SEQ ID NO 239
<211> LENGTH: 19
<212> TYPE: RNA
<213> ORGANISM: Artificial
<220> FEATURE:
<223> OTHER INFORMATION: synthetic oligonucleotide

<400> SEQUENCE: 239
uaacuuucug gcaaugcag                                              19

<210> SEQ ID NO 240
<211> LENGTH: 19
<212> TYPE: DNA
<213> ORGANISM: Artificial
<220> FEATURE:
<223> OTHER INFORMATION: synthetic oligonucleotide

<400> SEQUENCE: 240
gataagtact accaggaaa                                              19

<210> SEQ ID NO 241
<211> LENGTH: 19
<212> TYPE: RNA
<213> ORGANISM: Artificial
<220> FEATURE:
<223> OTHER INFORMATION: synthetic oligonucleotide

<400> SEQUENCE: 241
```
gauaaguacu accaggaaa                    19

<210> SEQ ID NO 242
<211> LENGTH: 19
<212> TYPE: RNA
<213> ORGANISM: Artificial
<220> FEATURE:
<223> OTHER INFORMATION: synthetic oligonucleotide

<400> SEQUENCE: 242
uuuccugguu guacuuauc                    19

<210> SEQ ID NO 243
<211> LENGTH: 19
<212> TYPE: DNA
<213> ORGANISM: Artificial
<220> FEATURE:
<223> OTHER INFORMATION: synthetic oligonucleotide

<400> SEQUENCE: 243
ggagaagcga caagaggaa                    19

<210> SEQ ID NO 244
<211> LENGTH: 19
<212> TYPE: RNA
<213> ORGANISM: Artificial
<220> FEATURE:
<223> OTHER INFORMATION: synthetic oligonucleotide

<400> SEQUENCE: 244
ggagaagcga caagaggaa                    19

<210> SEQ ID NO 245
<211> LENGTH: 19
<212> TYPE: RNA
<213> ORGANISM: Artificial
<220> FEATURE:
<223> OTHER INFORMATION: synthetic oligonucleotide

<400> SEQUENCE: 245
uuccucuugu cgcuucucc                    19

<210> SEQ ID NO 246
<211> LENGTH: 19
<212> TYPE: DNA
<213> ORGANISM: Artificial
<220> FEATURE:
<223> OTHER INFORMATION: synthetic oligonucleotide

<400> SEQUENCE: 246
gtgtacagtt gatgggcaa                    19

<210> SEQ ID NO 247
<211> LENGTH: 19
<212> TYPE: RNA
<213> ORGANISM: Artificial
<220> FEATURE:
<223> OTHER INFORMATION: synthetic oligonucleotide

<400> SEQUENCE: 247
guguacaguu gaugggcaa                    19

<210> SEQ ID NO 248
<211> LENGTH: 19
<212> TYPE: RNA

```
<213> ORGANISM: Artificial
<220> FEATURE:
<223> OTHER INFORMATION: synthetic oligonucleotide

<400> SEQUENCE: 248
uugcccauca acuguacac                                                   19

<210> SEQ ID NO 249
<211> LENGTH: 19
<212> TYPE: DNA
<213> ORGANISM: Artificial
<220> FEATURE:
<223> OTHER INFORMATION: synthetic oligonucleotide

<400> SEQUENCE: 249
tggtgagaac tgtgagaaa                                                   19

<210> SEQ ID NO 250
<211> LENGTH: 19
<212> TYPE: RNA
<213> ORGANISM: Artificial
<220> FEATURE:
<223> OTHER INFORMATION: synthetic oligonucleotide

<400> SEQUENCE: 250
uggugagaac ugugagaaa                                                   19

<210> SEQ ID NO 251
<211> LENGTH: 19
<212> TYPE: RNA
<213> ORGANISM: Artificial
<220> FEATURE:
<223> OTHER INFORMATION: synthetic oligonucleotide

<400> SEQUENCE: 251
uuucucacag uucucacca                                                   19

<210> SEQ ID NO 252
<211> LENGTH: 14
<212> TYPE: DNA
<213> ORGANISM: Artificial
<220> FEATURE:
<223> OTHER INFORMATION: Synthetic oligonucleotide

<400> SEQUENCE: 252
aggcatggcc agac                                                        14

<210> SEQ ID NO 253
<211> LENGTH: 14
<212> TYPE: DNA
<213> ORGANISM: Artificial
<220> FEATURE:
<223> OTHER INFORMATION: Synthetic oligonucleotide

<400> SEQUENCE: 253
aggcatgacc agac                                                        14

<210> SEQ ID NO 254
<211> LENGTH: 22
<212> TYPE: DNA
<213> ORGANISM: Artificial
<220> FEATURE:
<223> OTHER INFORMATION: Synthetic oligonucleotide

<400> SEQUENCE: 254
aagcctgctt ctgtgatcac ta                                               22
```

<210> SEQ ID NO 255
<211> LENGTH: 22
<212> TYPE: DNA
<213> ORGANISM: Artificial
<220> FEATURE:
<223> OTHER INFORMATION: Synthetic oligonucleotide

<400> SEQUENCE: 255
aagcctgttt ctgtgaccac ta                                           22

<210> SEQ ID NO 256
<211> LENGTH: 21
<212> TYPE: DNA
<213> ORGANISM: Artificial
<220> FEATURE:
<223> OTHER INFORMATION: Synthetic oligonucleotide

<400> SEQUENCE: 256
atggactcag tggaccagct g                                            21

<210> SEQ ID NO 257
<211> LENGTH: 21
<212> TYPE: DNA
<213> ORGANISM: Artificial
<220> FEATURE:
<223> OTHER INFORMATION: Synthetic oligonucleotide

<400> SEQUENCE: 257
atggactcac tggtccagct g                                            21

<210> SEQ ID NO 258
<211> LENGTH: 26
<212> TYPE: DNA
<213> ORGANISM: Artificial
<220> FEATURE:
<223> OTHER INFORMATION: Synthetic oligonucleotide

<400> SEQUENCE: 258
tgcaattctg gaacccagag cagaca                                       26

<210> SEQ ID NO 259
<211> LENGTH: 33
<212> TYPE: DNA
<213> ORGANISM: Artificial
<220> FEATURE:
<223> OTHER INFORMATION: Synthetic oligonucleotide

<400> SEQUENCE: 259
atgccccatc aactgcctcc tgggagattt tgg                               33

<210> SEQ ID NO 260
<211> LENGTH: 33
<212> TYPE: DNA
<213> ORGANISM: Artificial
<220> FEATURE:
<223> OTHER INFORMATION: Synthetic oligonucleotide

<400> SEQUENCE: 260
atgtcccatc aactgtgtcc taggagacta tgg                               33

<210> SEQ ID NO 261
<211> LENGTH: 24
<212> TYPE: DNA
<213> ORGANISM: Artificial
<220> FEATURE:

<223> OTHER INFORMATION: Synthetic oligonucleotide

<400> SEQUENCE: 261
catggtcaga ctgtgaccct tgta                          24

<210> SEQ ID NO 262
<211> LENGTH: 24
<212> TYPE: DNA
<213> ORGANISM: Artificial
<220> FEATURE:
<223> OTHER INFORMATION: Synthetic oligonucleotide

<400> SEQUENCE: 262
aaaacagtct aaagttagat ctgt                          24

<210> SEQ ID NO 263
<211> LENGTH: 24
<212> TYPE: DNA
<213> ORGANISM: Artificial
<220> FEATURE:
<223> OTHER INFORMATION: Synthetic oligonucleotide

<400> SEQUENCE: 263
aaaacaggtt aaagttagat ctgt                          24

<210> SEQ ID NO 264
<211> LENGTH: 24
<212> TYPE: DNA
<213> ORGANISM: Artificial
<220> FEATURE:
<223> OTHER INFORMATION: Synthetic oligonucleotide

<400> SEQUENCE: 264
aaaacaggtt aaagttaaat ctgt                          24

<210> SEQ ID NO 265
<211> LENGTH: 38
<212> TYPE: DNA
<213> ORGANISM: Artificial
<220> FEATURE:
<223> OTHER INFORMATION: Synthetic oligonucleotide

<400> SEQUENCE: 265
agtcagtttg ggggacagcc atgcactgcg cctctggt           38

<210> SEQ ID NO 266
<211> LENGTH: 38
<212> TYPE: DNA
<213> ORGANISM: Artificial
<220> FEATURE:
<223> OTHER INFORMATION: Synthetic oligonucleotide

<400> SEQUENCE: 266
agtcagtttg ggggacaacc atgcacagag cccctggt           38

<210> SEQ ID NO 267
<211> LENGTH: 38
<212> TYPE: DNA
<213> ORGANISM: Artificial
<220> FEATURE:
<223> OTHER INFORMATION: Synthetic oligonucleotide

<400> SEQUENCE: 267
agtcagtttg gggggcaacc atgcacagag cccctggt           38

<210> SEQ ID NO 268
<211> LENGTH: 13
<212> TYPE: DNA
<213> ORGANISM: Artificial
<220> FEATURE:
<223> OTHER INFORMATION: Synthetic oligonucleotide

<400> SEQUENCE: 268
cctttcaacc atg                                                          13

<210> SEQ ID NO 269
<211> LENGTH: 37
<212> TYPE: DNA
<213> ORGANISM: Artificial
<220> FEATURE:
<223> OTHER INFORMATION: Synthetic oligonucleotide

<400> SEQUENCE: 269
agctctgcaa aattgaagag gctgactgca agaataa                                 37

<210> SEQ ID NO 270
<211> LENGTH: 37
<212> TYPE: DNA
<213> ORGANISM: Artificial
<220> FEATURE:
<223> OTHER INFORMATION: Synthetic oligonucleotide

<400> SEQUENCE: 270
agctctgcaa aattgaagag actgattgca agaataa                                 37

<210> SEQ ID NO 271
<211> LENGTH: 37
<212> TYPE: DNA
<213> ORGANISM: Artificial
<220> FEATURE:
<223> OTHER INFORMATION: Synthetic oligonucleotide

<400> SEQUENCE: 271
agctctgcaa aattgaagag actaactgca agaataa                                 37

<210> SEQ ID NO 272
<211> LENGTH: 21
<212> TYPE: DNA
<213> ORGANISM: Artificial
<220> FEATURE:
<223> OTHER INFORMATION: Synthetic oligonucleotide

<400> SEQUENCE: 272
cgctgcattg ccagaaagtt a                                                  21

<210> SEQ ID NO 273
<211> LENGTH: 21
<212> TYPE: DNA
<213> ORGANISM: Artificial
<220> FEATURE:
<223> OTHER INFORMATION: Synthetic oligonucleotide

<400> SEQUENCE: 273
cgctgtattc ccagcaagtt a                                                  21

<210> SEQ ID NO 274
<211> LENGTH: 34
<212> TYPE: DNA
<213> ORGANISM: Artificial
<220> FEATURE:
<223> OTHER INFORMATION: Synthetic oligonucleotide

```
<400> SEQUENCE: 274
aatgcaatgg agaaaatgac tgtggagaca attc                           34

<210> SEQ ID NO 275
<211> LENGTH: 34
<212> TYPE: DNA
<213> ORGANISM: Artificial
<220> FEATURE:
<223> OTHER INFORMATION: Synthetic oligonucleotide

<400> SEQUENCE: 275
aatgcaatgg agagaatgac tgtggagaca attc                           34

<210> SEQ ID NO 276
<211> LENGTH: 24
<212> TYPE: DNA
<213> ORGANISM: Artificial
<220> FEATURE:
<223> OTHER INFORMATION: Synthetic oligonucleotide

<400> SEQUENCE: 276
gaaagggact gtgggaggac aaag                                      24

<210> SEQ ID NO 277
<211> LENGTH: 24
<212> TYPE: DNA
<213> ORGANISM: Artificial
<220> FEATURE:
<223> OTHER INFORMATION: Synthetic oligonucleotide

<400> SEQUENCE: 277
gaaaggaact gtgggaggac aaag                                      24

<210> SEQ ID NO 278
<211> LENGTH: 15
<212> TYPE: DNA
<213> ORGANISM: Artificial
<220> FEATURE:
<223> OTHER INFORMATION: Synthetic oligonucleotide

<400> SEQUENCE: 278
cagtatgcac acgga                                                15

<210> SEQ ID NO 279
<211> LENGTH: 15
<212> TYPE: DNA
<213> ORGANISM: Artificial
<220> FEATURE:
<223> OTHER INFORMATION: Synthetic oligonucleotide

<400> SEQUENCE: 279
cagtatgctc acgga                                                15

<210> SEQ ID NO 280
<211> LENGTH: 15
<212> TYPE: DNA
<213> ORGANISM: Artificial
<220> FEATURE:
<223> OTHER INFORMATION: Synthetic oligonucleotide

<400> SEQUENCE: 280
cagtgtgcac acgga                                                15

<210> SEQ ID NO 281
<211> LENGTH: 15
```

-continued

```
<212> TYPE: DNA
<213> ORGANISM: Artificial
<220> FEATURE:
<223> OTHER INFORMATION: synthetic oligonucleotide

<400> SEQUENCE: 281
cagtgtgcac acgga                                                     15

<210> SEQ ID NO 282
<211> LENGTH: 15
<212> TYPE: DNA
<213> ORGANISM: Artificial
<220> FEATURE:
<223> OTHER INFORMATION: synthetic oligonucleotide

<400> SEQUENCE: 282
cagtgtgcac acgga                                                     15

<210> SEQ ID NO 283
<211> LENGTH: 15
<212> TYPE: DNA
<213> ORGANISM: Artificial
<220> FEATURE:
<223> OTHER INFORMATION: synthetic oligonucleotide

<400> SEQUENCE: 283
cagtgtgcac acgga                                                     15

<210> SEQ ID NO 284
<211> LENGTH: 15
<212> TYPE: DNA
<213> ORGANISM: Artificial
<220> FEATURE:
<223> OTHER INFORMATION: synthetic oligonucleotide

<400> SEQUENCE: 284
cagtgtgcac acgga                                                     15

<210> SEQ ID NO 285
<211> LENGTH: 15
<212> TYPE: DNA
<213> ORGANISM: Artificial
<220> FEATURE:
<223> OTHER INFORMATION: synthetic oligonucleotide

<400> SEQUENCE: 285
cagtgtgcac acgga                                                     15

<210> SEQ ID NO 286
<211> LENGTH: 15
<212> TYPE: DNA
<213> ORGANISM: Artificial
<220> FEATURE:
<223> OTHER INFORMATION: synthetic oligonucleotide

<400> SEQUENCE: 286
cagtgtgcac acgga                                                     15

<210> SEQ ID NO 287
<211> LENGTH: 15
<212> TYPE: DNA
<213> ORGANISM: Artificial
<220> FEATURE:
<223> OTHER INFORMATION: synthetic oligonucleotide

<400> SEQUENCE: 287
```

```
cagtgtgcac acgga                                               15

<210> SEQ ID NO 288
<211> LENGTH: 15
<212> TYPE: DNA
<213> ORGANISM: Artificial
<220> FEATURE:
<223> OTHER INFORMATION: synthetic oligonucleotide

<400> SEQUENCE: 288
cagtgtgcac acgga                                               15

<210> SEQ ID NO 289
<211> LENGTH: 15
<212> TYPE: DNA
<213> ORGANISM: Artificial
<220> FEATURE:
<223> OTHER INFORMATION: synthetic oligonucleotide

<400> SEQUENCE: 289
cagtgtgcac acgga                                               15

<210> SEQ ID NO 290
<211> LENGTH: 18
<212> TYPE: DNA
<213> ORGANISM: Artificial
<220> FEATURE:
<223> OTHER INFORMATION: Synthetic oligonucleotide

<400> SEQUENCE: 290
agtgtacagt tgatgggc                                            18

<210> SEQ ID NO 291
<211> LENGTH: 18
<212> TYPE: DNA
<213> ORGANISM: Artificial
<220> FEATURE:
<223> OTHER INFORMATION: Synthetic oligonucleotide

<400> SEQUENCE: 291
agtgtgcagc tgatgggc                                            18

<210> SEQ ID NO 292
<211> LENGTH: 36
<212> TYPE: DNA
<213> ORGANISM: Artificial
<220> FEATURE:
<223> OTHER INFORMATION: Synthetic oligonucleotide

<400> SEQUENCE: 292
tgggtttcat tttctggcag gagagcccag aggaga                        36

<210> SEQ ID NO 293
<211> LENGTH: 31
<212> TYPE: DNA
<213> ORGANISM: Artificial
<220> FEATURE:
<223> OTHER INFORMATION: Synthetic oligonucleotide

<400> SEQUENCE: 293
tgataactct ttcactggag gaatatgtaa a                             31

<210> SEQ ID NO 294
<211> LENGTH: 31
<212> TYPE: DNA
<213> ORGANISM: Artificial
```

```
<220> FEATURE:
<223> OTHER INFORMATION: Synthetic oligonucleotide

<400> SEQUENCE: 294
tgataactcc ttcactggag gaatatgtaa a                              31

<210> SEQ ID NO 295
<211> LENGTH: 31
<212> TYPE: DNA
<213> ORGANISM: Artificial
<220> FEATURE:
<223> OTHER INFORMATION: Synthetic oligonucleotide

<400> SEQUENCE: 295
tgacaactct ttcactggag gaatatgtaa a                              31

<210> SEQ ID NO 296
<211> LENGTH: 34
<212> TYPE: DNA
<213> ORGANISM: Artificial
<220> FEATURE:
<223> OTHER INFORMATION: Synthetic oligonucleotide

<400> SEQUENCE: 296
tccataccgt gttccggcca atctggaaaa tgtc                           34

<210> SEQ ID NO 297
<211> LENGTH: 34
<212> TYPE: DNA
<213> ORGANISM: Artificial
<220> FEATURE:
<223> OTHER INFORMATION: Synthetic oligonucleotide

<400> SEQUENCE: 297
tccacaccga gttccagcca atctggaaaa tgtc                           34

<210> SEQ ID NO 298
<211> LENGTH: 34
<212> TYPE: DNA
<213> ORGANISM: Artificial
<220> FEATURE:
<223> OTHER INFORMATION: Synthetic oligonucleotide

<400> SEQUENCE: 298
tccataccgt gtttcagcca atctggaaaa tgtc                           34

<210> SEQ ID NO 299
<211> LENGTH: 24
<212> TYPE: DNA
<213> ORGANISM: Artificial
<220> FEATURE:
<223> OTHER INFORMATION: Synthetic oligonucleotide

<400> SEQUENCE: 299
ctttgaggta caaactgcag aaga                                      24

<210> SEQ ID NO 300
<211> LENGTH: 24
<212> TYPE: DNA
<213> ORGANISM: Artificial
<220> FEATURE:
<223> OTHER INFORMATION: Synthetic oligonucleotide

<400> SEQUENCE: 300
ctttgaggta caaactatag aaga                                      24
```

```
<210> SEQ ID NO 301
<211> LENGTH: 24
<212> TYPE: DNA
<213> ORGANISM: Artificial
<220> FEATURE:
<223> OTHER INFORMATION: Synthetic oligonucleotide

<400> SEQUENCE: 301
ctttgaggta caaactatag aaga                                          24

<210> SEQ ID NO 302
<211> LENGTH: 25
<212> TYPE: DNA
<213> ORGANISM: Artificial
<220> FEATURE:
<223> OTHER INFORMATION: Synthetic oligonucleotide

<400> SEQUENCE: 302
tgacttgaaa acagatttct acaag                                         25

<210> SEQ ID NO 303
<211> LENGTH: 25
<212> TYPE: DNA
<213> ORGANISM: Artificial
<220> FEATURE:
<223> OTHER INFORMATION: Synthetic oligonucleotide

<400> SEQUENCE: 303
tgacttgaaa acagaattct acaag                                         25

<210> SEQ ID NO 304
<211> LENGTH: 20
<212> TYPE: DNA
<213> ORGANISM: Artificial
<220> FEATURE:
<223> OTHER INFORMATION: Synthetic oligonucleotide

<400> SEQUENCE: 304
taccaatttt ttattcctca                                               20

<210> SEQ ID NO 305
<211> LENGTH: 20
<212> TYPE: DNA
<213> ORGANISM: Artificial
<220> FEATURE:
<223> OTHER INFORMATION: Synthetic oligonucleotide

<400> SEQUENCE: 305
taccaatttt ttattcctca                                               20

<210> SEQ ID NO 306
<211> LENGTH: 20
<212> TYPE: DNA
<213> ORGANISM: Artificial
<220> FEATURE:
<223> OTHER INFORMATION: Synthetic oligonucleotide

<400> SEQUENCE: 306
taccaatttt ccatttctca                                               20

<210> SEQ ID NO 307
<211> LENGTH: 18
<212> TYPE: DNA
<213> ORGANISM: Artificial
<220> FEATURE:
<223> OTHER INFORMATION: Synthetic oligonucleotide
```

-continued

<400> SEQUENCE: 307
cattcaagcc tctcacaa                                                   18

<210> SEQ ID NO 308
<211> LENGTH: 18
<212> TYPE: DNA
<213> ORGANISM: Artificial
<220> FEATURE:
<223> OTHER INFORMATION: Synthetic oligonucleotide

<400> SEQUENCE: 308
cattgaagcc tcccacaa                                                   18

<210> SEQ ID NO 309
<211> LENGTH: 18
<212> TYPE: DNA
<213> ORGANISM: Artificial
<220> FEATURE:
<223> OTHER INFORMATION: Synthetic oligonucleotide

<400> SEQUENCE: 309
cattaaagct tcccacaa                                                   18

<210> SEQ ID NO 310
<211> LENGTH: 37
<212> TYPE: DNA
<213> ORGANISM: Artificial
<220> FEATURE:
<223> OTHER INFORMATION: Synthetic oligonucleotide

<400> SEQUENCE: 310
aggatccata aagtgatgaa agtcttaaac ttcacaa                              37

<210> SEQ ID NO 311
<211> LENGTH: 37
<212> TYPE: DNA
<213> ORGANISM: Artificial
<220> FEATURE:
<223> OTHER INFORMATION: Synthetic oligonucleotide

<400> SEQUENCE: 311
aggatccata aagtgataaa agtcttaaac ttcacaa                              37

<210> SEQ ID NO 312
<211> LENGTH: 37
<212> TYPE: DNA
<213> ORGANISM: Artificial
<220> FEATURE:
<223> OTHER INFORMATION: Synthetic oligonucleotide

<400> SEQUENCE: 312
aggatccata agctgataaa agtcttaaac ttcacaa                              37

<210> SEQ ID NO 313
<211> LENGTH: 11
<212> TYPE: DNA
<213> ORGANISM: Artificial
<220> FEATURE:
<223> OTHER INFORMATION: Synthetic oligonucleotide

<400> SEQUENCE: 313
ctgcctctag a                                                          11

<210> SEQ ID NO 314

-continued

```
<211> LENGTH: 11
<212> TYPE: DNA
<213> ORGANISM: Artificial
<220> FEATURE:
<223> OTHER INFORMATION: Synthetic oligonucleotide

<400> SEQUENCE: 314
ctgcctttag a                                                              11

<210> SEQ ID NO 315
<211> LENGTH: 24
<212> TYPE: DNA
<213> ORGANISM: Artificial
<220> FEATURE:
<223> OTHER INFORMATION: Synthetic oligonucleotide

<400> SEQUENCE: 315
atacaactct gctttgtaca gccg                                                24

<210> SEQ ID NO 316
<211> LENGTH: 24
<212> TYPE: DNA
<213> ORGANISM: Artificial
<220> FEATURE:
<223> OTHER INFORMATION: Synthetic oligonucleotide

<400> SEQUENCE: 316
atacaacttt gctttgtaca gccg                                                24

<210> SEQ ID NO 317
<211> LENGTH: 24
<212> TYPE: DNA
<213> ORGANISM: Artificial
<220> FEATURE:
<223> OTHER INFORMATION: Synthetic oligonucleotide

<400> SEQUENCE: 317
atacaactct gctgtgtaca gccg                                                24

<210> SEQ ID NO 318
<211> LENGTH: 20
<212> TYPE: DNA
<213> ORGANISM: Artificial
<220> FEATURE:
<223> OTHER INFORMATION: Synthetic oligonucleotide

<400> SEQUENCE: 318
atattcgatg actttgggac                                                     20

<210> SEQ ID NO 319
<211> LENGTH: 20
<212> TYPE: DNA
<213> ORGANISM: Artificial
<220> FEATURE:
<223> OTHER INFORMATION: Synthetic oligonucleotide

<400> SEQUENCE: 319
atatttgatg actttgggac                                                     20

<210> SEQ ID NO 320
<211> LENGTH: 20
<212> TYPE: DNA
<213> ORGANISM: Artificial
<220> FEATURE:
<223> OTHER INFORMATION: Synthetic oligonucleotide

<400> SEQUENCE: 320
```
atatttgatg acttcgggac        20

<210> SEQ ID NO 321
<211> LENGTH: 27
<212> TYPE: DNA
<213> ORGANISM: Artificial
<220> FEATURE:
<223> OTHER INFORMATION: Synthetic oligonucleotide

<400> SEQUENCE: 321
ggctccctgg gaggcgtgta tgacctt        27

<210> SEQ ID NO 322
<211> LENGTH: 27
<212> TYPE: DNA
<213> ORGANISM: Artificial
<220> FEATURE:
<223> OTHER INFORMATION: Synthetic oligonucleotide

<400> SEQUENCE: 322
ggctcccttg ggggcaagta tgacctt        27

<210> SEQ ID NO 323
<211> LENGTH: 22
<212> TYPE: DNA
<213> ORGANISM: Artificial
<220> FEATURE:
<223> OTHER INFORMATION: Synthetic oligonucleotide

<400> SEQUENCE: 323
ctcaggttta accgaggaag aa        22

<210> SEQ ID NO 324
<211> LENGTH: 22
<212> TYPE: DNA
<213> ORGANISM: Artificial
<220> FEATURE:
<223> OTHER INFORMATION: Synthetic oligonucleotide

<400> SEQUENCE: 324
ctcaggttta acagaagaag aa        22

<210> SEQ ID NO 325
<211> LENGTH: 27
<212> TYPE: DNA
<213> ORGANISM: Artificial
<220> FEATURE:
<223> OTHER INFORMATION: Synthetic oligonucleotide

<400> SEQUENCE: 325
actgtgtcag gattgaaaca aagaaac        27

<210> SEQ ID NO 326
<211> LENGTH: 27
<212> TYPE: DNA
<213> ORGANISM: Artificial
<220> FEATURE:
<223> OTHER INFORMATION: Synthetic oligonucleotide

<400> SEQUENCE: 326
actgtgtccg gtatgaaaca aagaaac        27

<210> SEQ ID NO 327
<211> LENGTH: 27
<212> TYPE: DNA

```
<213> ORGANISM: Artificial
<220> FEATURE:
<223> OTHER INFORMATION: Synthetic oligonucleotide

<400> SEQUENCE: 327
actgtgtcca gtatgaaaca aagaaac                                            27

<210> SEQ ID NO 328
<211> LENGTH: 19
<212> TYPE: DNA
<213> ORGANISM: Artificial
<220> FEATURE:
<223> OTHER INFORMATION: Synthetic oligonucleotide

<400> SEQUENCE: 328
aggttcattt atacaggga                                                     19

<210> SEQ ID NO 329
<211> LENGTH: 19
<212> TYPE: DNA
<213> ORGANISM: Artificial
<220> FEATURE:
<223> OTHER INFORMATION: Synthetic oligonucleotide

<400> SEQUENCE: 329
aggttccttt ttacaggga                                                     19

<210> SEQ ID NO 330
<211> LENGTH: 19
<212> TYPE: DNA
<213> ORGANISM: Artificial
<220> FEATURE:
<223> OTHER INFORMATION: Synthetic oligonucleotide

<400> SEQUENCE: 330
aggttccttt ttgcaggga                                                     19

<210> SEQ ID NO 331
<211> LENGTH: 18
<212> TYPE: DNA
<213> ORGANISM: Artificial
<220> FEATURE:
<223> OTHER INFORMATION: Synthetic oligonucleotide

<400> SEQUENCE: 331
gagaaatcca tatccctg                                                      18

<210> SEQ ID NO 332
<211> LENGTH: 18
<212> TYPE: DNA
<213> ORGANISM: Artificial
<220> FEATURE:
<223> OTHER INFORMATION: Synthetic oligonucleotide

<400> SEQUENCE: 332
gagaaatcta tatccctg                                                      18

<210> SEQ ID NO 333
<211> LENGTH: 18
<212> TYPE: DNA
<213> ORGANISM: Artificial
<220> FEATURE:
<223> OTHER INFORMATION: Synthetic oligonucleotide

<400> SEQUENCE: 333
gagaaatcca tttccctg                                                      18
```

```
<210> SEQ ID NO 334
<211> LENGTH: 18
<212> TYPE: DNA
<213> ORGANISM: Artificial
<220> FEATURE:
<223> OTHER INFORMATION: Synthetic oligonucleotide

<400> SEQUENCE: 334
gagaaatcca tttccctg                                                 18

<210> SEQ ID NO 335
<211> LENGTH: 18
<212> TYPE: DNA
<213> ORGANISM: Artificial
<220> FEATURE:
<223> OTHER INFORMATION: Synthetic oligonucleotide

<400> SEQUENCE: 335
gagaaatcca tttccctg                                                 18

<210> SEQ ID NO 336
<211> LENGTH: 18
<212> TYPE: DNA
<213> ORGANISM: Artificial
<220> FEATURE:
<223> OTHER INFORMATION: synthetic nucleic acid

<400> SEQUENCE: 336
gagaaatcca tttccctg                                                 18

<210> SEQ ID NO 337
<211> LENGTH: 21
<212> TYPE: DNA
<213> ORGANISM: Artificial
<220> FEATURE:
<223> OTHER INFORMATION: Synthetic oligonucleotide

<400> SEQUENCE: 337
agcagctttg gcatgggaga a                                             21

<210> SEQ ID NO 338
<211> LENGTH: 21
<212> TYPE: DNA
<213> ORGANISM: Artificial
<220> FEATURE:
<223> OTHER INFORMATION: Synthetic oligonucleotide

<400> SEQUENCE: 338
agcagccttg gcttgggaga a                                             21

<210> SEQ ID NO 339
<211> LENGTH: 18
<212> TYPE: DNA
<213> ORGANISM: Artificial
<220> FEATURE:
<223> OTHER INFORMATION: Synthetic oligonucleotide

<400> SEQUENCE: 339
ctctggtctg gaggagaa                                                 18

<210> SEQ ID NO 340
<211> LENGTH: 18
<212> TYPE: DNA
<213> ORGANISM: Artificial
<220> FEATURE:
```

<223> OTHER INFORMATION: Synthetic oligonucleotide

<400> SEQUENCE: 340
ctctggtcca gaggcgaa                        18

<210> SEQ ID NO 341
<211> LENGTH: 18
<212> TYPE: DNA
<213> ORGANISM: Artificial
<220> FEATURE:
<223> OTHER INFORMATION: Synthetic oligonucleotide

<400> SEQUENCE: 341
ctctggtcca gaggagaa                        18

<210> SEQ ID NO 342
<211> LENGTH: 29
<212> TYPE: DNA
<213> ORGANISM: Artificial
<220> FEATURE:
<223> OTHER INFORMATION: Synthetic oligonucleotide

<400> SEQUENCE: 342
tctgagtggt tagaatcagt gaaggaaaa            29

<210> SEQ ID NO 343
<211> LENGTH: 29
<212> TYPE: DNA
<213> ORGANISM: Artificial
<220> FEATURE:
<223> OTHER INFORMATION: Synthetic oligonucleotide

<400> SEQUENCE: 343
tctgagtggt tagagtcggt gaaggaaaa            29

<210> SEQ ID NO 344
<211> LENGTH: 29
<212> TYPE: DNA
<213> ORGANISM: Artificial
<220> FEATURE:
<223> OTHER INFORMATION: Synthetic oligonucleotide

<400> SEQUENCE: 344
tctgagtggc tagaatcggt gaaggaaaa            29

<210> SEQ ID NO 345
<211> LENGTH: 14
<212> TYPE: DNA
<213> ORGANISM: Artificial
<220> FEATURE:
<223> OTHER INFORMATION: Synthetic oligonucleotide

<400> SEQUENCE: 345
cctgctgtga ttga                            14

<210> SEQ ID NO 346
<211> LENGTH: 14
<212> TYPE: DNA
<213> ORGANISM: Artificial
<220> FEATURE:
<223> OTHER INFORMATION: Synthetic oligonucleotide

<400> SEQUENCE: 346
cctgctgtgg ttga                            14

```
<210> SEQ ID NO 347
<211> LENGTH: 14
<212> TYPE: DNA
<213> ORGANISM: Artificial
<220> FEATURE:
<223> OTHER INFORMATION: Synthetic oligonucleotide

<400> SEQUENCE: 347
cctgctgtag ttga                                                       14

<210> SEQ ID NO 348
<211> LENGTH: 20
<212> TYPE: DNA
<213> ORGANISM: Artificial
<220> FEATURE:
<223> OTHER INFORMATION: Synthetic oligonucleotide

<400> SEQUENCE: 348
gacttggtaa gaaacatccc                                                 20

<210> SEQ ID NO 349
<211> LENGTH: 20
<212> TYPE: DNA
<213> ORGANISM: Artificial
<220> FEATURE:
<223> OTHER INFORMATION: Synthetic oligonucleotide

<400> SEQUENCE: 349
gacttggtca gaaacatccc                                                 20

<210> SEQ ID NO 350
<211> LENGTH: 29
<212> TYPE: DNA
<213> ORGANISM: Artificial
<220> FEATURE:
<223> OTHER INFORMATION: Synthetic oligonucleotide

<400> SEQUENCE: 350
tgtgcagtga caaaacggaa caacctcag                                       29

<210> SEQ ID NO 351
<211> LENGTH: 20
<212> TYPE: DNA
<213> ORGANISM: Artificial
<220> FEATURE:
<223> OTHER INFORMATION: synthetic oligonucleotide

<400> SEQUENCE: 351
caagagtatg cagccaagtt                                                 20

<210> SEQ ID NO 352
<211> LENGTH: 20
<212> TYPE: DNA
<213> ORGANISM: Artificial
<220> FEATURE:
<223> OTHER INFORMATION: synthetic oligonucleotide

<400> SEQUENCE: 352
caagaatatg cagccaagtt                                                 20

<210> SEQ ID NO 353
<211> LENGTH: 20
<212> TYPE: DNA
<213> ORGANISM: Artificial
<220> FEATURE:
<223> OTHER INFORMATION: synthetic oligonucleotide
```

<400> SEQUENCE: 353
ccttgccagt gtgctccatg                                               20

<210> SEQ ID NO 354
<211> LENGTH: 20
<212> TYPE: DNA
<213> ORGANISM: Artificial
<220> FEATURE:
<223> OTHER INFORMATION: synthetic oligonucleotide

<400> SEQUENCE: 354
ccttgccaat gtgctccatg                                               20

<210> SEQ ID NO 355
<211> LENGTH: 14
<212> TYPE: DNA
<213> ORGANISM: Artificial
<220> FEATURE:
<223> OTHER INFORMATION: synthetic oligonucleotide

<400> SEQUENCE: 355
taatggccga ccca                                                     14

<210> SEQ ID NO 356
<211> LENGTH: 14
<212> TYPE: DNA
<213> ORGANISM: Artificial
<220> FEATURE:
<223> OTHER INFORMATION: synthetic oligonucleotide

<400> SEQUENCE: 356
taatggccgc ccca                                                     14

<210> SEQ ID NO 357
<211> LENGTH: 17
<212> TYPE: DNA
<213> ORGANISM: Artificial
<220> FEATURE:
<223> OTHER INFORMATION: synthetic oligonucleotide

<400> SEQUENCE: 357
ctctcaggga ctgaatg                                                  17

<210> SEQ ID NO 358
<211> LENGTH: 17
<212> TYPE: DNA
<213> ORGANISM: Artificial
<220> FEATURE:
<223> OTHER INFORMATION: synthetic oligonucleotide

<400> SEQUENCE: 358
ctctcaggca cagaatg                                                  17

<210> SEQ ID NO 359
<211> LENGTH: 25
<212> TYPE: DNA
<213> ORGANISM: Artificial
<220> FEATURE:
<223> OTHER INFORMATION: synthetic oligonucleotide

<400> SEQUENCE: 359
tgtgtgtgtg tcagagtggc accta                                         25

<210> SEQ ID NO 360
<211> LENGTH: 25

```
<212> TYPE: DNA
<213> ORGANISM: Artificial
<220> FEATURE:
<223> OTHER INFORMATION: synthetic oligonucleotide

<400> SEQUENCE: 360
tgtgtgtgtg ccagagtggt accta                                     25

<210> SEQ ID NO 361
<211> LENGTH: 25
<212> TYPE: DNA
<213> ORGANISM: Artificial
<220> FEATURE:
<223> OTHER INFORMATION: synthetic oligonucleotide

<400> SEQUENCE: 361
tgtgtgtgtg ccagagcggc accta                                     25

<210> SEQ ID NO 362
<211> LENGTH: 14
<212> TYPE: DNA
<213> ORGANISM: Artificial
<220> FEATURE:
<223> OTHER INFORMATION: synthetic oligonucleotide

<400> SEQUENCE: 362
ggtgagaact gtga                                                 14

<210> SEQ ID NO 363
<211> LENGTH: 18
<212> TYPE: DNA
<213> ORGANISM: Artificial
<220> FEATURE:
<223> OTHER INFORMATION: synthetic oligonucleotide

<400> SEQUENCE: 363
ttataaatcc aatgcagt                                             18

<210> SEQ ID NO 364
<211> LENGTH: 18
<212> TYPE: DNA
<213> ORGANISM: Artificial
<220> FEATURE:
<223> OTHER INFORMATION: synthetic oligonucleotide

<400> SEQUENCE: 364
ttataaatcg aatgcagt                                             18

<210> SEQ ID NO 365
<211> LENGTH: 18
<212> TYPE: DNA
<213> ORGANISM: Artificial
<220> FEATURE:
<223> OTHER INFORMATION: synthetic oligonucleotide

<400> SEQUENCE: 365
ttacaaatct gatgcagt                                             18

<210> SEQ ID NO 366
<211> LENGTH: 21
<212> TYPE: DNA
<213> ORGANISM: Artificial
<220> FEATURE:
<223> OTHER INFORMATION: synthetic oligonucleotide

<400> SEQUENCE: 366
```
gggttgttgg tcttcctgga g          21

<210> SEQ ID NO 367
<211> LENGTH: 21
<212> TYPE: DNA
<213> ORGANISM: Artificial
<220> FEATURE:
<223> OTHER INFORMATION: synthetic oligonucleotide

<400> SEQUENCE: 367
gggctgctgg tcttcctgga g          21

<210> SEQ ID NO 368
<211> LENGTH: 17
<212> TYPE: DNA
<213> ORGANISM: Artificial
<220> FEATURE:
<223> OTHER INFORMATION: synthetic oligonucleotide

<400> SEQUENCE: 368
gatgctactt ataagag               17

<210> SEQ ID NO 369
<211> LENGTH: 17
<212> TYPE: DNA
<213> ORGANISM: Artificial
<220> FEATURE:
<223> OTHER INFORMATION: synthetic oligonucleotide

<400> SEQUENCE: 369
aatgctgctt ataggag               17

<210> SEQ ID NO 370
<211> LENGTH: 19
<212> TYPE: DNA
<213> ORGANISM: Artificial
<220> FEATURE:
<223> OTHER INFORMATION: synthetic oligonucleotide

<400> SEQUENCE: 370
cgaggaggga aacgctgtg             19

<210> SEQ ID NO 371
<211> LENGTH: 19
<212> TYPE: DNA
<213> ORGANISM: Artificial
<220> FEATURE:
<223> OTHER INFORMATION: synthetic oligonucleotide

<400> SEQUENCE: 371
cgaggagggc agcgctgtg             19

<210> SEQ ID NO 372
<211> LENGTH: 19
<212> TYPE: DNA
<213> ORGANISM: Artificial
<220> FEATURE:
<223> OTHER INFORMATION: synthetic oligonucleotide

<400> SEQUENCE: 372
cgaggaggac aaagctgtg             19

<210> SEQ ID NO 373
<211> LENGTH: 20
<212> TYPE: DNA
<213> ORGANISM: Artificial

```
<220> FEATURE:
<223> OTHER INFORMATION: synthetic oligonucleotide

<400> SEQUENCE: 373
gaagactgca cattttcaat                                              20

<210> SEQ ID NO 374
<211> LENGTH: 20
<212> TYPE: DNA
<213> ORGANISM: Artificial
<220> FEATURE:
<223> OTHER INFORMATION: synthetic oligonucleotide

<400> SEQUENCE: 374
gaagactgta cattctcaat                                              20

<210> SEQ ID NO 375
<211> LENGTH: 20
<212> TYPE: DNA
<213> ORGANISM: Artificial
<220> FEATURE:
<223> OTHER INFORMATION: synthetic oligonucleotide

<400> SEQUENCE: 375
gaagactgta cagtctcaat                                              20

<210> SEQ ID NO 376
<211> LENGTH: 33
<212> TYPE: DNA
<213> ORGANISM: Artificial
<220> FEATURE:
<223> OTHER INFORMATION: synthetic oligonucleotide

<400> SEQUENCE: 376
tggacaacca tgtatcaatg atgatgaaga aat                               33

<210> SEQ ID NO 377
<211> LENGTH: 33
<212> TYPE: DNA
<213> ORGANISM: Artificial
<220> FEATURE:
<223> OTHER INFORMATION: synthetic oligonucleotide

<400> SEQUENCE: 377
tggacaaccg tgcatcagtg atgatgaaga aat                               33

<210> SEQ ID NO 378
<211> LENGTH: 19
<212> TYPE: DNA
<213> ORGANISM: Artificial
<220> FEATURE:
<223> OTHER INFORMATION: synthetic oligonucleotide

<400> SEQUENCE: 378
agaagcagat tccgggtgt                                               19

<210> SEQ ID NO 379
<211> LENGTH: 19
<212> TYPE: DNA
<213> ORGANISM: Artificial
<220> FEATURE:
<223> OTHER INFORMATION: synthetic oligonucleotide

<400> SEQUENCE: 379
agaagcagat tcagggtgt                                               19
```

```
<210> SEQ ID NO 380
<211> LENGTH: 19
<212> TYPE: DNA
<213> ORGANISM: Artificial
<220> FEATURE:
<223> OTHER INFORMATION: synthetic oligonucleotide

<400> SEQUENCE: 380
agaagcagaa tcagggtgt                                                    19

<210> SEQ ID NO 381
<211> LENGTH: 21
<212> TYPE: DNA
<213> ORGANISM: Artificial
<220> FEATURE:
<223> OTHER INFORMATION: synthetic oligonucleotide

<400> SEQUENCE: 381
ggaatgaaaa gcaactatac t                                                 21

<210> SEQ ID NO 382
<211> LENGTH: 21
<212> TYPE: DNA
<213> ORGANISM: Artificial
<220> FEATURE:
<223> OTHER INFORMATION: synthetic oligonucleotide

<400> SEQUENCE: 382
ggaatgaaaa gaaactgtac t                                                 21

<210> SEQ ID NO 383
<211> LENGTH: 21
<212> TYPE: DNA
<213> ORGANISM: Artificial
<220> FEATURE:
<223> OTHER INFORMATION: synthetic oligonucleotide

<400> SEQUENCE: 383
ggaatgagaa gaaactgtac t                                                 21

<210> SEQ ID NO 384
<211> LENGTH: 24
<212> TYPE: DNA
<213> ORGANISM: Artificial
<220> FEATURE:
<223> OTHER INFORMATION: synthetic oligonucleotide

<400> SEQUENCE: 384
tgaaatttca tgccttactg gctt                                              24

<210> SEQ ID NO 385
<211> LENGTH: 24
<212> TYPE: DNA
<213> ORGANISM: Artificial
<220> FEATURE:
<223> OTHER INFORMATION: synthetic oligonucleotide

<400> SEQUENCE: 385
tgaaatttca tgtctcactg gatt                                              24

<210> SEQ ID NO 386
<211> LENGTH: 24
<212> TYPE: DNA
<213> ORGANISM: Artificial
<220> FEATURE:
<223> OTHER INFORMATION: synthetic oligonucleotide
```

```
<400> SEQUENCE: 386
tgaaatttca tgtcttactg gatt                                            24

<210> SEQ ID NO 387
<211> LENGTH: 21
<212> TYPE: DNA
<213> ORGANISM: Artificial
<220> FEATURE:
<223> OTHER INFORMATION: synthetic oligonucleotide

<400> SEQUENCE: 387
ccagtacttc agatgcttac c                                               21

<210> SEQ ID NO 388
<211> LENGTH: 21
<212> TYPE: DNA
<213> ORGANISM: Artificial
<220> FEATURE:
<223> OTHER INFORMATION: synthetic oligonucleotide

<400> SEQUENCE: 388
ccagtacttg agatgtttac c                                               21

<210> SEQ ID NO 389
<211> LENGTH: 30
<212> TYPE: DNA
<213> ORGANISM: Artificial
<220> FEATURE:
<223> OTHER INFORMATION: synthetic oligonucleotide

<400> SEQUENCE: 389
acctggagac aagggatgt ggaatgccaa                                      30

<210> SEQ ID NO 390
<211> LENGTH: 30
<212> TYPE: DNA
<213> ORGANISM: Artificial
<220> FEATURE:
<223> OTHER INFORMATION: synthetic oligonucleotide

<400> SEQUENCE: 390
acctggaggc aagggatgt cgaatgccaa                                      30

<210> SEQ ID NO 391
<211> LENGTH: 30
<212> TYPE: DNA
<213> ORGANISM: Artificial
<220> FEATURE:
<223> OTHER INFORMATION: synthetic oligonucleotide

<400> SEQUENCE: 391
acctggagtc aaggagatgt ggaatgccaa                                      30

<210> SEQ ID NO 392
<211> LENGTH: 26
<212> TYPE: DNA
<213> ORGANISM: Artificial
<220> FEATURE:
<223> OTHER INFORMATION: synthetic oligonucleotide

<400> SEQUENCE: 392
gtcctgacaa ttacaccatt tcagag                                          26

<210> SEQ ID NO 393
```

```
<211> LENGTH: 26
<212> TYPE: DNA
<213> ORGANISM: Artificial
<220> FEATURE:
<223> OTHER INFORMATION: synthetic oligonucleotide

<400> SEQUENCE: 393
gtcctgacca tctccccatt tcagag                                        26

<210> SEQ ID NO 394
<211> LENGTH: 20
<212> TYPE: DNA
<213> ORGANISM: Artificial
<220> FEATURE:
<223> OTHER INFORMATION: synthetic oligonucleotide

<400> SEQUENCE: 394
attggtgaat ccattgagct                                               20

<210> SEQ ID NO 395
<211> LENGTH: 20
<212> TYPE: DNA
<213> ORGANISM: Artificial
<220> FEATURE:
<223> OTHER INFORMATION: synthetic oligonucleotide

<400> SEQUENCE: 395
attggggaat ccattgagct                                               20

<210> SEQ ID NO 396
<211> LENGTH: 37
<212> TYPE: DNA
<213> ORGANISM: Artificial
<220> FEATURE:
<223> OTHER INFORMATION: synthetic oligonucleotide

<400> SEQUENCE: 396
aggctttgtt gttgctgggc catcaaggta cacatgc                            37

<210> SEQ ID NO 397
<211> LENGTH: 37
<212> TYPE: DNA
<213> ORGANISM: Artificial
<220> FEATURE:
<223> OTHER INFORMATION: synthetic oligonucleotide

<400> SEQUENCE: 397
aggctttgtt gttgctggcc catcgaggta tacatgc                            37

<210> SEQ ID NO 398
<211> LENGTH: 37
<212> TYPE: DNA
<213> ORGANISM: Artificial
<220> FEATURE:
<223> OTHER INFORMATION: synthetic oligonucleotide

<400> SEQUENCE: 398
aggctttgtt gttgctggac catcaaggta tacatgc                            37

<210> SEQ ID NO 399
<211> LENGTH: 23
<212> TYPE: DNA
<213> ORGANISM: Artificial
<220> FEATURE:
<223> OTHER INFORMATION: synthetic oligonucleotide

<400> SEQUENCE: 399
```
tcctggacac cacccatttc aaa                                            23

<210> SEQ ID NO 400
<211> LENGTH: 23
<212> TYPE: DNA
<213> ORGANISM: Artificial
<220> FEATURE:
<223> OTHER INFORMATION: synthetic oligonucleotide

<400> SEQUENCE: 400
tcctggacac ctcccattcc aaa                                            23

<210> SEQ ID NO 401
<211> LENGTH: 23
<212> TYPE: DNA
<213> ORGANISM: Artificial
<220> FEATURE:
<223> OTHER INFORMATION: synthetic oligonucleotide

<400> SEQUENCE: 401
tcctggacac ctcccatttc aaa                                            23

<210> SEQ ID NO 402
<211> LENGTH: 3038
<212> TYPE: DNA
<213> ORGANISM: Rat

<400> SEQUENCE: 402
aggcatgacc agacatctca ccttgtgttt cattttgctg atcatactga ttgacaagag      60
tgaagcctgt ttctgtgacc actacccatg gactcactgg tccagctgtt ctaagtcctg     120
caattctgga acccagagca gacagagaca atcgtagtg aacgattact atcgggataa     180
ctcatgcgat cagctctgta ccaagcagga gaccagacag tgcaacgtgg agacatgtcc     240
catcaactgt gtcctaggag actatggaac atggtcagac tgtgacccctt gtattagaaa     300 acaggttaaa gttagatctg ttctgcgccc aagtcagttt gggggacaac catgcacaga     360 gccctggtg acctttcaac catgtgtccc atctgagctc tgcaaaattg aagagactga     420
ttgcaagaat aaattcctct gtgacagtgg gcgctgtatt cccagcaagt taaaatgcaa     480
tggagaaaat gactgtggag acaattcaga cgaaaggaac tgtgggagga caaagccagt     540
atgctcacgg acatacactc ctatcccag tgtgcagctg atgggcgctg ggtttcattt     600
tctggcagga gagcccagag agatgtccc tgataactcc ttcactggag aatatgtaa     660 atccgtcagg agcagccgaa cgagtaatcc acaccgagtt ccagccaatc tggaaaatgt     720
caactttgag gtacaaacta tagaagatga cttgaaaaca gatttctaca aggatttagc     780
cactattgga aaaaataaaa atgaagaccg ttcattgtct ggtgagaaga agactcttt     840 ctacgtacca atttttatt cctcaaagaa aagtgaaaat ttccaacgta actcaggctt     900
caaaaacgcc attgaagcct cccacaagaa ggattcgagc tttgttagga tccataaagt     960
gataaaagtc ttaaacttca caatgaaaac gacagacctg cagctctcag acgtcttcct    1020
aaaagccctc atccacctgc ctttagaata caactttgct ttgtacagcc ggatatttga    1080
tgactttggg acccactatt tcacctcagg ctcccttggg gcaagtatg accttctcta    1140 ccaattcagc cgccaggagc tacagaactc aggttaaca gaagaagaaa ctcgaaactg    1200
tgtccggtat gaaacaaaga aacgttcctt attttttacg aaaacataca aggaagaccg    1260
gtgtaccaca aataggctgt ctgaaaagta caaaggttcc ttttttacagg gatcggagaa    1320

| | | |
|---|---|---|
| atctatatcc ctggtccagg gcgggaggag tcagcaggca gcagccttgg cttgggagaa | 1380 |
| gggcagctct ggtccagagg cgaatgtctt ctctgagtgg ttagagtcgg tgaaggaaaa | 1440 |
| ccctgctgtg gttgattatg agcttgctcc gatcatcgac ttggtcagaa acatcccatg | 1500 |
| tgcagtgaca aaacggaaca acctcaggaa agcccttcaa gaatatgcag ccaagtttga | 1560 |
| cccttgccaa tgtgctccat gtcctaataa tggccgcccc aggctctcag gcacagaatg | 1620 |
| tttgtgtgtg tgccagagtg gtacctacgg tgagaactgt gaaaaacggt ccccagatta | 1680 |
| taaatcgaat gcagtggatg ggaactgggg ctgctggtct tcctggagcg catgcaatgc | 1740 |
| tgcttatagg aggtcaagga gccgggagtg taataaccct gagccacagc gaggagggca | 1800 |
| gcgctgtgag ggcaagcatt ggcaagaaga agactgtaca ttctcaataa tggaaaaagt | 1860 |
| tggacaaccg tgcatcagtg atgatgaaga aataaaagaa gtagaccttg ctgagccaga | 1920 |
| agcagattca gggtgtcctc agccacctct cccagaaaat gcatttgtct ggaatgaaaa | 1980 |
| gaaactgtac tcagtcgggg aggaagttga aatttcatgt ctcactggat tcaaagctgt | 2040 |
| gggataccag tacttcagat gcttaccaga cagaacctgg aggcaagggg atgtcgaatg | 2100 |
| ccaacggacc gagtgcctca aaccagtcgt tcaggatgtc ctgaccatct ccccatttca | 2160 |
| gagtgtgtac aagattgggg aatccattga gctgacctgt cccagaggct tgttgttgc | 2220 |
| tggcccatcg aggtatacat gcaagggaga ctcctggaca cctcccattc caaattcact | 2280 |
| gagctgtgaa aaagatattc tgacaaagtc aaagggcctt tgtcaaccag acaaaagca | 2340 |
| atcaggatcc gagtgtgttt gtatgtcccc agaagaagac tgtagcagtt attcggaaga | 2400 |
| tctctgtata tttgatgagg gatccagtca gtacttcact tcatctgctt gcaaattttt | 2460 |
| ggctgaaaaa tgtttaaaca gcaaccagtt ccactttgtc catgctggtt cctgccaaga | 2520 |
| aggcccacag ttagaatggg gtcttgagag gctaaaactc gcaatgaaga gcacaaagag | 2580 |
| agtgccctgt ggatatgata cttgctatga ctgggaaaaa tgttcagccc acacctccaa | 2640 |
| ctgtgtctgc ctattgcccc cacaatgccc caaggatgaa aaccaactcc actgtgtcaa | 2700 |
| aatgggatca tcaatgcgtg ggaaaacagt aaacatctgt acactgggag ccgtgaggtg | 2760 |
| tgcaaacagg aaggtggaaa tactgaatcc tgggaggtgc ttggattagc actgctagtg | 2820 |
| atgaatgaat ttattattca aaaacaacgg acaggaagtg aggaaagtga atggatggga | 2880 |
| gcaaagtatg ataacacata tcttcaggaa tgtaatgata aaaacccatt actttgtata | 2940 |
| ataacctaaa caaactcttt tttaaaaaaa actcattata tgtaaactaa catagccata | 3000 |
| aattgctggc aaaaaaaaaa aaaaaaaaa aaaaaaaa | 3038 |

<210> SEQ ID NO 403
<211> LENGTH: 2901
<212> TYPE: DNA
<213> ORGANISM: Mouse

<400> SEQUENCE: 403

| | | |
|---|---|---|
| tagtatgaag gacgctttgg atgctcacac aaacccctgc ttagcgtgcg tgtctttggt | 60 |
| ttctacatcc attcaggttc ctgagcacaa ctaaggtcga tttgaaaggg tctggagatt | 120 |
| gtggaaggca tgaccagaca tctcaccttg tgtttcattt tgctggtcat gctgattgac | 180 |
| aagagtgaag cctgtttctg tgaccactac ccatggactc actggtccag ctgttctaag | 240 |
| tcctgcaatt ctggaaccca gagcagacag agacaagtag tagtgaacga ttactattgg | 300 |
| aaaaacttat gcgataagct ttgtatcaag caggagacca gagagtgcaa cttgcagaca | 360 |
| tgtcccatca actgtgtcct aggagactat ggacatggt cagactgtga cccttgtact | 420 |

```
gaaaaacagg ttaaagttaa atctgtcctg cgcccaagtc agtttggggg gcaaccatgc    480
acagagcccc tggtgacctt tcaaccatgt gtcccctcca agctctgcaa aattgaagag    540
actaactgca agaataagtt cctctgtgac agtgggcgct gtattcccag caagttagaa    600
tgcaatggag agaatgactg tggagacaat tcagatgaaa ggaactgtgg gaggacaaag    660
ccagtgtgca cacggatata cactcccatc cctagtgtgc agctgatggg cactgggttt    720
cattttctgg caggagagcc cagaggagaa gttcttgaca actctttcac tggaggaata    780
tgtaaacttg tcaagaccag tcgagccagt aatccatacc gtgtttcagc caatctggaa    840
aatgtcaact ttgaggtaca aactatagaa gatgacttga aaacagaatt ctacaagaat    900
ttaatctctt ttgaaaaaaa taaaaatgaa gacagtcttt cagtggatga aggacaaaa    960 ttttcccta taccaatttt ccatttctca gagaaaaatg aacattccca ttatagctct   1020
gccttcaaca aagtcattaa agcttcccac aagaaggatt ctagctttat caggatccat   1080
aagctgataa aagtcttaaa cttcacaatg aaagcaacag acctacagct ttcagatgtc   1140
ttcctgaaag cccttgtcca cctgccttta gaatacaact ctgctgtgta cagccggata   1200
tttgatgact cgggaccca ctacttcacc tcaggctccc ttgggggcaa gtatgacctt   1260
atctaccaat tcagccgcca ggagctacag aactcaggtt taacagaaga agaagctcaa   1320
aactgtgtcc agtatgaaac aaagaaactt aagtttcttt atatggaaat acacaaggaa   1380
gacacgtgca ccaaaaacaa gctgtctgaa aaatatggag gttccttttt gcagggatca   1440
gagaaatcca tttccctggt ccagggcggg aggagtcagc aggcagcagc cttggcttgg   1500
gagaagggca cctctggtcc agaggagaat gtctattctg agtggctaga atcggtgaag   1560
gaaaaccctg ctgtagttga ttataagctt gccccaatta cagacttggt cagaaacatc   1620
ccatgtgcag tgacaaaacg gaacaacctc aggagagcgc ttcaagagta tgcagccaag   1680 tttgacccctt gccagtgtgc tccatgtccc aataatggcc gccccaggct ctcaggcacg   1740
gaatgcctgt gtgtgtgcca gagcggcacc tacgttgaga actgtgagcg caggtcccca   1800
ggttacaaat ctgatgcagt ggatggaaac tggggctgct ggtcttcctg gagtgcgtgc   1860
aatgctgctt ataggagatc aagaacccga gagtgtaata accctgcgcc acagcgagga   1920
ggacaaagct gtggtggcaa ggatcagcaa gaagaagact gtacagtctc aataatggaa   1980
aatgttggac aaccatgtat caatgatgat gaagaaatga cagaggtaga ccttgctgag   2040
ccagaagcag aatcagggtg ttctcaacca cctctcccag aaaacgcatt tacctggaat   2100
gagaagaaac tgtactcagt tggggaggaa gttgaaattt catgtcttac tggattcaca   2160
gctgttggat tccagtactt gagatgttta ccagacagaa cctggagtca aggagatgtg   2220
gaatgccaaa ggacctcgtg cctcaagccc gttgttcagg atgtcctgac catctcccca   2280
tttcagagag tgtatcagat tgggggaatcc attgagctga catgccccag aggctttgtt   2340
gttgctggac atcaaggta tacatgcaag gaagactcct ggacacctcc catttcaaat   2400
tcattgacct gtgaacaagg tgtcagagac catccgtgag aaagtgatcc cttcacaatc   2460
tccttaacaa gtcaaagggc cttgaactaa gagctggttg ccacccccttt cctccttatt   2520 cccttcctaa cacctaagac tgtaaaattt gaataacagt cccctcttcc ctatctcttt   2580
ccgagttccc atgacatcca aggacatgag ctgtgcctga gcccagcttg actcccaagg   2640
ctgttgagga ggatcaaggc tctggagcgt cctttccctt gttctttgta caactctccc   2700 tcgaccccctc ccctattttc cgcgatgata agatgcaaag tgcctgctgc ttggcgcctg   2760
```

```
acttcagccc ccatgtcagc agtcgtcctt tcccttgttc tttgtacaac tctccctcga   2820
cccctcccct attttccgcg atgtatgctt tataaggaaa gcacctcagc ttaataaatg   2880
agaccttgat aggtttaatc t                                             2901
```

<210> SEQ ID NO 404
<211> LENGTH: 16
<212> TYPE: DNA
<213> ORGANISM: Artificial
<220> FEATURE:
<223> OTHER INFORMATION: synthetic oligomer

<400> SEQUENCE: 404
gagcagacag agacaa                                                   16

<210> SEQ ID NO 405
<211> LENGTH: 16
<212> TYPE: DNA
<213> ORGANISM: Artificial
<220> FEATURE:
<223> OTHER INFORMATION: synthetic oligomer

<400> SEQUENCE: 405
ttgtctctgt ctgctc                                                   16

<210> SEQ ID NO 406
<211> LENGTH: 16
<212> TYPE: DNA
<213> ORGANISM: Artificial
<220> FEATURE:
<223> OTHER INFORMATION: synthetic oligomer

<400> SEQUENCE: 406
tattcccagc aagtta                                                   16

<210> SEQ ID NO 407
<211> LENGTH: 16
<212> TYPE: DNA
<213> ORGANISM: Artificial
<220> FEATURE:
<223> OTHER INFORMATION: synthetic oligomer

<400> SEQUENCE: 407
taacttgctg ggaata                                                   16

<210> SEQ ID NO 408
<211> LENGTH: 16
<212> TYPE: DNA
<213> ORGANISM: Artificial
<220> FEATURE:
<223> OTHER INFORMATION: synthetic oligomer

<400> SEQUENCE: 408
gtgtgcagct gatggg                                                   16

<210> SEQ ID NO 409
<211> LENGTH: 16
<212> TYPE: DNA
<213> ORGANISM: Artificial
<220> FEATURE:
<223> OTHER INFORMATION: synthetic oligomer

<400> SEQUENCE: 409
cccatcagct gcacac                                                   16

```
<210> SEQ ID NO 410
<211> LENGTH: 16
<212> TYPE: DNA
<213> ORGANISM: Artificial
<220> FEATURE:
<223> OTHER INFORMATION: synthetic oligomer

<400> SEQUENCE: 410
ggtacaaact atagaa                                                         16

<210> SEQ ID NO 411
<211> LENGTH: 16
<212> TYPE: DNA
<213> ORGANISM: Artificial
<220> FEATURE:
<223> OTHER INFORMATION: synthetic oligomer

<400> SEQUENCE: 411
ttctatagtt tgtacc                                                         16

<210> SEQ ID NO 412
<211> LENGTH: 16
<212> TYPE: DNA
<213> ORGANISM: Artificial
<220> FEATURE:
<223> OTHER INFORMATION: synthetic oligomer

<400> SEQUENCE: 412
gcctttagaa tacaac                                                         16

<210> SEQ ID NO 413
<211> LENGTH: 16
<212> TYPE: DNA
<213> ORGANISM: Artificial
<220> FEATURE:
<223> OTHER INFORMATION: synthetic oligomer

<400> SEQUENCE: 413
gttgtattct aaaggc                                                         16

<210> SEQ ID NO 414
<211> LENGTH: 19
<212> TYPE: DNA
<213> ORGANISM: Artificial
<220> FEATURE:
<223> OTHER INFORMATION: synthetic oligomer

<400> SEQUENCE: 414
gagcagacac agacaaata                                                      19

<210> SEQ ID NO 415
<211> LENGTH: 16
<212> TYPE: DNA
<213> ORGANISM: Artificial
<220> FEATURE:
<223> OTHER INFORMATION: synthetic oligomer

<400> SEQUENCE: 415
ttgtctgtgt ctgctc                                                         16

<210> SEQ ID NO 416
<211> LENGTH: 19
<212> TYPE: DNA
<213> ORGANISM: Artificial
<220> FEATURE:
<223> OTHER INFORMATION: synthetic oligomer
```

```
<400> SEQUENCE: 416
ctgcattgcc agaaagtta                                                19

<210> SEQ ID NO 417
<211> LENGTH: 16
<212> TYPE: DNA
<213> ORGANISM: Artificial
<220> FEATURE:
<223> OTHER INFORMATION: synthetic oligomer

<400> SEQUENCE: 417
taactttctg gcaatg                                                   16

<210> SEQ ID NO 418
<211> LENGTH: 19
<212> TYPE: DNA
<213> ORGANISM: Artificial
<220> FEATURE:
<223> OTHER INFORMATION: synthetic oligomer

<400> SEQUENCE: 418
gtgtacagtt gatgggcaa                                                19

<210> SEQ ID NO 419
<211> LENGTH: 16
<212> TYPE: DNA
<213> ORGANISM: Artificial
<220> FEATURE:
<223> OTHER INFORMATION: synthetic oligomer

<400> SEQUENCE: 419
cccatcaact gtacac                                                   16

<210> SEQ ID NO 420
<211> LENGTH: 19
<212> TYPE: DNA
<213> ORGANISM: Artificial
<220> FEATURE:
<223> OTHER INFORMATION: synthetic oligomer

<400> SEQUENCE: 420
ggtacaaact gcagaagat                                                19

<210> SEQ ID NO 421
<211> LENGTH: 16
<212> TYPE: DNA
<213> ORGANISM: Artificial
<220> FEATURE:
<223> OTHER INFORMATION: synthetic oligomer

<400> SEQUENCE: 421
ttctgcagtt tgtacc                                                   16

<210> SEQ ID NO 422
<211> LENGTH: 25
<212> TYPE: DNA
<213> ORGANISM: Artificial
<220> FEATURE:
<223> OTHER INFORMATION: synthetic oligomer

<400> SEQUENCE: 422
catctgcctc tagaatacaa ctctg                                         25

<210> SEQ ID NO 423
<211> LENGTH: 16
```

```
<212> TYPE: DNA
<213> ORGANISM: Artificial
<220> FEATURE:
<223> OTHER INFORMATION: synthetic oligomer

<400> SEQUENCE: 423
gttgtattct agaggc                                                      16
```

COMPLEMENT ANTAGONISTS AND USES THEREOF

CROSS-REFERENCE TO RELATED APPLICATIONS

This application is a divisional of U.S. application Ser. No. 13/003,062, filed on Mar. 15, 2011, which is a 35 U.S.C. 371 national stage filing of International Application No. PCT/NL2009/050418 filed on Jul. 10, 2009, which claims priority to U.S. Provisional Application No. 61/079,501, filed on Jul. 10, 2008. The contents of the aforementioned applications are hereby incorporated by reference.

FIELD OF THE INVENTION

The present invention features compositions and methods for modulating the expression of complement component 6 (C6), for example. In one embodiment, the invention relates to antagonists that reduce or block expression of that protein. The invention has a wide variety of applications including use to promote nerve regeneration in a mammal following acute or chronic injury to the nervous system.

BACKGROUND

The complement system includes a group of some thirty (30) proteins that are recognized to be an important part of the immune response. The system can be activated by a classical (usually antibody-dependent) or alternative (usually antibody-dependent) pathway. Activation via either pathway leads to the generation of an enzyme called C5 convertase. The convertase helps form a protein called C5b that, among other functions, initiates what is often referred to as the terminal complement pathway. A goal of this pathway is to form a membrane attack complex (MAC) within the membrane of an invading pathogen, thereby causing lysis. The MAC is generally formed by the sequential assembly of complement proteins C6, C7, C8 and (C9)$_n$ along with C5b. See generally Walport, M. J. 2001. *N. Engl. J. Med.* 344: 1058-1066; and 1140-1144.

There are reports of natural and synthetic inhibitors of the complement system. These include certain small molecules, proteins, antibodies, flavanoids, and polysaccharides, for example. See S. Bureeva et al. (2005) *Drug Discovery Today* 10: 1535.

Neuronal degeneration is a hallmark of many acute and chronic neuropathies. One mode of axonal degeneration, termed Wallerian Degeneration (WD) is a highly destructive process in which the part of an axon distal to an injury dies. Initial abnormalities can be seen as early as several hours after injury with more visible WB apparent a day or two later (Ballin R H and Thomas P K (1969) *Acta Neuropathol* (Berl) 14: 237. For instance, myelin sheaths collapse and become engulfed by scavenging cells (Leonhard et al. (2002) *Eur. J. Neurosci.* 16: 1654). These processes are associated with eventual nerve repair and regeneration. There are reports that certain complement components mediate the myelin phagocytosis (Dailey et al. (2002) *J. Neurosci* 18: 6713; and Liu (1999) *J. Peripher. Nerv. Syst.* 4: 123). Although there is some uncertainty about which complement components are needed to mediate these processes, MAC formation has been reported to essential for rapid WD (Ramaglia, V. et al. (2007) *J. Neurosci.* 27: 7663).

A variety of nucleic acid antagonists are known. For example, various antisense oligomers have been shown to be useful for several therapeutic, diagnostic, and research applications (see e.g, Cheson, B D (2007) *Ther Clin Risk Manag.* 3(5):855 (discussing, for instance, favorable clinical trial data for oblimersen). Short interfering RNA (siRNA), a type of RNA antagonist, has been proposed to be a useful therapeutic and research tool (McManus and Sharp, (2002) *Nature Reviews Genetics* 3: 737. Other RNA antagonists such as RNAi-induced silencing complexes with a discontinuous passenger strand have also been reported (Leuschner, et al. (2006) *EMBO Reports* 7:314).

It would be desirable to have antagonists that block or inhibit activity of a mammalian complement component 6 (C6) protein, for example. It would be further desirable to have antagonists that can be used to prevent, treat, or reduce the severity of neuropathies that are known or suspected of being associated with formation of the MAC.

SUMMARY OF THE INVENTION

The present invention features antagonists that reduce or block activity of a mammalian Complement Component 6 (C6) protein, for example. Illustrative antagonists can be used to prevent, treat or reduce the severity of neuropathies that are known or suspected of being associated with formation of a membrane attack complex (MAC). Particular antagonists feature single- and multi-stranded nucleic acids (typically about one, two or about three strands) that block or reduce expression of the mammalian complement 6 (C6) protein. The invention has a wide variety of applications including use to promote nerve regeneration in a mammal following acute or chronic nerve damage.

In one aspect, the present invention provides an oligomer of between about 10 to 50 nucleotides in length having a contiguous nucleobase sequence with at least 80% sequence identity to a corresponding region of a nucleic acid which encodes the COMPLEMENT COMPONENT 6 (C6) sequence represented by SEQ ID NO: 1 (human), SEQ ID NO: 402 (rat) or SEQ ID NO: 403 (mouse) or a naturally occurring allelic variant thereof. Preferred oligomers include at least one nucleotide analogue and are capable of reducing the level of C6 mRNA expression in a mammal by at least about 20% as determined by, for instance, a PCR assay.

For the sake of simplicity, the phrase <<mammalian complement component 6 (C6)>> will be abbreviated as <<C6>>, <<mammalian C6 protein>> and the like unless specified otherwise.

In another aspect, the invention features a double-stranded nucleic acid compound that preferably includes a first oligomer (passenger strand) and a second oligomer (antisense strand) preferably targeted to a nucleic acid molecule encoding a mammalian C6 protein, particularly human, rat of mouse C6. In one embodiment, each strand of the compound includes from between about 12 to about 35 nucleobases and the antisense strand consists of a contiguous nucleobase sequence with at least 80% sequence identity to a corresponding region of a nucleic acid which encodes the COMPLEMENT COMPONENT 6 (C6) sequence represented by SEQ ID NO: 1 (human), SEQ ID NO: 402 (rat) or SEQ ID NO: 403 (mouse) or a naturally occurring allelic variant thereof. A preferred oligomer includes at least one oligonucleotide analogue. In another aspect, the invention features a composition that includes an RNA complex with a core double-stranded region that includes an antisense strand consisting of a contiguous nucleobase sequence with at least 80% sequence identity to a corresponding region of a nucleic acid which encodes the COMPLEMENT COMPONENT 6 (C6) sequence represented by SEQ ID NO: 1 (human), SEQ ID NO: 402 (rat) or SEQ ID NO: 403 (mouse) or a naturally occurring allelic variant thereof. Preferably, the oligomer includes at least one oligonucleotide analogue, the RNA complex further comprising a discontinuous passenger strand that is hybridised to the antisense strand.

Further provided by the present invention is a method of reducing or inhibiting the expression of a mammalian C6 such as human C6, in a cell or a tissue. In one embodiment, the method includes the step of contacting the cell or tissue with at least one oligomer, double-stranded compound or other composition of the invention in an amount that sufficient to reduce or inhibit expression of the C6 protein in the cell or tissue.

The invention also provides for a method for treating, preventing or reducing symptoms of a disorder mediated by undesired activity of the complement system and particularly undesired formation of the MAC. In one embodiment, the method includes the step of administering a composition of the invention (therapeutically or prophylactically) to a mammal in need thereof and in an amount sufficient to reduce or block MAC formation in the mammal A preferred disorder within the scope of the present invention is one in which nerve regeneration is deficient or otherwise abnormal.

Further provided by the present invention is a method of enhancing nerve regeneration in a mammal that includes the step of administering to the mammal (therapeutically or prophylactically) an amount of at least one composition of the invention sufficient to reduce or inhibit expression of C6 in the mammal and enhance nerve regeneration therein. Preferably, formation of the MAC is also reduced or inhibited in the mammal.

Practice of the invention provides important advantages.

For instance, there are reports that the liver can sometimes sequester nucleic acids and reduce activity of nucleic acid based therapeutics with targets outside the liver.

However, the liver is a major site of complement protein synthesis. Accordingly, it is believed that the sequesteration of the invention compounds will advantageously reduce or block C6 protein expression.

Additionally, compounds of the invention can be used alone or in combination with other agents (including at least one other invention composition) to reduce or inhibit MAC formation in a mammal that has or is suspected of having an acute or chronic neuropathy. It is believed that use of the invention before, during or after the injury will help promote nerve regeneration in the mammal.

Further uses and advantages of the invention are discussed, infra.

DETAILED DESCRIPTION

Figure 1:
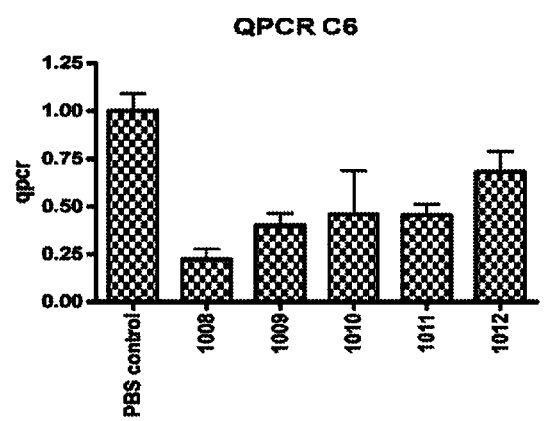
FIG. 1 is a graph showing C6 complement mRNA levels after three days of treatment in mice with complement antisense LNA. Batch Nos (Y-axis) are explained in Example 2.

As discussed, the invention features antagonists that preferably block or inhibit activity of a mammalian C6, for instance. Reference herein to a <<nucleic acid antagonist>> means a compound that includes or consists of nucleic acid and, preferably, one or more nucleic acid analogues as disclosed herein. An <<RNA antagonist>> is a nucleic acid antagonist whose intended function is to reduce or block expression of a particular RNA(s).

In one aspect, the invention provides oligomeric compounds (oligomers) for use in decreasing the function of nucleic acid molecules that encode the mammalian C6, preferably to reduce the amount of the C6 produced. An example is an antisense compound. This goal is accomplished, for example, by providing antisense compounds which specifically hybridize with one or more nucleic acids encoding the mammalian C6. As used herein, the terms "target nucleic acid" and "nucleic acid encoding C6>> encompass DNA encoding the mammalian C6, RNA encoding the mammalian C6 (including pre-mRNA and mRNA) transcribed from such DNA, and also cDNA derived from such RNA. A particular mammalian C6 of interest is the human complement component 6 (C6) encoded by the cDNA sequence represented by Table 3 (SEQ ID NO: 1). Another mammalian C6 of interest is the rat and mouse C6 sequences represented by SEQ ID Nos. 402 and 403, respectively.

As used herein, "oligonucleotide" refers to a component of an invention compound such as an oligomer or polymer of ribonucleic acid (RNA) or deoxyribonucleic acid (DNA) or analogues thereof. This term includes oligonucleotides composed of naturally-occurring nucleobases, sugars and covalent internucleoside (backbone) linkages as well as oligonucleotides having non-naturally-occurring portions. Such modified or substituted oligonucleotides are often preferred over native forms because of desirable properties such as, for example, enhanced cellular uptake, enhanced affinity for nucleic acid target and increased stability in the presence of nucleases, for instance. Accordingly, an <<oligomer>> in accord with the invention, including plural forms, is an oligonucleotide that includes naturally-occurring nucleobases, sugars and covalent backbone linkages as well as constructs that include one or more analogues thereof.

In the present context, the term "nucleotide" means a 2-deoxyribose (DNA) unit or a ribose (RNA) unit which is bonded through its number one carbon to a nitrogenous base, such as adenine (A), cytosine (C), thymine (T), guanine (G) or uracil (U), and which is bonded through its number five carbon atom to an internucleoside linkage group (as defined below) or to a terminal groups (as defined herein). Accordingly, when used herein the term "nucleotide" encompasses RNA units (or monomers) comprising a ribose unit which is bonded through its number one carbon to a nitrogenous base, such as A, C, T, G or U, and which is bonded through its number five carbon atom to a phosphate group or to a terminal group. Analogously, the term "nucleotide" also encompasses DNA units (or monomers) comprising a 2-deoxyribose unit which is bonded through its number one carbon to a nitrogenous base, such as A, C, T, G or U, and which is bonded through its number five carbon atom to a phosphate group or to a terminal group. The term "nucleotide" also covers variants or analogues of such RNA and DNA monomers as described herein.

By "nucleoside" is meant a 2-deoxyribose (DNA) unit or a ribose (RNA) unit which is bonded through its number one carbon to a nitrogenous base, such as adenine (A), cytosine (C), thymine (T), guanine (G) or uracil (U). Accordingly, when used herein the term "nucleoside" encompasses RNA units (or monomers) comprising a ribose unit which is bonded through its number one carbon to a nitrogenous base, such as A, C, T, G or U. Analogously, the term "nucleoside"

also encompasses DNA units (or monomers) comprising a 2-deoxyribose unit which is bonded through its number one carbon to a nitrogenous base, such as A, C, T, G or U. The term "nucleoside" also covers variants or analogues of such RNA and DNA monomers as provided herein. It will be understood that the individual nucleosides are linked together by an internucleoside linkage group such as those naturally-occurring and synthetic linkages as provided herein.

Antisense Oligomers

Without wishing to be bound to theory, it is believed that the specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include, for instance, replication and transcription. The functions of RNA to be interfered with include at least some vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the mammalian C6 protein. In the context of the present invention, "modulation" means either an increase (stimulation) or a decrease (inhibition) in the expression of a gene relative to a suitable control such as expression in the absence of the oligomer. In the context of the present invention, inhibition is the preferred form of modulation of gene expression and mRNA is one target.

As used herein, "hybridization" generally refers to hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target.

It is understood that the sequence of an invention compound need not be 100% complementary to that of its target nucleic acid to be specifically hybridizable. An antisense compound, for instance, is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Preferred oligomers of the invention are typically identified through in silico design and, in some cases, in vitro and/or in vivo testing. The target sites to which preferred invention sequences are complementary are hereinbelow referred to as "active sites" and are therefore preferred sites for targeting. Therefore another embodiment of the invention encompasses compounds which hybridize to these active sites.

It is an object of the invention to use particular oligomers as antisense compounds, for instance. "Targeting" an antisense or other invention compound to a particular nucleic acid is a multistep process. The targeting process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a mammalian C6 protein, particularly the human, rat and mouse C6 sequences represented in Table 3 (SEQ ID NOs.1, 402 and 403). The targeting process also includes determination of a site or sites within this gene for the antisense interaction to occur including, but not limited to, detection or modulation of expression of the protein.

Additional considerations include selecting oligomers with reduced capacity to cross-hybridize with undesired targets and to assume difficult secondary structures in solution. More preferred oligomers of the invention are selected for reduced toxic and miRNA-like seed region motifs and passenger-strand mediated off-targeting. Still further preferred oligomers in accord with the invention are shown in Tables. 4A-4E and Tables. 5A-5F, for instance.

Referring now to Tables. 4A-4E, SEQ ID Nos. 2, 24, 46, 68, 90, 112, 134, 156, 178, 200 are preferred targets of the human C6 sequence represented by Table 3 (SEQ ID NO:1) with sequences immediately below each showing oligomers in order of decreasing preference. Thus, SEQ ID NO: 2 is one preferred target of human C6 with oligomers represented by SEQ ID Nos: 3-23, being preferred, in decreasing order of preference, for targeting that site. Referring again to Tables. 4A-4E, additionally preferred targets include those sequences represented by SEQ ID Nos: 222, 225, 228, 231, 234, 237, 240, 243, 246, and 249 and RNA and reverse complement versions thereof shown immediately below each target. Rat and mouse C6 is expected to have identical or very similar target sites.

Additionally preferred oligomers for certain embodiments show 100% sequence identity between the human, rat and mouse sequences (e.g., Tables. 5A-5F; SEQ ID NO: 292). As will be appreciated, such oligomers can be used in the human, rat and mouse without substantial mismatch problems or the need to have multiple oligomer designs for each mammal.

More particular oligomers according to the invention are sufficiently complementary to the target, i.e., hybridize sufficiently well and with sufficient specificity, to give intended results. Preferably, the desired effect is a reduction or total inhibition of expression of mammalian C6 such as the human, rat or mouse C6 protein, manifested as a reduction or total inhibition of the amount of the corresponding C6 mRNA as determined, for instance, by the polymerase chain reaction (PCR) and/or immunological approaches using an anti-C6 antibody to monitor protein.

In one PCR approach, oligonucleotide primers can be designed for use in PCR reactions to amplify corresponding DNA sequences from cDNA or genomic DNA extracted from any organism of interest. An example of a suitable cDNA is the human C6 sequence represented by Table. 1 (SEQ ID NO: 1). Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.) hereinafter "Sambrook". See also Innis et al., eds. (1990) *PCR*

Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like. A method for performing qPCR is described in the Examples section.

If desired, additional functionality of a particular oligomer can be tested and optionally quantified by using what is known as a total hemolytic ((CH50) assay). In this approach, plasma, blood or other suitable biological sample is isolated from a mammal to which has been administered one or more of the oligomers. The assay measures the ability of the test sample to lyse 50% of a standardized suspension of sheep erythrocytes coated with anti-erythrocyte antibody. Total complement activity is said to be abnormal if any component is defective. See, for example, Kabat, E. A and Mayer, M. M. (1961) *Complement and Complement Fixations. In: Experimental Immunochemistry*, 2nd Edition, Charles C. Thomas, Springfield, Ill. p. 133-240.

In another approach, MAC formation can be detected and quantified if desired using immunological approaches described by Ramaglia, V. et al. (2007) *J. Neurosci.* 27:7663.

Additionally preferred oligomers of the invention will exhibit good capacity to block or reduce mRNA encoding for human, rat or mouse C6. More specifically, such oligomers will be capable of reducing the level of a particular C6 mRNA in a mammal such as human, rat or mouse, by at least about 10%, 20%, 30%, 40%, 50%, 60%, 70%, 80%, 90%, 95%, 99%, up to about 100% as determined by a suitable PCR assay, preferably qPCR. Additionally preferred oligomers are substantially non-toxic in a mammalian host such as a rodent. That is, they do not kill the mammal over the course of an assay in which a therapeutic amount of the oligomer is administered to the mammal for a suitable period (eg., about 1 to about 10 mg/kg IP daily for up to a few days or weeks), the liver excised from that mammal and used as a source of nucleic acid, typically RNA. The nucleic acid prepared from the liver using standard procedures and is subjected to qPCR to measure C6 mRNA levels using the Roche Lightcycler 480 and universal probes recommended by the manufacturer. An illustrative assay is provided in Example 1 in which several invention oligomers were found to be relatively non-toxic and able to reduce mouse C6 mRNA by at least about 20%, 30%, 40%, at least about 50%, 60%, 70%, at least about 80% or more up to about 90%, 95%, to about 99% or 100%. Reference herein to an <<oligomer validation test>> will refer to the foregoing specific assay to confirm non-toxicity and ability to inhibit C6 mRNA expression in vivo.

Preferred use of the oligomers features preventing, treating, or reducing the severity of neuropathies that are known or suspected of being associated with formation of a the MAC.

Although the invention provides for one or a combination of suitable oligomers, a generally preferred oligomer is one that is between about 10 to about 50 nucleobases in length, for instance, between about 12 to about 45 nucleobases in length, between about 15 to about 40 nucleobases in length, between about 16 to about 35 nucleobases in length with about 18 to about 30 nucleobases in length being useful for many applications. Preferably, the oligomer includes a contiguous nucleobase sequence of a total of between 10-50 nucleobases, for instance, between about 12 to about 45 nucleobases in length, between about 15 to about 40 nucleobases in length, between about 16 to about 35 nucleobases in length with about 18 to about 30 nucleobases in length being useful for many applications in which the contiguous nucleobase sequence is at least 80% sequence identify, for instance, such as about 85%, about 90%, about 95% or about 98% sequence identity to a corresponding region of a nucleic acid which encodes the mammalian C6 of interest. A particular sequence of interest is the human C6 represented by SEQ ID NO: 1, rat C6 represented by SEQ ID NO: 402 and mouse C6 represented by SEQ ID NO: 403 (as well as naturally-occurring allelic variants of SEQ ID Nos: 1, 402 and 403). <<Naturally occurring allelic variants>> can be identified with the use of well-known molecular biology techniques, such as, for example, polymerase chain reaction (PCR) and hybridization techniques as outlined herein.

The exent of homology between a pair of nucleic acids can be determined by one or a combination of strategies. In one approach, the percent sequence identity is determined by inspection. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (Version 3.0, copyright 1997); and GAP, BESTFIT, BLAST, FASTA, and TFASTA in the Wisconsin Genetics Software Package of Genetics Computer Group, Version 10 (available from Accelrys, 9685 Scranton Road, San Diego, Calif., 92121, USA). The scoring matrix used in Version 10 of the Wisconsin Genetics Software Package is BLOSUM62 (see Henikoff and Henikoff (1989) *Proc. Natl. Acad. Sci. USA* 89:10915). Alignments using these programs can be performed using the default parameters. Other alignment considerations are within the skill of those working in the field. See also U.S. Pat. No. 7,378,499 and references cited therein.

Unless otherwise stated, nucleotide and amino acid sequence identity/similarity values provided herein refer to the value obtained using GAP with default parameters, or any equivalent program. By "equivalent program," any sequence comparison program is intended that, for any two sequences in question, generates an alignment having identical nucleotide or amino acid residue matches and an identical percent sequence identity when compared to the corresponding alignment generated by the preferred program. See Needleman and Wunsch (1970) *J. Mol. Biol.* 48:443-453 for more information.

For purposes of the present invention, comparison of nucleotide or protein sequences for determination of percent sequence identity to the human, rat and mouse C8 sequences described herein is preferably made using the GAP program in the Wisconsin Genetics Software Package (Version 10 or later) or any equivalent program. For GAP analyses of nucleotide sequences, a GAP Weight of 50 and a Length of 3 was used.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

In one embodiment of the foregoing oligomers, the contiguous nucleobase sequence includes no more than about 3, such as no more than about 1 or about 2 mismatches with respect to the corresponding region of a nucleic acid which encodes the mammalian C6 of interest, particularly SEQ ID NO:1. For example, the contiguous nucleobase sequence can include no more than a single mismatch to the corresponding region of a nucleic acid which encodes the mammalian C6 of interest. Alternatively, the contiguous nucleobase sequence includes no mismatches, (e.g. is fully complementary to) with the corresponding region of a nucleic acid which encodes the mammalian C6 of interest. In another embodiment, the nucleobase sequence of the oligomer consists of the contiguous nucleobase sequence.

Practice of the invention is compatible with a wide range of mammalian C6 sequences including those human, rat and mouse sequences specified herein. The nucleic acid and protein sequences of such proteins are available from the U.S. National Center for Biotechnology Information ((NCBI)-Genetic Sequence Data Bank (Genbank). In particular, sequence listings can be obtained from Genbank at the National Library of Medicine, 38A, 8N05, Rockville Pike, Bethesda, Md. 20894. Genbank is also available on the internet. See generally Benson, D. A. et al. (1997) *Nucl. Acids. Res.* 25: 1 for a description of Genbank. Protein and nucleic sequences not specifically referenced can be found in Genbank or other sources disclosed herein. See (NM_176074) disclosing a rat C6 sequence, (NM_016704), disclosing a mouse C6 sequence, for instance.

Other oligomer embodiments are within the scope of the present invention. For example, and in one embodiment, the contiguous nucleobase sequence of the oligomer includes a contiguous subsequence of at least 6, for example, about 7, 8, 9, 10, 11, 12, 13, 14, 15, 16, 17, 18, 19, 20, 21, 22, 23, 24, 25, 26, 27, 28, 29 or about 30-32 nucleobase residues which, when formed in a duplex with the complementary human, rat or mouse C6 target RNA, for instance, is capable of recruiting or RNaseH. By <<recruiting RNase H>> is meant that the enzyme contacts the complex as determined by one or a combination of assays that can detect and quantify activity of the enzyme. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Cleavage of the RNA target can be routinely detected by gel electrophoresis.

Thus in one embodiment, the contiguous nucleobase sequence of the oligomer can include a contiguous subsequence of at least 7, such as at least 8, at least 9 or at least 10 nucleobase residues which, when formed in a duplex with the complementary mammalian C6 target is capable of recruiting RNaseH. In another embodiment, the contiguous subsequence is at least 9 or at least 10 nucleobases in length, such as at least 12 nucleobases or at least 14 nucleobases in length, such as 14, 15 or 16 nucleobases residues which, when formed in a duplex with the complementary mammalian C6 target RNA is capable of recruiting RNaseH.

Additionally preferred oligomers for use with the invention will be of a length suitable for intended use. Thus in one embodiment, the oligomer has a length of between about 8 to about 50 nucleobases, about 9 to about 50 nucleotides, about 10 to about 50 nucleotides, about 9 to about 40 nucleobases, about 10 to about 35 nucleobases, about 10 to about 22 nucleobases, for instance, about 12 to about 18 nucleobases, about 14, about 15 or about 16 nucleobases, about 10, 11, 12, 13 or about 14 nucleobases.

As will be appreciated, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

While the foregoing oligomers will be preferred for certain applications, use of oligomers with one or more oligonucleotide analogues will often be preferred (sometimes referred to herein as oligonucleotide <<mimetics or derivatives>>). Thus in one invention embodiment, oligomers of the invention will include one or more non-nucleobase compounds alone or in combination with modified backbones or non-natural internucleosdie linkages therein. As defined in this specification, oligonucleotides having modified backbones include those that retain a phosphorus atom in the backbone and those that do not have a phosphorus atom in the backbone. For the purposes of this specification, and as sometimes referenced in the field, modified oligonucleotides that do not have a phosphorus atom in their internucleoside backbone can also be considered to be oligonucleosides.

Illustrative modified oligonucleotide backbones include, for example, phosphorothioates, chiral phosphorothioates, phosphoro-dithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and amino alkylphosphoramidates, thionophosphoramidates, thionoalkyl-phosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e., a single inverted nucleoside residue which may be abasic (the nucleobase is missing or has a hydroxyl group in place thereof). Various salts, mixed salts and free acid forms are also included. See, for example, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697, 7,335,764, and 5,625,050, for disclosure relating to making and using such compositions.

Thus in one invention embodiment, an oligomer of the invention has a backbone that is fully phosphorothiolyated.

Additional modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269, 7,335,764, and 5,677,439, for disclosure relating to making and using such compositions.

In other oligonucleotide analogues, both the sugar and the internucleoside linkage, i.e., the backbone, of the nucleotide units are replaced with other groups. The base units are maintained for hybridization with an appropriate nucleic acid target compound. One such oligomeric compound is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. See, for instance, U.S. Pat. Nos. 5,539,082; 5,714,331; 5,719,262, and Nielsen et al., *Science*, 1991, 254, 1497-1500.

Additional embodiments of the invention are oligomers with phosphorothioate backbones and oligonucleosides with heteroatom backbones, and in particular —$CH_2$—NH—O—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Further oligonucleotides having morpholino backbone structures of the above-referenced U.S. Pat. No. 5,034,506, for example.

Modified oligomers in accord with the invention may also contain one or more substituted sugar moieties. Illustrative oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$N$H_2$, O($CH_2$)$_n$$CH_3$, O($CH_2$)$_n$ON$H_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, S$CH_3$, OCN, Cl, Br, CN, $CF_3$, O$CF_3$, SO$CH_3$, SO$_2$$CH_3$, ONO$_2$, NO$_2$, N3, N$H_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2$$CH_2$O$CH_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A preferred modification includes Locked Nucleic Acids (LNAs) in which the 2'-hydroxyl group is linked to the 3' or 4' carbon atom of the sugar ring thereby forming a bicyclic sugar moiety. The linkage is, for instance, a methelyne (—$CH_2$—)$_n$ group bridging the 2' oxygen atom and the 4' carbon atom wherein n is 1 or 2. LNAs and preparation thereof are described in WO 98/39352 and WO 99/14226.

Additionally suitable LNA monomers (sometimes called "locked nucleic acid monomer", "locked nucleic acid residue", "LNA monomer" or "LNA residue") refer to a bicyclic nucleotide analogue as disclosed, for example, WO 00/56746, WO 00/56748, WO 01/25248, WO 02/28875, WO 03/006475, U.S. Patent Publication No. 2007/0191294, WO 03/095467, U.S. Pat. Nos. 6,670,461, 6,794,499, 7,034,133, 7,053,207 (L-Ribo-LNA), U.S. Pat. Nos. 7,060,809, and 7,084,125 (Xylo-LNA). The LNA monomer may also be defined with respect to its chemical formula. Thus, an example of an "LNA monomer" as used herein has the following structure:

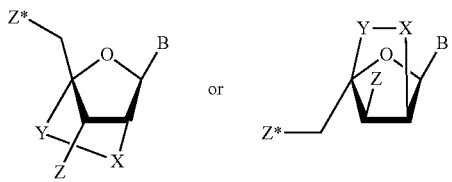

wherein, X is selected from the group consisting of O, S and $NR^H$—, where $R^H$ is H or alkyl, such as $C_{1-6}$-alkyl; Y is (—$CH_2$)$_r$, where r is an integer of 1-6; with the proviso that when X=O then r is not 2. Z and Z* are independently absent or selected from the group consisting of an internucleoside linkage group, a terminal group and a protection group; and B is a nucleobase. In one embodiment, r=1 and X is O and each of Z, Z* is independently absent or selected from the group consisting of an internucleoside linkage group, terminal group and a protection group and B is a nucleobase. The foregoing LNA monomers can be in the beta-D form, the alpha-L-form as described, for example, in the U.S. Patent Publication 2007/0191294.

Also included within the phrase "LNA monomer" are oligomers in which one or more nucleotides are substituted by amino-LNA, thio-LNA or both. By <<amino-LNA>> and <<thio-LNA>> is meant the LNA monomer shown in the above formula in which the oxygen atom of the pentose ring is replaced with a nitrogen or sulfur atom, respectively. Methods for making and using such LNA monomers are disclosed, for instance, in U.S. Pat. Nos. 7,060,809; 7,034,133; 6,794, 499; 6,670,461; and references cited therein. A particular substitution is C- or T-amino-LNA; or C- or T-thio LNA. Certain amino-LNA and thio-LNA analogues are available from Ribotask A/S.

By the phrase "$C_{1-6}$-alkyl" is meant a linear or branched saturated hydrocarbon chain wherein the longest chains has from one to six carbon atoms, such as methyl, ethyl, n-propyl, isopropyl, n-butyl, isobutyl, sec-butyl, tert-butyl, pentyl, isopentyl, neopentyl and hexyl. A branched hydrocarbon chain is intended to mean a $C_{1-6}$-alkyl substituted at any carbon with a hydrocarbon chain.<<

Specific examples of terminal groups include terminal groups selected from the group consisting of hydrogen, azido, halogen, cyano, nitro, hydroxy, Prot-O—, Act-O—, mercapto, Prot-S—, Act-S—, $C_{1-6}$-alkylthio, amino, Prot-N($R^H$)—, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate including protected monophosphate, monothiophosphate including protected monothiophosphate, diphosphate including protected diphosphate, dithiophosphate including protected dithiophosphate, triphosphate including protected triphosphate, trithiophosphate including protected trithiophosphate, where Prot is a protection group for —OH, —SH and —NH($R^H$), and Act is an activation group for —OH, —SH, and —NH($R^H$), and $R^H$ is hydrogen or $C_{1-6}$-alkyl.

In the present context, the term "$C_{1-4}$-alkyl" is intended to mean a linear or branched saturated hydrocarbon chain wherein the longest chains has from one to four carbon atoms, such as methyl, ethyl, n-propyl, isopropyl, n-butyl, isobutyl, sec-butyl and tert-butyl. A branched hydrocarbon chain is intended to mean a $C_{1-4}$-alkyl substituted at any carbon with a hydrocarbon chain.

When used herein the term "$C_{1-6}$-alkoxy" is intended to mean $C_{1-6}$-alkyl-oxy, such as methoxy, ethoxy, n-propoxy, isopropoxy, n-butoxy, isobutoxy, sec-butoxy, tert-butoxy, pentoxy, isopentoxy, neopentoxy and hexoxy.

In the present context, the term "$C_{2-6}$-alkenyl" is intended to mean a linear or branched hydrocarbon group having from two to six carbon atoms and containing one or more double bonds. Illustrative examples of $C_{2-6}$-alkenyl groups include allyl, homo-allyl, vinyl, crotyl, butenyl, butadienyl, pentenyl, pentadienyl, hexenyl and hexadienyl. The position of the unsaturation (the double bond) may be at any position along the carbon chain.

In the present context the term "$C_{2-6}$-alkynyl" is intended to mean linear or branched hydrocarbon groups containing from two to six carbon atoms and containing one or more triple bonds. Illustrative examples of $C_{2-6}$-alkynyl groups include acetylene, propynyl, butynyl, pentynyl and hexynyl. The position of unsaturation (the triple bond) may be at any position along the carbon chain. More than one bond may be unsaturated such that the "$C_{2-6}$-alkynyl" is a di-yne or enediyne as is known to the person skilled in the art.

Examples of protection groups for —OH and —SH groups include substituted trityl, such as 4,4'-dimethoxytrityloxy (DMT), 4-monomethoxytrityloxy (MMT); trityloxy, optionally substituted 9-(9-phenyl)xanthenyloxy (pixyl), optionally substituted methoxytetrahydro-pyranyloxy (mthp); silyloxy, such as trimethylsilyloxy (TMS), triisopropylsilyloxy (TIPS), tert-butyldimethylsilyloxy (TBDMS), triethylsilyloxy, phenyldimethylsilyloxy; tert-butylethers; acetals (including two hydroxy groups); acyloxy, such as acetyl or halogen-substituted acetyls, e.g. chloroacetyloxy or fluoroacetyloxy, isobutyryloxy, pivaloyloxy, benzoyloxy and substituted benzoyls, methoxymethyloxy (MOM), benzyl ethers or substituted benzyl ethers such as 2,6-dichlorobenzyloxy (2,6-$Cl_2$Bzl). Moreover, when Z or Z* is hydroxyl they may be protected by attachment to a solid support, optionally through a linker.

As indicated above, Z and Z*, which serve for an internucleoside linkage, are independently absent or selected from the group consisting of an internucleoside linkage group, a terminal group and a protection group depending on the actual position of the LNA monomer within the compound. It will be understood that in embodiments where the LNA monomer is located at the 3' end, Z is a terminal group and Z* is an internucleoside linkage. In embodiments where the LNA monomer is located at the 5' end, Z is absent and Z* is a terminal group. In embodiments where the LNA monomer is located within the nucleotide sequence, Z is absent and Z* is an internucleoside linkage group.

Examples of other suitable terminal groups, protecting groups, and particular LNA monomers suitable for use with the present invention can be found, for instance, in U.S. Pat. Publ. 2007/0191294 and references cited therein.

Other nucleotide analogues for use with the present invention, include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics (sugar derivatives) such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 7,335,764, 5,792,747; and 5,700,920 for disclosure relating to making and using such analogues.

Oligomers within the scope of the present invention include those having one or more nucleobase modifications, substitutions, and/or additions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in U.S. Pat. No. 3,687,808, those disclosed in *The Concise Encyclopedia of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

For many invention applications, it will be preferred to have oligomers in which the nucleoside analogue includes at least methylated cytosine to reduce or block unwanted stimulation of the immune system. See the Examples section.

Additional oligomers within the scope of the present invention include those with at least one acyclic nucleotide therein (e.g., 1, 2, 3, or 4), preferably a 3',4"-seco nucleotide analogues such as those disclosed by Neilson, P. Et al. (1994) *NAR* 22:703; And Neilson, P. Et al. (1995) *Bioorganic & Med. Chem.* (1995) 19-28. More specific examples of such acylic nucleotides include 3',4'-secothymidine (seco-RNA-thymidine), 3'4'-secocytosine (seco-RNA-cytosine), 3',4'-secoadenine (seco-RNA-adenine), and 3'-4'-secoguanine (seco-RNA-guanine). The structure of a 3'4'-secocytosine (seco-RNA-cytosine) group is provided below:

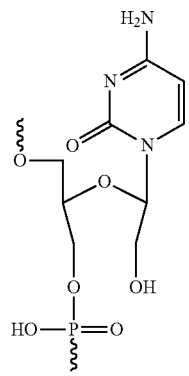

Additional materials for making and using 3',4'-seco nucleic acids can be obtained from Ribotask A/S (Odense, D K). Without wishing to be bound to theory, it is believed that the use of seco-RNA can help increase the utility of certain compositions of the invention including those which rely, at least on part, on enzymatic degradation of nucleic acids, such as siRNA.

Certain of the foregoing nucleobases may be useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar and certain other modifications as disclosed herein such as LNA. See, for instance, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 7,335,764, 5,750,692 and 5,681,941.

While it will often be preferred to use one or a combination of the foregoing invention oligomers in a given application, such compositions can be further modified as desired to suit an intended use. Thus in one embodiment, a particular oligomer of the invention can be chemically linked with one or more moieties or conjugates which enhance the activity, cellular distribution or cellular uptake of the oligonucleotide. The compounds of the invention thus may include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, for example. Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nuci. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nuci. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937. Compounds of the invention, including antisense compounds disclosed herein, may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999), for example. See also, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928, 7,335,764 and 5,688,941, for disclosure relating to making and using such compounds.

As will be appreciated, it will not always be necessary or desirable for all positions in a given compound to be uniformly modified. More than one of the aforementioned modifications may be incorporated in a single compound or even at a single nucleoside within an oligonucleotide. The present invention also includes oligomers which are chimeric compounds. "Chimeric" oligomer compounds, for example, or oligomeric "chimeras," in the context of this invention, are oligonucleotides such as antisense compounds, which contain two or more chemically distinct regions, each made up of at least one monomer unit, i.e., a nucleotide or analogue thereof in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

The term "at least one", as used herein encompasses an integer larger than or equal to 1, such as 1, 2, 3, 4, 5, 6, 7, 8, 9, 10, 11, 12, 13, 14, 15, 16, 17 and so forth.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids, wingmers or gapmers. See, for instance, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922, 7,335,764, and U.S. Pat. Publ. 2007/0191294.

The oligomers used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. Preferably, the oligomers according to the invention are synthesized in vitro and do not include compositions of biological origin, or genetic vector constructs designed to direct the in vivo synthesis of such compositions. Single-stranded oligomers will be preferred for many invention applications.

As discussed, in some invention embodiments it will be useful to enhance the affinity of an oligomer for its target. This can be achieved by one or a combination of methods as disclosed herein. In one approach, the contiguous nucleobase sequence comprises at least one affinity enhancing nucleotide analogue such as those disclosed herein including 2'-MOE and LNA monomers. In one embodiment of an oligomer that includes at least one affinity enhancing nucleotide analogue, the contiguous nucleobase sequence comprises a total of about 2, 3, 4, 5, 6, 7, 8, 9 or about 10 affinity enhancing nucleotide analogues, such as between 5 and 8 affinity enhancing nucleotide analogues. In another embodiment, an oligomer of the invention includes at least one affinity enhancing nucleotide analogue, wherein the remaining nucleobases are selected from the group consisting of DNA nucleotides or RNA nucleotides or acyclic nucleotides as described herein.

In a more specific embodiment of the foregoing oligomers, the oligomer includes a sequence of nucleobases of formula, in 5' to 3' direction, A-B-C, and optionally of formula A-B-C-D in which:

<<A>> consists or includes at least one nucleotide analogue, such as 1, 2, 3, 4, 5 or 6 nucleotide analogues, for example, between 2-5 nucleotide analogues, such as 2, 3 or 4 nucleotide analogues, or 2, 3 or 4 consecutive nucleotide analogues and;

<<B>> consists or comprises at least five consecutive nucleobases which are capable of recruiting RNAseH (when formed in a duplex with a complementary RNA molecule, such as a mammalian C6 target, for instance, the human C6 nucleic acid represented by SEQ ID NO. 1. In one embodiment, the DNA nucleobases of the oligomer such as 5, 6, 7, 8, 9, 10, 11 or 12 consecutive nucleobases which are capable of recruiting RNAseH, or between 6-10, or between 7-9, such as 8 consecutive nucleobases which are capable of recruiting RNAseH, and;

<<C>> consists or comprises of at least one nucleotide analogue, such as 1, 2, 3, 4, 5, or 6 nucleotide analogues, preferably between 2-5 nucleotide analogues, such as 2, 3 or 4 nucleotide analogues, most preferably 2, 3 or 4 consecutive nucleotide analogues, and;

<<D>> when present, consists or comprises, preferably consists, of one or more DNA nucleotides, such as between 1-3 or 1-2 DNA nucleotides.

In one embodiment of the foregoing composition, the oligomer further includes at least one acyclic nucleotide in at least one of A, B, C or D, preferably 1, 2, 3 or 4 of same in region B such as about 1 or about 2 acylic nucleotides. Preferably, the acyclic nucleotide is selected from the group consisting of 3',4'-secothymidine (seco-RNA-thymidine), 3'4'-secocytosine (seco-RNA-cytosine), 3',4'-secoadenine (seco-RNA-adenine), and 3'-4'-secoguanine (seco-RNA-guanine) as described above.

In one embodiment, region A consists or comprises of 2, 3 or 4 consecutive nucleotide analogues. Additionally, B can consist of or include about 7, 8, 9 or about 10 consecutive DNA nucleotides or equivalent nucleobases which are capable of recruiting RNAseH when formed in a duplex with a complementary RNA, such as the mammalian C6 nucleic acid target. Also, C in the above oligomer can consist or include about 2, 3 or about 4 consecutive nucleotide analogues. Region D, as provided above, can consist of, where present, one or two DNA nucleotides. Accordingly, and in one embodiment, region A, as defined above, consists or includes 3 contiguous nucleotide analogues; B, as defined above, consists or includes about 7, 8, 9 or about 10 contiguous DNA nucleotides or equivalent nucleobases which are capable of recruiting RNAseH when formed in a duplex with a complementary RNA, such as the mammalian C6 target; and C, as defined above, consists or includes about 3 contiguous nucleotide analogues; and region D, when present, consists of one or two DNA nucleotides.

In a particular embodiment of the foregoing oligomer, the contiguous nucleobase sequence consists of about 10, 11, 12, 13 or about 14 nucleobases, and wherein; region A consists of about 1, 2 or about 3 contiguous nucleotide analogues; region B consists of about 7, 8, or about 9 consecutive DNA nucleotides or equivalent nucleobases which are capable of recruiting RNAseH when formed in a duplex with a complementary RNA, such as the mammalian C6 nucleic acid target; region C consists of about 1, 2 or about 3 contiguous nucleotide analogues; and region D consists, where present, of one DNA nucleotide.

For many invention applications, it will be generally preferred to have an oligomer in which region B includes at least one LNA monomer (nucleobase). As an example, such an LNA can be in the alpha-L configuration, such as alpha-L-oxy LNA. Additionally suitable nucleotide analogues (whether in one of or all of regions A, B, C and D as defined above) are independently or collectively selected from the group consisting of: Locked Nucleic Acid (LNA) units; 2'-O-alkyl-RNA units, 2'-OMe-RNA units, 2'-amino-DNA units, 2'-fluoro-DNA units, PNA units, HNA units, and INA units. In a preferred invention embodiment, the nucleotide analogue will include and more preferably consist of LNA monomers.

In invention embodiments in which a particular oligomer includes at least one LNA monomer (sometimes called a unit), generally about 1, 2, 3, 4, 5, 6, 7. 8. 9 or 10 LNA units such as between 2 and 8 nucleotide LNA units will be useful. Other LNA monomers will be useful for certain invention applications including those selected from oxy-LNA, thio-LNA, [beta]-D-oxy-LNA, and amino-LNA, in either of the beta-D and alpha-L configurations or combinations thereof. In one embodiment, all the LNA monomers of the oligomer are [beta]-D-oxy-LNA. Thus in a particular invention embodiment, the nucleotide analogues or nucleobases of regions A and C are [beta]-D-oxy-LNA.

As mentioned, and for certain applications, it will be useful to have oligomers that include at least one modified nucleobase. In one embodiment, the modified nucleobase is selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

Practice of the invention is compatible with use of one or a combination of different oligomers as disclosed herein. For example, and in one embodiment, an invention hybridises with a corresponding mammalian C6 nucleic acid (e.g., mRNA) with a $T_m$ of at least 40° C., such as of at least 50° C. In a particular embodiment, the oligomer hybridises with a corresponding mammalian C6 nucleic acid (e.g., mRNA) with a $T_m$ of no greater than 90° C., such as no greater than 80° C.

In most invention embodiments, oligomers with modified backbones as described previously will be generally preferred, especially for in vivo use. In one embodiment, the internucleoside linkages are independently selected from the group consisting of: phosphodiester, phosphorothioate and boranophosphate. In a particular example, the oligomer includes at least one phosphorothioate internucleoside linkage. The internucleoside linkages can be adjacent to or between DNA or RNA units, or within region B (as described above) are phosphorothioate linkages. In one example of an invention oligomer, at least one pair of consecutive nucleotide analogues is a phosphodiester linkage. In some embodiments, all the linkages between consecutive nucleotide analogues will preferably be phosphodiester linkages, for instance, all the internucleoside linkages can be phosphorothioate linkages.

More specific oligomers according to the invention include those targeted to the preferred target sites shown in Tables. 4A-4E and Tables 5A-5F and referred to above. Such oligomers will generally consist of between from about 10 to about 20 nucleotides such as about 12 to about 18 nucleotides, in which the backbone is fully or partially phosphorothiolated. Additionally preferred oligomers will further include between from about one to about six (6) LNA monomers preferably positioned at the 3' and 5' ends of the oligomers. More specific oligomers will include about 2 or 3 of such LNA monomers positioned at each of the ends (ie., wingmers or gapmers).

Also envisioned is any of the forgoing oligomers in which at least one non-nucleotide or non-polynucleotide moiety covalently attached to said compound. Examples include those groups mentioned above.

Additional oligomers of the invention are provided below in the Examples and Tables.

Double-Stranded Compounds

As mentioned, the invention also provides for a double-stranded compound comprising a passenger strand and an antisense strand targeted to a nucleic acid molecule encoding a mammalian complement component 6 (C6) protein such as the human, rat and mouse sequences provided herein. In one embodiment, each strand comprises from between about 12 to about 35 nucleobases, preferably about 12 to about 30 nucleotides, more preferably about 14 to about 25 nucleotides with about 15 to about 20 nucleotides (e.g., 18 or 19 nucleotides) being preferred for many applications. Preferably, the antisense strand consists of a contiguous nucleobase sequence with at least about 80%, 85%, 90%, 95%, 98%, 99% up to about 100% sequence identity to a corresponding region of a nucleic acid which encodes the COMPLEMENT COMPONENT 6 (C6) sequence represented by SEQ ID NOs: 1 (human), 402 (rat) or 403 (mouse) or a naturally occurring allelic variant thereof. Also preferably, the oligomer includes at least one oligonucleotide analogue such as an LNA monomer.

Preferred double-stranded compounds according to the invention can be made using one or a combination of those oligomers disclosed herein. More preferred oligomers are designed to target those preferred target sites already discussed in relation to Tables. 4A-4E and Tables 5A-5F, for example. Additionally preferred oligomers for use with the double-stranded compound will be essentially non-toxic as determined by the animal tests described herein and particularly the Examples section. Such oligomers may additionally show good ability to decrease C6mRNA expression according to the assay.

In one embodiment of the double-stranded compound, one or both of the passenger strand and the antisense strand comprises at least one modified internucleoside linkage as described previously (oligonucleotide backbones) such as a phosphorothioate linkage. In a particular embodiment, all of the internucleoside linkages of the passenger strand and the antisense strand are phosphorothioate linkages. Typically, the passenger strand will additionally include at least one LNA monomer, for instance, between from about 1 to about 10 LNA monomers (e.g. 2, 3, 4, 5, 6, 7, or 9 LNA monomers). In one embodiment, the at least one LNA monomer is located at the 5' end of the passenger strand, for instance, at least two LNA monomers are located at the 5' end of the passenger strand. Alternatively, or in addition, the at least one LNA monomer is located at the 3' end of the passenger strand, for instance, at least two LNA monomers are located at the 3' end of the passenger strand. Additional embodiments of the double-stranded compound include constructs in which the antisense strand comprises at least one LNA monomer, for instance, between from about 1 to about 10 LNA monomers (e.g. 2, 3, 4, 5, 6, 7, or 9 LNA monomers). In one invention example, the at least one LNA monomer of the compound is located at the 3' end of the antisense strand such as embodiments in which at least two LNA monomers are located at the 3' end of the antisense strand, for instance, at least three LNA monomers are located at the 3' end of the antisense strand. However, in other embodiments it may be useful to have 1 or no (0) LNA monomer located at the 5' end of the antisense strand. Double-stranded compounds of the invention include those constructs in which the passenger strand comprises at least one LNA and the antisense strand comprises at least one LNA monomer, for instance, about 1 to about 10 LNA monomers (e.g. 2, 3, 4, 5, 6, 7, or 9 LNA monomers) and the antisense strand comprises about 1 to about 10 LNA monomers (e.g. 2, 3, 4, 5, 6, 7, or 9 LNA monomers).

In one embodiment of the foregoing double-stranded compound comprising the first oligomer (passenger strand) and the second oligomer (antisense strand), the passenger strand comprises at least one LNA monomer at the 5' end (e.g., 1, 2, 3, 4, 5, 6, 7, 8, 9 or 10 LNA monomers) and at least one LNA monomer at the 3' end (e.g., 1, 2, 3, 4, 5, 6, 7, 8, 9 or 10 LNA monomers) such as the embodiment in which the antisense strand comprises at least one LNA monomer at the 3' end. As an example, the passenger strand comprises at least one LNA monomer at the 5' end (e.g., 1, 2, 3, 4, 5, 6, 7, 8, 9 or 10 LNA monomers) and at least one LNA monomer at the 3' end (e.g., 1, 2, 3, 4, 5, 6, 7, 8, 9 or 10 LNA monomers). In a particular embodiment, the antisense strand comprises at least two LNA monomers at the 3' end. In certain embodiments, the passenger strand comprises at least two LNA monomers at the 5' end and at least two LNA monomers at the 3' end, for example, the antisense strand can include at least two LNA monomers at the 3' end. Thus in a particular invention embodiment, the passenger strand comprises at least two LNA monomers at the 5' end and at least two LNA monomers at the 3' end, and, for example, the antisense strand comprises at least three LNA monomers at the 3' end. However in certain invention embodiments it will be useful to have 1 or no (0) LNA monomer is located at the 5' end of the antisense strand.

In a preferred embodiment, T in the composition is replaced by U (T=>U). However, for some or preferably all of the LNA monomers, T will not be replaced by U ie., T=T.

More specific double-stranded compositions are within the scope of the present invention including those in which the passenger strand comprises at least one LNA monomer in at least one of the positions 9-13 counted, sequentially, from the 5' end. For example, the passenger strand can include an LNA monomer in position 10 counted, sequentially, from the 5' end. Alternatively, or in addition the passenger strand can include an LNA monomer in position 11 and/or position 12 therein.

In certain embodiments of the double-stranded compound, the first and the second oligomers therein (passenger and antisense strands) each include between from about 17 to about 25 nucleotides such as 18 to about 24 nucleotides, about 19 to about 23 nucleotides, and about 20 to about 22 nucleotides.

If desired to achieve an invention objective, each of the passenger and antisense strands may independently include a 3' overhang. Alternatively, or in addition, the compound may include at least one (e.g, 1, 2, 3, 4, or 5) acyclic nucleoside located therein e.g., seco-RNA-thymidine, seco-RNA-cytosine, seco-RNA-adenine, and seco-RNA-guanine). In one embodiment, the acylic nucleotide is located on the passenger strand. In another embodiment, the acylic nucleotide is located on the antisense strand of the compound.

In one invention embodiment, the nucleobases of the first oligomer, the second oligomer, or both will be designed hybridize to target exemplified by SEQ ID Nos: 222, 225, 228, 231, 234, 237, 240, 243, 246, and 249 (see Tables. 4A-4E) and RNA and reverse complement versions thereof shown immediately below each target. Rat and mouse C6 is expected to have identical or very similar target sites. Included within the group of such specific oligomers for use as constituents of the double-stranded compounds are derivatives of these sequences in which one or more of the sugar group, nucleobase, or internucleoside linkage, for example, has been modified as disclosed herein. Particular modifications will include modifying the sequence to include or consist essentially of phosphorothioate linkages and at least one LNA monomer.

Accordingly, and in one embodiment, the double-stranded compound features all phosphorothioate linkages and about one, two or three LNA monomers at the 3' end of the antisense strand, for instance, two of same. In one embodiment, the passenger or passenger strand includes one, two, or three LNA monomers at the 5' end of the passenger strand, for instance, two of same.

In some invention embodiments, it may be useful to have more substitution with LNA monomer such as when stronger hybridization between the strands is desirable. Thus in one embodiment, the double-stranded compound features all phosphorothioate linkages and about one, two or three LNA monomers at the 3' end of the antisense strand, for instance, two of same. The passenger strand includes one, two, or three LNA monomers at the 5' end of the passenger strand, for instance, two of same. However in one embodiment, the passenger strand includes an additional one, two, three, four or five LNA monomers between the 3' and 5' end of the passenger strand such as at position 3, 9, 13, and 15 relative to the 5' end (position 1) 3' overhang positions.

Other embodiments of the double-stranded compound as already disclosed herein are possible provided intended results are achieved. For example, both the passenger strand and the antisense strand of the double-stranded compound may include or consist essentially of phosphodiester internucleotide linkages. However, in other embodiments it may be useful to have at least one phosphorothioate internucleotide linkage either in the passenger strand or in the antisense strand or in both strands, for instance, between from about 1 to about 19 phosphorothioate internucleotide linkages (e.g. 2, 3, 4, 5, 6, 7, 8, 9, 10, 11, 12, 13, 14, 15, 16, 17, 18, or 19 phosphorothioate internucleotide linkages). In this example of the invention, position 9-10-11 of the passenger strand, counting from the 5' end is not modified. Additional embodiments of the double-stranded compound include constructs in which the passenger strand includes at least two and up to seven LNA monomers, for instance, at least two LNA monomers are located at the 3' end of the passenger strand. Alternatively, or in addition, at least one LNA monomer is located at the 5' end of the passenger strand. Alternatively, or in addition, at least one or up to four LNA monomers are located at position 3, 9, 13, or 15 counting from the 5' end of the passenger strand. Additional embodiments of the double-stranded compound include constructs in which the antisense strand includes at least one LNA monomer, for instance, between from about 1 to about 3 LNA monomers (e.g. 2, 3, LNA monomers). In one invention example, at least one LNA monomer of the compound is located at the 3' end of the antisense strand such as embodiments in which at least two LNA monomers are located at the 3' end of the antisense strand, for instance, at least three LNA monomers are located at the 3' end of the antisense strand. However, in other embodiments it may be useful to have 1 or no (0) LNA monomer located at the 5' end of the antisense strand.

For example, the following structures are possible (L bold, underlined=LNA, r=RNA):

```
5'rrrrrrrrrrrrrrrrrrrrrLL3'        passenger
3'LLrrrrrrrrrrrrrrrrrrrrr5'        antisense 5'Lrrrrrrrrrrrrrrrrrrrrr LL3'      passenger
3'LLrrrrrrrrrrrrrrrrrrrrrr5'      antisense
```

```
-continued
5'rrLrrrrrLrrrLrLrrrrLL3'          passenger
3'LLrrrrrrrrrrrrrrrrrrrr5'         antisense
``` in which with respect to the structures, the compounds can include at least one optional phosphorothioate, for example, they can be fully phosphorothiolayted. Additional compounds, when a C residue is present, may include an optional methyl C to reduce or eliminate an immune response when used for in vivo applications. Other modifications, as discussed herein are possible.

In a more specific invention embodiment, the following structures are possible in which LNA is represented by bold and underlined text:

```
5'  CUGCAUUGCCAGAAAGUUAGA 3'       passenger
3'  GCGACGUAACGGUCUUUCAAU 5'       antisense 5'  CUGCAUTGCCAGAAAGTUAGA 3'       passenger
3'  GCGACGUAACGGUCUUUCAAU 5'       antisense
```

Other embodiments are possible depending on parameters such as intended use.

Without wishing to be bound to theory, it is believed that in some instances, particular double-stranded compounds of the invention can benefit by having at least one acyclic nucleotide analogue therein, preferably one, two, three or four of same positioned on one or both of the antisense and passenger strands. A preferred acyclic nucleotide is a 3',4'-seco nucleotide as disclosed herein, more preferably 3',4'-secothymidine (seco-RNA-thymidine), 3'4'-secocytosine (seco-RNA-cytosine), 3',4'-secoadenine (seco-RNA-adenine), and 3'-4'-secoguanine (seco-RNA-guanine). In one embodiment, the antisense strand includes 1 acyclic nucleotide, preferably positioned between the 3' and 5' ends, for instance, between from about 3 to about 20 nucleotides from the 3' end, preferably between from about 5 to about 19 nucleotides from the 3' end. In one embodiment, the antisense stand further includes one, two, or three LNA monomers, for instance, two of same positioned at the 3" end. The passenger strand, in one embodiment, includes one, two or three acyclic nucleotides at the 3' end, preferably one of same.

In one embodiment, the following compound is possible (L bold, underlined=LNA, r=RNA, S underlined italic=seco):

```
5'  rrrrrrrrrrrrrrrrrrrrrS 3'      passenger
3'  LLrrrrrrrrrrrrrrSrrrrr 5'      antisense
``` in which the compound can include at least one optional phosphorothioate, for example, it can be fully phosphorothiolayted. Additional compounds, when a C residue is present, may include an optional methyl C to reduce or eliminate an immune response when used for in vivo applications. Other modifications, as discussed herein are possible.

Thus in one embodiment, the following compound is within the scope of the invention in which underlined/italicized text is a seco derivative and bold and underlined text is LNA:

```
5'  CUGCAUUGCCAGAAAGUUAGA 3'       passenger
3'  GCGACGUAACGGUCUUUCAAU 5'       antisense
```

Particular invention compounds will sometimes be referred to herein as "siLNA" to denote broadly a compound with at least one LNA monomer. As used herein, the term "siRNA" refers to a double stranded stretch of RNA or modified RNA monomers. In a typical siRNA compound, the two strands usually have about 19 nucleotides complementary to each other thereby creating a double strand that is about 19 nucleotides long and each strand having a 3'-end of two overhanging nucleotides. It will be appreciated that an siRNA of the invention may be slightly longer or shorter, and with or without overhangs. Choice of a particular siRNA construct will depend on recognized parameters such as intended use. In siRNA, one oligomer strand is guiding and complementary to the target RNA (antisense strand), and the other oligomer strand (passenger strand) has the same sequence as the target RNA and hence is complementary to the guiding/antisense strand. Herein, regulatory RNAs such as "micro RNA" ("miRNA") and "short RNA" ("shRNA") and a variety of structural RNAs such as tRNA, snRNA, scRNA, rRNA are used interchangeably with the term "siRNA". The term "mRNA" means the presently known mRNA transcript(s) of a targeted gene, and any further transcripts, which may be identified.

Such double-stranded compounds according to the invention can be conjugated (ie. covalently bound) to at least one non-nucleotide or non-polynucleotide moiety. Examples include those described previously.

As will be appreciated, to be stable in vitro or in vivo the sequence of an siLNA or siRNA compound need not be 100% complementary to its target nucleic acid. The terms "complementary" and "specifically hybridisable" thus imply that the siLNA or siRNA compound binds sufficiently strong and specific to the target molecule to provide the desired interference with the normal function of the target whilst leaving the function of non-target mRNAs unaffected Discontinuous Strand RNA Complexes In another aspect, the present invention provides for a composition comprising a nucleic acid complex, typically comprising or consisting of RNA or one or more oligonucleotide analogues thereof, and preferably a pharmaceutically acceptable diluent, carrier, or adjuvant. In one embodiment, the complex includes a core double-stranded region that includes an antisense strand consisting of a contiguous nucleobase sequence with at least about 80% sequence identity, at least about 85%, 90%, 95%, 98%, 99%, up to about 100% sequence identity to a corresponding region of a nucleic acid which encodes the complement component 6 (C6) sequence represented by SEQ ID NOs: 1 (human), 402 (rat) or 403 (mouse) or a naturally occurring allelic variant thereof. Preferred complexes include at least one oligonucleotide analogue, the RNA complex further comprising a discontinuous passenger strand that is typically hybridised to the antisense strand. For most applications, the discontinuous passenger strand includes a discontinuity such as a nick or a gap or a linker or other such interruption as described herein.

In one embodiment of the foregoing, the RNA complex is generally capable of mediating nucleic acid modifications of a corresponding target nucleic acid. Preferably, the nucleic acid modification is selected from one or more of the group consisting of RNA interference, gene-silencing, gene-suppression, translation arrest, translation inhibition, RNA degradation, RNA cleavage and DNA methylation. Typical RNA complexes mediate degradation of a target RNA or mediate translational inhibition of a target RNA or a combination of both.

In a particular RNA complex of the invention, the core double-stranded region includes between about 15 to about 40 base pairs such as 18 base pairs, 19 base pairs, 20 base pairs, 21 base pairs, 22 base pairs and 23 base pairs. In one embodiment, the RNA complex includes one or more overhangs, for instance, one or two overhangs. An example of an overhang is a 3'-overhang. In one embodiment, the passenger of the RNA complex comprises the 3'-overhang.

Although a variety of overhang lengths are compatible with the invention, generally the length of the overhang is between about 1 and about 8 nucleotides such as 1 nucleotide, 2 nucleotides and 3 nucleotides. RNA complexes in accord can include at least one blunt end including having both ends blunt ended. The length of the RNA complex can be nearly any length sufficient to achieve intended results including between about 18 to about 22 base pairs. In this embodiment, it is preferred that the antisense strand and the passenger strand each include a 3'-overhang of between about 1 to about 3 nucleotides.

As mentioned, particular RNA complexes of the invention include a discontinuous passenger strand. In one embodiment, the complex includes at least a first and a second RNA-molecule, which together, optionally with one or more further RNA molecules, form the discontinuous passenger strand. Preferably, the first RNA molecule is hybridised to the downstream part of the antisense strand and the second RNA molecule is hybridised to the upstream part of the antisense strand. In one embodiment, the passenger strand comprises between about 1 to about 4 further RNA molecules, which together with the first and second RNA-molecules preferably form the discontinuous passenger strand. In another embodiment, the passenger strand includes only the first and second-RNA molecules, and, for example, no further RNA molecules.

A discontinuity on the passenger strand can be formed, for instance, by a nick or nicks in which the at least first and second RNA molecules, and optionally the further RNA molecules of the passenger strand are separated thereby. If desired however, the at least first and second RNA molecules and optionally said further RNA molecules of the passenger strand are separated by a gap, or optionally gaps, such as those selected from the group consisting of: a 1 nucleotide gap, a 2 nucleotide gap, a 3 nucleotide gap, a 4 nucleotide gap, a 5-nucleotide gap, a 6-nucleotide gap, a 7-nucleotide gap, an 8-nucleotide gap, a 9-nucleotide gap, a 10-nucleotide gap, an 11-nucleotide gap and a 12-nucleotide gap. In embodiments in which the discontinuity is related to a linker, the first RNA molecule of the passenger strand can be connected to the antisense strand by the linker. In one embodiment, the linker connects the 5' end of the first RNA molecule of the passenger strand to the 3' end of the antisense strand. In another embodiment, the second RNA molecule of the passenger strand can be connected to the antisense strand by the linker. If desired, the linker can connect the 3' end of the second RNA molecule of the passenger strand to the 5' end of the antisense strand. The at least first and the second RNA molecules of the passenger strand, and optionally said further RNA molecules of the passenger strand can be connected by the linker, or optionally a plurality of linkers. A variety of linkers are compatible with the invention such as those which are not a single stranded RNA linker.

In some invention embodiments of the RNA complex, the antisense strand is not covalently linked to the passenger strand. If desired, the RNA molecules which form the discontinuous passenger strands are not covalently linked to any other of the RNA molecules which form the discontinuous passenger strands.

Certain RNA complexes according to the invention feature three non-linked RNA molecules, namely the antisense strand, and the first and the second RNA molecules which together form the discontinued passenger strand. In one embodiment, the discontinued passenger strand has a discontinuity at a position selected from the group of: position 3, position 4, position 5, position 6, position, position 7, position 8, position 9, position 10, position 11, position 12, position 13, position 14, position 15 position 16, position 17, position 18, position 19, position 20, position 21, position 22, position 23, position 24, position 25. Preferably, the position is calculated in the 5' to 3' direction from the first nucleotide of the passenger strand base paired to the antisense strand in the of the passenger strand.

For some invention embodiments, it will be useful to have an RNA complex in which the 5-ends of the RNA complex are either phosphorylated or available for phosphorylation. In one embodiment, the first RNA molecule comprises a 5'-end phosphate group and a 3'-end hydroxy group. In another embodiment, the second RNA molecule comprises a 5'-end phosphate group and a 3'-end hydroxy group. In certain embodiments, all the RNA molecules which form the discontinuous passenger strand each comprise a 5'-end phosphate group and a 3'-end hydroxy group.

It will often be useful to have RNA complexes that include or in some cases consist of at least one nucleotide analogue such as those disclosed herein. In one embodiment, the passenger strand of the RNA complex comprises at least one nucleotide analogue such as between 2 and 10 nucleotide analogues. Alternatively, or in addition, the first RNA molecule of the passenger strand comprises one or more nucleotide analogues such as at least 2 nucleotide analogues. Alternatively, or in addition, the second RNA molecule of the passenger strand comprises one or more nucleotide analogue such as at least 2 nucleotide analogues.

In embodiments in which an RNA complex includes a nucleotide analogue, the location of the analogue is preferably within the three terminal (5' or 3' respectfully) nucleobase units of the first and/or second RNA molecule. Alternatively, or in addition, at least one of the further RNA molecules of the passenger strand comprise at least one nucleotide analogue. For instance, each further RNA molecule which forms part of the discontinuous passenger strand comprises at least one nucleotide analogue such as at positions 10 and 12 from the 5' end of the passenger strand. In one embodiment, each RNA molecule which forms part of the discontinuous passenger strand and comprises at least one nucleotide analogue, such as at least two nucleotide analogues.

In one embodiment, the passenger strand includes an additional one, two, three, four or five LNA monomers between the 3' and 5' end of the passenger strand such as at position 3, 9, 13, and 15 relative to the 5' end (position 1) and the 3' overhang positions. However in this example of the invention, the passenger strand is broken in two parts, for instance, between positions 10 and 11. Thus in one embodiment, each portion of the passenger strand includes at least one LNA monomer, for instance, one, two, three, four, five, six or seven of same, more preferably five or six of same in which one, two, or three, or four LNA monomers are position on one of the passenger strands and the remaining monomers positioned on the other strand.

It will often be useful to make and use an RNA complex that has desirable melting temperature properties. Thus in one embodiment, the melting temperature ($T_m$) for each of the first, second and optionally further RNA molecules which form the discontinuous passenger strand, when formed in a duplex with a complementary RNA molecule with phosphodiester linkages is at least 40° C.

Preferred lengths of the RNA complexes of the invention will be guided by intended use. Thus in one embodiment, the length of each of the first, second and optionally further RNA molecules which form the discontinuous passenger strand is at least three nucleobase units. In one embodiment, the antisense strand comprises at least 1 nucleotide analogue such as the example where the antisense strand comprises at least 1 nucleotide analogue within the duplex region formed with the discontinuous passenger strand. Alternatively, or in addition, the antisense strand comprises at least one nucleotide analogue at a position which is within 4 nucleobases as counted from the 3' end of the antisense strand. In one embodiment, at least one of the nucleobases present in about the 9 5' most nucleobase units of the antisense strand is a nucleotide analogue. In another embodiment, at least one of the nucleobases present in the region within 4-10 nucleobases from the 3' end of the antisense strand is a nucleotide analogue. In yet another embodiment, the antisense strand has a nucleotide analogue at position 11 from the 5' end of the antisense strand. In yet another embodiment, the antisense strand has RNA nucleotides at position 10 and 12 from the 5' end of the antisense strand. In other embodiment, the 5' most nucleobase units of the antisense strand is an RNA nucleotide unit. Alternatively, or in addition, the antisense strand comprises at least 2 nucleotide analogues.

A wide variety of nucleotide analogues are compatible with the invention. Typically suitable analogues are those that are or are suspected of being compatible with the formation of an A-form or A/B for conformation of the RNA complex. Illustrative analogues include the group consisting of: 2'-O—alkyl-RNA monomers, 2'-amino-DNA monomers, 2'-fluoro-DNA monomers, LNA monomers, arabino nucleic acid (ANA) monomers, 2'-fluoro-ANA monomers, HNA monomers, INA monomers. A preferred nucleotide analogue is present in discontinuous passenger and/or antisense strand and consists of at least one LNA monomer such as those already disclosed herein. Alternatively, or in addition, the nucleotide analogues present in the discontinuous passenger and/or antisense strand include at least one 2'-MOE-RNA (2'-O-methoxyethyl-RNA) unit or 2'Fluoro DNA unit, such as between about 1 and about 25 units independently selected from either 2'-MOE-RNA (2'-O-methoxyethyl-RNA) units or 2'Fluoro DNA units.

As mentioned, it will often useful to have an RNA complex in which at least one nucleotide is substituted with at least one LNA unit. In one embodiment, the LNA unit or units are independently selected from the group consisting of oxy-LNA, thio-LNA, and amino-LNA, in either of the D-β and L-α configurations or combinations thereof. If desired, the nucleotide analogues present in the antisense strand include at least one LNA unit and/or the nucleotide analogues present in the passenger strand include at least one LNA unit. In one embodiment, the nucleotide analogues present in antisense strand are LNA units. Alternatively, or in addition, all the nucleotide analogues present in passenger strand are LNA units. Various preferred LNA monomers have been disclosed above.

In many embodiments of the RNA complex described herein, at least one of the nucleotide analogues present in the discontinuous passenger strand forms a base pair with a complementary nucleotide analogue present in the antisense strand. In one embodiment, the passenger strand does not comprise any nucleotide analogues and/or in another embodiment the antisense strand does not comprise any nucleotide analogues. In another embodiment, the antisense strand and discontinuous strand form a complementary duplex of between about 18 to about 22 base pairs. In one embodiment, the duplex may comprise a mismatch.

In one embodiment the number of nucleotide analogues present in the antisense strand or passenger strand (or both, either as separate entities or as a combined total of nucleotide analogues within the RNA complex) is selected from the group consisting of: at least one nucleotide analogue, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20, at least 21, at least 22, at least 23, at least 24 and at least 25 nucleotide analogues. Suitably the number of nucleotide analogues may be less than 20, such as less than 18, such as less than 16, such as less than 14, such as less than 12, such as less than 10.

In one embodiment the nucleotide analogues present in discontinuous passenger strand (or antisense strand, or both, either as separate entities or as a combined total of nucleotide analogues within the RNA complex) include at least one 2'-O-alkyl-RNA monomer (such as 2'OME), such as 1, 2, 3, 4, 5, 6, 7, 8, 9, 10, 11, 12, 13, 14, 15, 16, 17, 18, 19, 20, 21, 22, 23, 24 or 25 2'-O-alkyl-RNA monomers (such as 2'OME). Complexes comprising or consisting of 2'OME and LNA are also envisioned.

In one embodiment, which may be the same of different, the nucleotide analogues present in discontinuous passenger strand (or antisense strand, or both, either as separate entities or as a combined total of nucleotide analogues within the RNA complex) include at least one 2'-fluoro-DNA monomer, such as 1, 2, 3, 4, 5, 6, 7, 8, 9, 10, 11, 12, 13, 14, 15, 16, 17, 18, 19, 20, 21, 22, 23, 24 or 25 2'-fluoro-DNA monomers.

For many invention applications it will generally be preferred to have at least one LNA monomer present in discontinuous passenger strand. In one embodiment, which may be the same of different, the nucleotide analogues present in discontinuous passenger strand (or antisense strand, or both, either as separate entities or as a combined total of nucleotide analogues within the RNA complex) include at least one LNA monomer, such as 1, 2, 3, 4, 5, 6, 7, 8, 9, 10, 11, 12, 13, 14, 15, 16, 17, 18, 19, 20, 21, 22, 23, 24 or 25 LNA monomers.

In one embodiment the LNA unit or units are independently selected from the group consisting of oxy-LNA, thio-LNA, and amino-LNA, in either of the D-β and L-α configurations or combinations thereof. In one embodiment the nucleotide analogues present in the antisense strand include at least one Locked Nucleic Acid (LNA) unit, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 LNA units. Suitable the number of LNA units may be less than 20, such as less than 18, such as less than 16, such as less than 14, such as less than 12, such as less than 10. In one embodiment all the nucleotide analogues present in antisense strand are Locked Nucleic Acid (LNA) units.

In a another embodiment, the antisense strand only comprises a few nucleotide analogue units, such as LNA units. Typically it is preferred the nucleotide units present in the antisense strand a positioned within the 3' half of the antisense strand such as between positions 1 and 9 of the antisense strand, such as position 1, 2, 3, 4, 5, 6, 7, 8, or 9 of the antisense strand, such as within the region of a 3 over-hang, or within the first 3, such first, second or third, nucleobase positions of the duplex as measured from the 3' end of the antisense strand.

In one embodiment the nucleotide analogues present in the passenger strand (or antisense strand, or both, either as separate entities or as a combined total of nucleotide analogues within the RNA complex) include at least one LNA unit such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 LNA units. Suitable the number of LNA units may be less than 20, such as less than 18, such as less than 16, such as less than 14, such as less than 12, such as less than 10. In one embodiment all the nucleotide analogues present in passenger strand are Locked Nucleic Acid (LNA) monomers (units).

In one embodiment at least one of the nucleotide analogues present in the discontinuous passenger strand forms a base pair with a complementary nucleotide analogue present in the antisense strand.

In one embodiment all the nucleotide analogues present in the discontinuous passenger strand forms a base pair with a complementary nucleotide analogue present in the antisense strand, other than those nucleotide analogue present in the 3' overhang (if present).

In one embodiment all the nucleotide analogues present in the antisense strand forms a base pair with a complementary nucleotide analogue present in the discontinuous passenger strand, other than those nucleotide analogue present in the 3' overhang (if present). In one embodiment the passenger strand consists or comprises of a 9-11 nucleotide (nucleobase) RNA molecule, such as a 10 nucleotide RNA molecule, with between 1 and five nucleotide analogues, such as LNA units, such as two LNA units and a 11-13 nucleotide RNA molecule, such as a 12 nucleotide RNA molecule, comprising between 1 and 5 nucleotide analogue units, such as LNA units, such as three LNA residues.

By way of example, and not limitation, the following particular invention complex has the following structure in which bold and underlined text is LNA:

```
5' CUGCAUTGCC 3' 5'AGAAAGTUAGA 3'    passenger
3' GCGACGUAACGGUCUUUCAAU 5'          antisense
```

Further disclosure relating to making and using the RNA complexes of the invention (sometimes called sisiRNA) can be found in the following: WO2007/107162 (PCT/DK2007/000146), PA 2006 00433 (DK), and PA 2006 01254 (DK) for disclosure related to making and using such complexes.

Practice of the present invention can be achieved by using one or a combination of the RNA complexes disclosed herein. In one embodiment, the RNA complex has reduced off-target effects as compared to a native RNA complex comprising a non-modular passenger strand. In one embodiment, the RNA complex produces a reduced immune response as compared to a native RNA complex comprising a non-modular passenger strand. In another embodiment, the RNA complex has a prolonged effect on target nucleic acids as compared to an RNA complex comprising a non-modular passenger strand. Thus in one embodiment, the RNA complex has an increased effect on its target nucleic acid as to compared to an RNA complex comprising a non-modular passenger strand. A preferred target nucleic acid is the C6 sequence disclosed as SEQ ID NO: 1 (human), SEQ ID NO:402 (rat), or SEQ ID NO: 403(mouse).

The RNA complexes of the invention can be made by one or a combination of strategies. In one approach, the method includes incubating an antisense strand with the at least two RNA molecules which form a discontinuous passenger strand, and optionally further RNA molecules of the passenger strand under conditions wherein a RNA complex comprising a core double stranded region is formed. Preferably, the RNA complex is capable of mediating RNA interference of a corresponding cellular RNA, wherein either said incubation occurs within a pharmaceutically acceptable diluent, carrier, or adjuvant, or said RNA complex is subsequently admixed with a pharmaceutically acceptable diluent, carrier, or adjuvant.

The foregoing RNA complexes have a variety of uses. In one embodiment, the invention features use of an RNA complex as defined herein for the manufacture of a medicament for the treatment of a disease associated with undesired formation of a membrane attack complex (MAC) such as those mentioned below.

Also provided is a method for treating, preventing or reducing onset of the disease or reducing symptoms thereof in a patient, the method comprising administering one or more of the RNA complexes disclosed herein preferably in combination with a pharmaceutically acceptable, buffer, adjuvant, or vehicle as described herein.

The present invention also features a method of reducing the level of a target RNA (or gene expression) in a cell or an organism comprising contacting the cell or organism with at least one RNA complex as defined herein sufficient to modulate that gene expression. Preferably, the antisense strand of the RNA complex is essentially complementary to a region of the target RNA.

As discussed, an RNA complex suitable for use with the invention can include at least one nucleotide analogue. In one embodiment, the first RNA molecule of the passenger strand does not comprise a 2'-O-methyl ribose at position 9 from the 5' end. In another embodiment, the first RNA molecule of the passenger strand does not comprise a 2'-O-methyl ribose at position 9 from the 5' end.

Also provided by the present invention is a method of mediating nucleic acid modifications of a target nucleic acid in a cell or an organism preferably comprising at least one of and preferably all of the steps:
  a. contacting said cell or organism with the RNA complex as defined herein and under conditions wherein target specific nucleic acid modifications can occur, and
  b. mediating a target specific nucleic acid modification guided by the antisense strand of the RNA complex.

In one embodiment of the foregoing method, the step of mediating nucleic acid modifications is selected from the group consisting of RNA interference, gene-silencing, RNA degradation, RNA cleavage and DNA methylation.

The invention also provides a method of examining the function of a gene in a cell or organism comprising:
  a. introducing an RNA complex as defined herein that targets the RNA encoded by the gene, such as an mRNA or other functional RNA, for degradation or silencing or suppression into the cell or organism, thereby producing a test cell or test organism,
  b. maintaining the test cell or test organism under conditions under which degradation or silencing or suppression of the RNA encoded by the gene occurs, thereby producing a test cell or test organism in which mRNA levels of the gene is reduced, and
  c. observing the phenotype of the test cell or organism produced in step b and optionally comparing the observed phenotype with the phenotype of an appropriate control cell or control organism, thereby providing information about the function of the gene.

Practice of the invention provides important advantages particularly in embodiments in which an invention compound (e.g., antisense, siRNA, sisiRNA) includes an LNA monomer.

For example, one advantage of embodiments in which a compound of the invention includes an LNA monomer (e.g., antisense compound, siLNA, sisiLNA) is their improved stability in biological fluids, such as serum. Thus, one embodiment of the invention includes the incorporation of LNA monomers into a standard DNA or RNA oligonucleotide to increase the stability of the resulting siLNA compound or antisense oligomer in biological fluids e.g. through the increase of resistance towards nucleases (endonucleases and exonucleases). Accordingly, the compounds of the invention will, due to incorporation of LNA monomers, exhibit an increased circulation half-life as a result of its increased melting temperature and/or its increased nuclease resistance. The extent of stability will depend on the number of LNA monomers used, their position in the oligonucleotides and the type of LNA monomer used. Compared to DNA and phosphorothioates the following order of ability to stabilise an oligonucleotide against nucleolytic degradation can be established: DNA<<phosphorothioates, LNA-phosphordiester<LNA-phosphorothioates.

For many applications, preferred compounds according to the invention include compounds which, when incubated in serum (e.g. human, bovine or mice serum), such as in 10% foetal bovine serum in a physiological salt solution at 37° C. for 5 hours, are degraded to a lesser extent than the corresponding ssDNA, ssRNA or dsRNA compound. Preferably, less than 25% of the initial amount of the compound of the invention is degraded after 5 hours, more preferably less than 50% of the initial amount of the compound of the invention is degraded after 5 hours, even more preferably less than 75% of the initial amount of the compound of the invention is degraded after 5 hours. In another embodiment, it is preferred that less than 25% of the initial amount of the compound of the invention is degraded after 10 hours, and even more preferred that less than 50% of the initial amount of the compound of the invention is degraded after 10 hours.

As will be apparent from the foregoing, compounds of the invention may include one or more LNA monomers alone or in combination with nucleotides that are either naturally-occurring or nucleotide analogues. Such other residues may be any of the residues discussed herein and include, for example, native RNA monomers, native DNA monomers as well as nucleotide variants and analogues such as those mentioned in connection with the definition of "nucleotide" above. Specific examples of such nucleotide variants and analogues include, 2'-F, 2'-O-Me, 2'-O-methoxyethyl (MOE), 2'-O-(3-aminopropyl) (AP), hexitol nucleic acid (HNA), 2'-F-arabino nucleic acid (2'-F-ANA) and D-cyclohexenyl nucleoside (CeNA). Furthermore, the internucleoside linkage may be a phosphorodiester, phosphorothioate or N3'-P5' phosphoroamidate internucleoside linkages as described above.

In general, the individual strands of the compounds of the invention that include one or more LNA monomers will contain at least about 5%, at least about 10%, at least about 15% or at least about 20% LNA monomer, based on total number of nucleotides in the strand. In certain embodiments, the compounds of the invention will contain at least about 25%, at least about 30%, at least about 40%, at least about 50%, at least about 60%, at least about 70%, at least about 80% or at least about 90% LNA monomer, based on total number of nucleotides in the strand.

Compounds of the invention can be manufactured using techniques disclosed herein including syntheses provided by U.S. Pat. Publication No. 2007/0191294 and WO2007/107162.

Pharmaceutical Compositions and Administration

A preferred use of the compounds of the invention will be as drugs for the treatment, prevention, and/or alleviation of symptoms associated with acute or chronic neuropathy. The design of a potent and safe drug often requires the fine-tuning of diverse parameters such as affinity/specificity, stability in biological fluids, cellular uptake, mode of action, pharmacokinetic properties and toxicity. These and other parameters will be known to the art-skilled.

Accordingly, in a further aspect the present invention relates to a pharmaceutical composition comprising a compound according to the invention and a pharmaceutically acceptable diluent, carrier or adjuvant.

In a still further aspect the present invention relates to a compound according to the invention for use as a medicament.

As will be understood, dosing is dependent on severity and responsiveness of the neuropathy to be treated and the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual invention compounds and/or the indication to be treated (see below). Generally it can be estimated based on $EC_{50}$s found to be effective in in vitro and in vivo animal models. In general, dosage is from 0.01 micrograms to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state.

As will be appreciated, the present invention also features a pharmaceutical composition, which comprises at least one compound of the invention (eg., antisense compound, siLNA, siRNA, sisiLNA) as an active ingredient. It should be understood that the pharmaceutical composition according to the invention optionally comprises a pharmaceutical carrier, and that the pharmaceutical composition optionally comprises further compounds, such as anti-inflammatory compounds (e.g., non-steroid and steroid anti-inflammatory agents) and/or immuno-modulating compounds.

A compound of the invention can be employed in a variety of pharmaceutically acceptable salts. As used herein, the term refers to salts that retain the desired biological activity of the herein-identified compounds and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine.

In one embodiment of the invention the invention compound may be in the form of a pro-drug. Oligonucleotides are by virtue negatively charged ions. Due to the lipophilic nature of cell membranes the cellular uptake of oligonucleotides are reduced compared to neutral or lipophilic equivalents. This polarity "hindrance" can be avoided by using the pro-drug approach (see e.g. Crooke, R. M. (1998) in Crooke, S. T. *Antisense research and Application*. Springer-Verlag, Berlin, Germany, vol. 131, pp. 103-140). In this approach the oligonucleotides are prepared in a protected manner so that the oligo is neutral when it is administered. These protection groups are designed in such a way that they can be removed when the oligo is taken up by the cells. Examples of such protection groups are S-acetylthioethyl (SATE) or S-pivaloylthioethyl (t-butyl-SATE). These protection groups are nuclease resistant and are selectively removed intracellularly.

Pharmaceutically acceptable binding agents and adjuvants may comprise part of the formulated drug. Capsules, tablets and pills etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils. Likewise coatings of sugar or enteric agents may be part of the dosage unit. The invention compounds may also be emulsions of the active pharmaceutical ingredients and a lipid forming a micellular emulsion. A compound of the invention may be mixed with any material that do not impair the desired action, or with material that supplement the desired action. These could include other drugs including other nucleotide compounds. For parenteral, subcutaneous, intradermal or topical administration the formulation may include a sterile diluent, buffers, regulators of tonicity and antibacterials. The active compound may be prepared with carriers that protect against degradation or immediate elimination from the body, including implants or microcapsules with controlled release properties. For intravenous administration the preferred carriers are physiological saline or phosphate buffered saline.

Preferably, an invention compound is included in a unit formulation such as in a pharmaceutically acceptable carrier or diluent in an amount sufficient to deliver to a patient a therapeutically effective amount without causing serious side effects in the treated patient.

The pharmaceutical compositions of the present invention may be administered in a number of ways depending upon whether local or systemic treatment is desired and upon the area to be treated. Administration may be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration. In one embodiment the pharmaceutical composition is administered IV, IP, orally, topically or as a bolus injection or administered directly in to the target organ. Pharmaceutical compositions and formulations for topical administration may include transdermal patches, ointments, lotions, creams, gels, drops, sprays, suppositories, liquids and powders. Conventional pharmaceutical carriers, aqueous, powder or oily bases, thickeners and the like may be necessary or desirable. Coated condoms, gloves and the like may also be useful. Preferred topical formulations include those in which the compounds of the invention are in admixture with a topical delivery agent such as lipids, liposomes, fatty acids, fatty acid esters, steroids, chelating agents and surfactants. Compositions and formulations for oral administration include but is not restricted to powders or granules, microparticulates, nanoparticulates, suspensions or solutions in water or non-aqueous media, capsules, gel capsules, sachets, tablets or minitablets. Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to tumour tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. *J Pharm Pharmacol* 2002; 54(1):3-27). The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances which increase the viscosity of the suspension including, for example, sodium carboxymethyl-cellulose, sorbitol and/or dextran. The suspension may also contain stabilizers. The compounds of the invention may also be conjugated to active drug substances, for example, aspirin, ibuprofen, a sulfa drug, an antidiabetic, an antibacterial or an antibiotic. Other useful conjugates have been disclosed above.

Diluents, carriers, and buffers that render an oligonucleotide orally available to a mammal such as a rodent or human patient are within the scope of the present invention. A particular example of such a carrier is a caprate salt, for example, sodium caprate. See Tillman, L G et al. (2008) *J. of Pharmaceutical Sciences*, January 97(1) 225; Gonzalez, F M et al. (2003) *Eur. J. Pharm. Biopharm*, January: 55(1): 19-26; Aouadi, M et al. (2009) *Nature* 458: 1180; and references disclosed therein for information relating to making formulations suitable for orally administering an oligonucleotide.

It will be appreciated that a particular formulation or administration route of the invention may include a single invention compound as the sole active agent. However, in other invention embodiments, the formulation or administration route includes two or more invention compounds such as 2, 3, 4, 5, 6 7, 8, 9, or 10 of such compounds. Generally, the number of invention compounds employed will be less than 5, such as one, two or three. For example, such a formulation or administration may contain one or more siLNA or sisiLNA compounds, targeted to a first nucleic acid and one or more additional siLNA or sisiLNA compounds targeted to a second nucleic acid target. Two or more combined compounds may be used together or sequentially.

The compounds of the invention are useful for a number of therapeutic applications as indicated above. In general, therapeutic methods of the invention include administration of a therapeutically effective amount of a desired compound (or one or more compounds such as 1, 2, 3, or 4 of same) to a mammal, particularly a human. In a certain embodiment, the present invention provides pharmaceutical compositions containing (a) one or more compounds of the invention, and (b) one or more other agents such as anti-inflammatory agents or complement antagonists such as those disclosed herein. When used with the compounds of the invention, such compositions and agents may be used individually, sequentially, or in combination with one or more other such compositions and agents including other therapies including those accepted for the prevention or treatment of acute or chronic neuropathies.

The compounds of the present invention can be utilized for as research reagents for diagnostics, therapeutics and prophylaxis. In research, the compound may be used to specifically inhibit the synthesis of target genes in cells and experimental animals thereby facilitating functional analysis of the target or an appraisal of its usefulness as a target for therapeutic intervention. In one embodiment, the oligomers, siRNA and sisiRNA compositions of the invention may be used to detect and quantitate target expression in cell and tissues by Northern blotting, in-situ hybridisation or similar techniques. For therapeutics, an animal or a human, suspected of having a disease or disorder, which can be treated by modulating the expression of target is treated by administering the compounds in accordance with this invention. Further provided are methods of treating an animal particular mouse and rat and treating a human, suspected of having or being prone to a disease or condition, associated with expression of target by administering a therapeutically or prophylactically effective amount of one or more of the compounds or compositions of the invention.

Nerve Regeneration

As discussed, the present invention further provides for a method for treating, preventing or reducing symptoms of a disorder mediated by undesired activity of the complement system. In one embodiment, the method includes administering at least one compound of the invention, particularly at least one pharmaceutical composition as described herein to a mammal (e.g, a primate or non-primate mammal, especially a human patient) in need thereof. By the phrase <<disorder mediated by undesired activity of the complement system>> is meant a neuronal disorder manifested in whole or in part by an inability or insufficiency in nerve regeneration. Examples of such disorders include those manifesting an inability or insufficiency in nerve regeneration following acute or chronic injury to nerves in the peripheral nervous system (PNS) or central nervous system (CNS). An inability or insufficiency to regenerate nerves (or to improve the function of damaged nerves can be detected and in some cases quantified by tests known in the field. See e.g., Ramaglia, V. et al. (2007) *J. Neurosci.* 27:7663 (describing, among other things, assays to detect and optionally quantify nerve degeneration and regeneration in rats); Wolf, S L (2001) *Stroke* 32:1635 (motor function test); S. Van Tuijl, et al. (2002) *Spinal Cord* 40:51 (motor function test); Sheikh, K et al. (1980) *Rheumatology* 19:83 (motor function test); Chan A. We et al. (2001) *J. Neurol. Neurosurg. Psychology* 55:56 (sensory function test); and Mayuko. W et al. (2005) *J. Jap. Soc. For Surgery of the Hand* (2005) 22:842 (multiple sensory function tests); and references cited therein.

Methods for monitoring an improvement in axonal regeneration have been described and generally include various functional tests that can be conducted in human patients. Such tests generally monitor recovery of sensory and/or motor function such as the Weinstein Enhanced Sensory Test (WEST), Semmes-Weinstein Monofilament Test (SWMT) and others. See WO2008/044928 (PCT/NL2007/050490), Ristic S, et al. (2000) *Clin Orthop Relat Res.* 370:138; and references cited therein for methods for detecting and monitoring neuronal regeneration and for methods of classifying various neuronal insults. The appropriate dose of a compound of the invention is one that can be shown to promote axonal regeneration according to these or other acceptable tests as described herein. By <<effective dose>>, <<therapeutic amount>> or related phrase is meant that amount sufficient to achieve a desired therapeutic outcome as determined by these or other acceptable tests.

Compositions and methods of the invention can be used to prevent, treat, or reduce symptoms associated with an acute or chronic nerve injury. Conditions requiring axonal regeneration, whether acute or chronic, have been disclosed, for instance, in WO2007/044928 and references cited therein. Acute trauma to peripheral nerves is relatively common including blunt trauma or from penetrating missiles, such as bullets or other objects. Injuries from stab wounds or foreign bodies (eg, glass, sheet metal) resulting in clean lacerations of nerves are known as are nerve injuries stemming from bone fractures and fracture-dislocations including ulnar nerve neurapraxia and radial nerve lesions and palsies. In general, acute nerve injury often produces a long-lasting neuropathic pain, manifested as allodynia, a decrease in pain threshold and hyperplasia, and an increase in response to noxious stimuli. See Colohan A R, et al. (1996) *Injury to the peripheral nerves*. In: Feliciano D V, Moore E E, Mattox K L. *Trauma*. $3^{rd}$ ed. Stamford, Conn.: Appleton & Lange; 1996: 853.

Further acute nerve injuries within the scope of the present invention include traumatic brain injury (TBI) and acute injuries to the spinal cord and peripheral/sensory nerves, various sports injuries involving nerve insult. See also WO2007/044928 and references cited therein.

In embodiments in which it is desired to promote axonal regeneration in response to an acute nerve injury, it will be generally preferably to administer at least one invention compound (e.g., one, two, or three of same) as soon as possible after the insult such as within about 24, 12, 6, 3, 2, 1, or less hours, preferably within 5, 10, 20, 30 or 40 minutes after the insult. Additionally, at least one of the invention compounds can be administered propholactically (as a precautionary measure) before a medical intervention (eg., surgery) associated with some risk of nerve damage. In this invention embodiment, nerve regeneration will be favorably enhanced and recovery times shortened.

As mentioned, the invention is useful for treating, preventing, or reducing symptoms associated with chronic injury to the nervous system. Non-limiting examples include those already described in WO2007/044928 including many chronic demyelinating neuropathies (CMT1 type), HMSN (CMT) disease type 1A and 1B, HNPP and other pressure palsies, Bethlem's myopathy, Limb-Geridle muscular dystrophy, Miyoshi myhopathy, rhizomelic chondrodysplasia punctata, HMSN-Lom, PXE (pseudoxanthomatosis elastica), CCFDN (congenital cataract facial dysmorphism and neuoropathy), Alzheimer's disease, Huntington's disease, Charcot-Marie-Tooth disease, multiple sclerosis, amyotrophic lateral sclerosis (ALS), Guillain-Barré syndrome (GBS, also known as acute inflammatory demyelinating polyneuropathy or AIDP), leukodystrophy, Parkinson's disease, motor neuron disease, diabetic neuropathies, distal axonopathies such as those resulting from a metabolic or toxic neuronal derangement (e.g., relating to diabetes, renal failure, exposure to a drug or toxin (e.g., an anti-cancer drug), malnutrition or alcoholism), mononeuropathies, radiculopathies (e.g., of cranial nerve VII; Facial nerve), Hansen's disease (leprosy), and plexopathies such as brachial neuritis; and focal entrapment neuropathies (e.g., carpal tunnel syndrome).

In embodiments in which the therapeutic goal is to treat a chronic nerve insult, more long term administration protocols will be generally preferred. Thus in one embodiment, at least one invention compound (e.g., one, two, or three of same) will be administered by any acceptable route mentioned herein for at least 24 hours, preferably for a few days, weeks or months up to a few years as needed to treat or reduce symptoms associated with the particular indication.

As mentioned, compounds of the invention can be used alone or in combination with other agents to treat, prevent or reduce symptoms of a disorder mediated by undesired activity of the complement system. In one embodiment in which inflammation accompanies or is suspected of accompanying the disorder, the method will include the step of administering at least one anti-inflammatory agent (e.g., 1, 2 or 3 of same) and/or a complement inhibitor. A non-limiting example of an anti-inflammatory agent is a steroid (e.g., a corticosteroid) or a non-steroidal anti-inflammatory drug (NSAID). Examples of other suitable steroids include cortisone, hydrocortisone, triamcinolone (kenacort), methylprednisolone (medrol), prednisolone (prelone), prednisone and dexamethasone (decadron). Illustrative NSAIDs include acetylsalicylic acid (aspirin, ecotrin), choline magnesium salicylate (trilisate), Cox-2 inhibitors, diclofenac (voltaren, cataflam, coltaren-XR), diflunisal (dolobid), etodolac, (iodine), fenoprofen (nalfon), flurbiprofen (ansaid), ibuprofen, indomethacin, (indocin, indocin-SR), ketoprofen, meclofenamate, (meclomen), nabumetone, (relafen), naproxen, (naprosyn, naprelan, anaprox, aleve), oxaprozin, (daypro), phenylbutazone, (butazolidine), piroxicam, (feldene), salsalate, (disalcid, salflex), tolmetin, (tolectin) and valdecoxib, (bextra).

In embodiments in which a composition of the invention is used to prevent, treat or reduce symptoms associated with multiple sclerosis, the composition may be used alone or in combination with one or more approved drugs such as Rebif® (interferon beta-1a, Serono, Pfizer), Avonex® (interferon beta-1a, Biogen-Idec), Betaseron® (interferon beta-1b, Bayer Schering), Copaxone® (glatiramer acetate, Teva), Novantrone® (mitozantrone, Serono), and Tysabri® (natalizumab, Biogen-Idec). As discussed in more detail below, co-administration of an invention compound will allow a patient to be exposed to less of an approved drug over a particular time period, thereby decreasing chances for undesirable side effects.

Drug Holiday

As discussed, it is possible to prevent, treat or reduce the severity of disorders mentioned herein by administering at least one invention compound. However, it has been found that it is not necessary to expose subjects to the compound continuously to achieve a desired effect. That is, it is possible to reduce administration of the compound, sometimes substantially, over a time period referred to herein as a "drug holiday." During the drug holiday, complement mRNA remains low (less than about 10%, 20%, 30%, 40%, 50%, or more compared to control and using qPCR) over a several days, over a few weeks, up to about a month after administration of the invention compound. It is believed that the amount of complement mRNA produced under these conditions is insufficient to produce normal levels of the encoded protein. Administration of an invention compound, either alone or in combination with another drug is not needed over this time period. After the drug holiday, administration of one or more invention compounds alone or in combination with other drug(s) can be resumed.

Practice of this aspect of the invention provides important advantages.

For example, use of the invention can provide human patients with much sought after relief from invasive, sometimes painful, and often repetitive and expensive treatment protocols. Potentially serious side effects can be reduced, delayed, or in some instances eliminated. By way of example, risk of developing nausea, flu-like symptoms, injection site reactions, alopecia, infections, pneumonia, menstruation problems, depression, cholelithiasis, and/or progressive multifocal leukoencephalopathy (PNL) has been reported in some patients receiving drugs to treat multiple sclerosis. These and other side effects can be reduced or avoided in some cases by practice of the invention.

Additionally, costs associated with repeated and frequent dosing of drugs can be reduced by use of the invention. As an example, each of Rebif®, Avonex®, Betaseron®, and Copaxone® is said to be administered to multiple sclerosis patients once or more every week, usually by a painful injection. It is believed that co-administration of an invention compound will result in less drug being required per administration. Alternatively, or in addition, less frequent dosing of drug will be needed. In either case, patient treatment costs are lowered and patient comfort is enhanced. Other drugs used to treat multiple sclerosis are said to be administered to patients every few months (eg., Novantrone®, and Tysabri®). Even in these embodiments, practice of the invention can reduce the amount of drug required, or result in less frequent dosing, thereby providing less risk of side effects and lower costs.

It is a further object of the invention to provide a method to prevent, treat, or reduce symptoms of a disorder referred to herein in which administration of an invention compound alone or in combination with a known drug is reduced during the drug holiday period. In one embodiment, administration of the drug is eliminated entirely during the drug holiday period. After or sometimes during the drug holiday period, the invention compound, known drug (or both) are administered again to the mammal in an amount that is the substantially the same or different (e.g., lower) from the amount administered previously. That second drug administration can be followed by another drug holiday if desired. Thus it is a feature of the invention to provide for at least one drug holiday in which each drug holiday is preferably followed by administration of an amount of at least one of an invention compound, known drug (or both) to achieve a desired therapeutic outcome.

Thus in a particular embodiment, an invention compound is administered to a human patient suffering from (or suspected of suffering from) multiple sclerosis. The invention compound can be administered alone or in combination with a known multiple sclerosis drug such as Rebif®, Avonex®, Betaseron®, Copaxone®, Novantrone® or Tysabri® in an amount that is therapeutically effective. During the drug holiday period, further administration of the invention compound and/or the multiple sclerosis drug can be substantially reduced or even avoided. The method can be repeated once, twice, thrice, or as often as needed to provide a therapeutic regimen that features one, two, three, or more drug holidays. The invention methods can be repeated as needed, e.g., every few days, every few weeks, every few months up to the lifetime of the patient to prevent, treat or reduce symptoms associated with multiple sclerosis.

Prior to induction of a drug holiday, the amount of the invention compound or known drug is preferably, but not exclusively, one that is therapeutically effective. In one embodiment, the amount of the invention compound is generally sufficient to reduce presence of complement mRNA compared to a control and as determined, for example, by pPCR. To begin the drug holiday, the amount of the invention compound or known drug is reduced or eliminated entirely. The drug holiday period is not tied to any particular level of complement mRNA in vivo so long as levels remain below a control as mentioned previously. Following the drug holiday period, the mammal can be subjected to additional therapy including further administration of at least one invention compound either alone or in combination with the known drug such as those used to treat multiple sclerosis as mentioned herein.

Use of a particular drug holiday protocol will be guided by recognized parameters such as the patient's general health, sex, severity of the disorder, type of known drug being administered, etc.

The invention further provides a method of enhancing nerve regeneration in a mammal comprising administering to the mammal (therapeutically or prophylactically) an amount of at least one of the compounds of the invention sufficient to reduce or inhibit expression of C6 in the mammal and enhance nerve regeneration therein. Methods for evaluating nerve regeneration enhancement have been described herein including various tests to detect and optionally quantify motor and sensory nerve function.

If desired, one of more of the invention compounds disclosed herein can be combined with one or more of the compounds disclosed the following co-pending patent applications by the named inventors which applications are entitled *Antagonists of Complement Component (C8-alpha) and Uses Thereof, Antagonists of Complement Component (C8-beta) and Uses Thereof; and Antagonists of Complement Component (C9) and Uses Thereof*; each of which applications have the same filing date as the present application. In this embodiment, combining compounds that target different MAC complex components can reduce expression of the complex.

Reference herein to an <<invention compound>> or like phrase or <<composition of the invention>> or like phrase means a composition disclosed herein.

Other more specific embodiments are within the scope of the present invention. For instance, the invention provides an oligomer of between about 10 to 50 nucleotides in length having a contiguous nucleobase sequence with at least 95%, 96%, 97%, 98%, 99% or 100% sequence identity to a corresponding region of a nucleic acid which encodes the COMPLEMENT COMPONENT 6 (C6) sequence represented by SEQ ID NO: 1 or a naturally occurring allelic variant thereof in which the oligomer includes at least one nucleotide analogue. Preferably, the oligomer is capable of reducing the level of C6 mRNA expression in a mammal by at least 20% as determined by a qPCR assay. In one embodiment, the oligomer further includes at least one of a modified internucleoside linkage and a modified nucleobase. Examples are provided herein and include a modified sugar moiety selected from the group consisting of: 2'-β-methoxyethyl modified sugar moiety, a 2'-methoxy modified sugar moiety, a 2'-β-alkyl modified sugar moiety, and a bicyclic sugar moiety. A typically preferred bicyclic sugar moiety for use with this embodiment is an LNA monomer. In a more particular embodiment, the oligomer is a gapmer comprising 2 or 3 LNA monomers at each of the 3' and 5' ends of the oligomer. In one example, the oligomer further includes one or more 2'-deoxynucleotides positioned between the 5' and 3' wing segments. Optionally, the gapmer may include an additional 2'-deoxynucleotide positioned at the 3' end, the 5' end or both the 3'- and 5' ends of the oligomer. A typically useful modified internucleotide linkage for use with the foregoing invention example is a phosphorothioate internucleoside linkage. The modified nucleobase can be a 5-methylcytosine. Smaller oligomers will often be useful such as between about 12 to about 20 nucleotides, more specifically between about 15 to about 18 nucleotides in length, such as 15, 16, 17, 18, or 19 nucleotides in length, Typically useful oligomers for many invention embodiments are those that are targeted to about nucleotides 1-332, 253-653, 266-766, 526-926, 853-1253 from the ATG start site of SEQ ID NO: 1 (starting at the "A"); particularly about nucleotides 32-232, 353-553, 466-666, 626-826 and 953-1153; more particularly about nucleotides 82-182, 403-503, 516-616, 676-776, 1003-1103; even more particularly 112-152, 433-473, 546-586, 706-746, 1015-1055; for instance, the specific target sites referred to in Tables 1 and 2, below. As will be appreciated, such oligomers may possess less than 100% sequence identify with the sequence represented by SEQ ID NO: 1 provided intended results are achieved. Thus in one embodiment, the oligomer comprises one, two, three, four or five mismatches with respect to the Complement Component C6 sequence represented by SEQ ID NO:1. A generally useful oligomer is an antisense oligonucleotide.

Also provided is a pharmaceutical composition that includes at least one oligomer as disclosed herein and a pharmaceutically acceptable diluent, carrier, salt or adjuvant. For many invention embodiments, an oligomer provided as an orally acceptable formulation will be useful.

Additionally provided is a method of reducing or inhibiting the expression of COMPLEMENT COMPONENT 6 (C6) in a cell or a tissue in vivo, the method comprising the step of contacting said cell or tissue with the oligomer of claim 1 so that expression of the COMPLEMENT COMPONENT 6 (C6) is reduced or inhibited. The method may include the further step of measuring at least one of the Complement Component 6 (C6) (e.g., by immunodetection methods), mRNA encoding the protein (e.g., by pPCR) and a membrane attack complex (MAC, e.g., by CH50 assay) following administration of the oligomer.

Also within the scope of the present invention is a method of reducing or inhibiting the production of a membrane attack complex (MAC) in a cell or a tissue in vivo, the method comprising the step of contacting said cell or tissue with the oligomer of claim 1 so that expression of the MAC is reduced or inhibited. The method may include the further step of measuring at least one of the Complement Component 6 (C6) (e.g., by immunodetection methods), mRNA encoding the protein (e.g., by pPCR) and a membrane attack complex (MAC, e.g., by CH50 assay) following administration of the oligomer.

The invention also provides a method for treating, preventing or reducing symptoms of a disorder mediated by undesired activity of the complement system. Preferably, the method includes administering at least one of the pharmaceutical compositions disclosed herein a mammal in need thereof. In one embodiment, the disorder is a chronic demyelinating neuropathy such as multiple sclerosis (e.g., RRMS type). The method is flexible and can be used so that the pharmaceutical composition includes one or more invention compounds. Alternatively, the pharmaceutical composition can further include a known drug such as at least one of Rebif® (interferon beta-1a), Avonex® (interferon beta-1a), Betaseron® (interferon beta-1b), Copaxone® (glatiramer acetate), Novantrone® (mitozantrone), and Tysabri® (natalizumab) (all for treatment of multiple sclerosis).

Also provided is a method for treating, preventing or reducing symptoms of a disorder mediated by undesired activity of the complement system. Preferably, the method includes administering at least one of the pharmaceutical compositions disclosed herein to a mammal in need thereof and further including the administration of one or more of an anti-inflammatory agent and a complement inhibitor.

A particular disorder for which the invention methods are useful is neuronal trauma which may be acute or chronic. An example of acute neuronal trauma is traumatic brain injury (TBI).

Further provided is use of at least one of the compositions of the invention (e.g., 1, 2 or 3) for the manufacture of a medicament for the treatment of a condition requiring axonal regeneration.

Further provided is use of at least one of the compositions of the invention (e.g., 1, 2 or 3) for the manufacture of a medicament for the treatment of a chronic dyemylinating condition such as multiple sclerosis.

The following examples are given for purposes of illustration only in order that the present invention may be more fully understood. These examples are not intended to limit in any way the scope of the invention unless otherwise specifically indicated.

The disclosures of all references mentioned herein are incorporated herein by reference.

Example 1

Antisense Inhibitors of Complement Synthesis in the Liver

Complement component C6 is mainly expressed in the liver and secreted from this organ into the circulation. Knockdown of the liver expression of C6 will substantially reduce ability to form MAC complexes thus reducing the efficacy of the complement system. Many studies have confirmed that systemically administrated antisense oligonucleotides are efficacious in the liver.

Antisense Oligonucleotides

The antisense oligomers against complement component C6 were designed against sequences with the high homology between rodents and human (See Tables 5A-5F. 3A-3F). The antisense oligonucleotides (15-18mers) were chemically modified with Locked Nucleic Acids (LNA). The LNA protects the oligo against nuclease and increases the affinity ($T_m$) for complementary mRNA sequences allowing the use of short 15-18 mer oligonucleotides with high efficacy. Oligomers shorter than 18 nucleotides are less prone to activate innate immune responses as compared to longer oligomers. The oligonucleotide were designed as a gapmer. This means that the three ultimate positions at the 5' end and the penultimate 3 positions at the 3' end of the oligo contain LNA moieties while the center and the 3' ultimate position consists out of DNA analogues. An example of a typical gapmer design is indicated below:

| L = LNA, d = DNA |
|---|
| 5'-LLLddddddddddLLLd-3' |
| or |
| 5'-LLLddddddddddLLL-3' | in which L=LNA and d=DNA. The whole oligo is phosphorothiolated to reduce renal clearance and increase circulation time in vivo. All C residues were converted to methyl-C to reduce immune stimulation.

Table 1, below, shows the structure of LNA modified antisense oligonucleotides made against mouse C6 (target sequence and oligo sequence is mouse). (Bold and large case text=LNA, small case text=DNA):

TABLE 1

| Oligomer | SEQ ID NO: | LNA modified Oligomer | SEQ ID NO: |
|---|---|---|---|
| Target Position 132 GAGCAGACAGAGACAA | 404 | Oligo5'3' T T G t c t c t g t c t g C T C Batch No. 1008 | 405 |
| Target Position 453 TATTCCCAGCAAGTTA | 406 | Oligo5'3' T A A c t t g c t g g g a A T A Batch No. 1009 | 407 |
| Target Position 566 GTGTGCAGCTGATGGG | 408 | Oligo5'3' C C C a t c a g c t g c a C A C Batch No. 1010 | 409 |
| Target Position 726 GGTACAAACTATAGAA | 410 | Oligo5'3' T T C t a t a g t t t g t A C C Batch No. 1011 | 411 |
| Target Position 1035 GCCTTTAGAATACAAC | 412 | Oligo5'3' G T T g t a t t c t a a a G G C Batch No. 1012 | 413 |

All of the LNA modified oligomers shown in Table 1 were fully phosphorothiolated.

All oligomers (ODN's) were synthesized using the phosphoramidite approach on an ÄKTA Oligopilot (GE Healthcare) at 130-185 μmole scales using a polystyrene primer support. The ODN's were purified by ion exchange (IEX) and desalted using a Millipore-membrane. ODN's were characterized by LC/MS (Agilent). The molecular mass of the ODNs were checked by Matrix-assisted laser desorption ionization time-of-flight mass spectrometry (MALDI-TOF) on a Biflex III MALDI (Brucker instruments, Leipzig, Germany).

the mice were sacrificed at day four. Liver samples were taken out and are used to determine the knockdown levels of the protein components using Western blotting for detection of the protein levels and quantative qPCR for mRNA levels.

Western-immuno blots can be done after denaturing acryl amide electrophoresis under standard conditions using the mini-protean system (Biorad). Complement proteins are detected using commercially available specific monoclonal and polyclonal antibodies Immunodection of proteins is done using the Lumi-Light enhanced chemi-luminescence kit (Roche) and the LAS-3000 darkbox imaging system (FujiF-

TABLE 2

| Oligo target batch | Seq ID | oligo start relative ATG | | seq ID |
|---|---|---|---|---|
| GAGCAGACAGAGACAA mouse | 404 | 132 | T T G t c t c t g t c t g C T C 405 | 1008 |
| GAGCAGACACAGACAAATA human | 414 | | T T G t c t g t g t c t g C T C 415 | |
| TATTCCCAGCAAGTTA | 408 | 453 | T A A c t t g c t g g g a A T A 409 | 1009 |
| CTGCATTGCCAGAAAGTTA | 416 | | T A A c t t t c t g g c a A T G 417 | |
| GTGTGCAGCTGATGGG | 412 | 566 | C C C a t c a g c t g c a C A C 413 | 1010 |
| GTGTACAGTTGATGGGCAA | 418 | | C C C a t c a a c t g t a C A C 419 | |
| GGTACAAACTATAGAA | 416 | 726 | T T C t a t a g t t t g t A C C 417 | 1011 |
| GGTACAAACTGCAGAAGAT | 420 | | T T C t g c a g t t t g t A C C 421 | |
| GCCTTTAGAATACAAC | 420 | 1035 | G T T g t a t t c t a a a G G C 421 | 1012 |
| CATCTGCCTCTAGAATACAACTCTG | 422 | | G T T g t a t t c t a g a G G C 423 | |

Table 2 shows the mouse oligomers shown in Table 1 along with preferred corresponding human oligomers without (SEQ ID Nos: 414, 416, 418, 420, and 422) or with LNA monomers (SEQ ID Nos. 415, 417, 419, 421, and 423). For oligomers with LNA substitutions, LNA monomers are shown in bold uppercase text while DNA is shown in unbold, lower case text.

In Vivo Oligo Efficacy Test

Since cell lines in culture do not express (or only at a very low level) complement proteins, the efficacy of the oligonucleotides can be tested directly in vivo. The goal of the first screen was to identify from the list of initial designs a set of potential oligo's with efficacy in vivo. Eight to ten week old mice NMRI strain (Charles River, the Netherlands) are injected (intraperitonally IP or intravenously (IV)) once a day with 5 mg/kg of oligo dissolved in PBS. As control we gave PBS injections only in the first screening. For each treatment five mice per group was used. After three days of treatment ilm, Tokyo, Japan). qPCR was done using universal probes (Roche) on the Lightcycler 480 system (Roche)

After selection of potential lead candidates, specific mismatch versions (minimal 3 mismatches) as control can be designed.

Prolonged administration of oligonucleotides (>4 days) was done using osmotic mini pumps (Alzet, Durect Co., Cupertino, Calif., USA). These pumps are implanted dorsally according to the instructions of the manufacturer. The osmotic minipumps are incubated in PBS 20 hours at 37° C. prior to implantation to start up the pump, in order to quickly reach a steady delivery rate after implantation. The usage of these pumps reduces the stress in the animals in prolonged experiments since it is not required to perform daily injections. In vitro testing shows that the Alzet minipumps reach a steady pumping rate within 24 hours. The osmotic minipumps were filled with oligonucleotides dissolved in PBS.

Mini Tox Screen

Blood samples are taken to measure aspartate aminotransferase (ASAT) and alanine aminotransferase (ALAT) levels in the serum. ASAT and ALAT levels in serum are determined using standard diagnostic procedures with the H747 (Hitachi/Roche) with the appropriate kits (Roche Diagnostics). Bodyweight is monitored and body temperature of mice is measured daily for each mouse using IPTT-200 transponder chips and a DAS 5002 chip reader (Biomedic Data Systems, Seaford, Del., USA).

Example 2

In Vivo Complement mRNA Levels after 3 Days of Treatment with Oligonucleotides The LNA oligonucleotides shown in Table 1, above, were used to reduce levels of C6 mRNA in NMRI nu/nu mice. Four animals per treatment group were used including one PBS control mouse (15 mice total). Mice received IP injections of each oligo at day 1, 2 and 3 (5 mg/kg animal). Mice were sacrificed at day 4 and livers excised. RNA was prepared using conventional approaches. C6 mRNA was quantified using qPCR with the Roche lightcycler 480 and universal probes according to the manufacturer's instructions.

FIG. 1 shows in vivo complement mRNA levels after 3 days of treatment with the complement antisense LNA oligonucleotides. Oligo 1008 (SEQ ID NO: 405) was toxic as two animals died on day 3 and one animal appeared sick at day 4.

Example 3

CH50 Assay Balb/C Mice

Antisense oligomers against the complement components were designed against sequences with the high homology between rodents and human. The antisense oligonucleotides were chemically modified with Locked Nucleic Acids (LNA). The LNA protects the oligo against nuclease and increases the affinity (Tm) for complementary mRNA sequences. The oligonucleotides were designed as gapmers. This means that the three ultimate positions at the 5' end and the penultimate 3 positions at the 3' end of the oligo contain LNA moieties while the center and the 3' ultimate position consists out of DNA analogues.

All antisense oligonucleotides (ODNs) were synthesized as all-phosphorothioate derivatives on an automated DNA synthesizer using commercial DNA and LNA phosphoramidites (Exiqon A/S, Denmark). In all ODNs 5-methyl-C was used. The DMT-ON ODNs were purified by reversed phase HPLC(RP-HPLC) (>95% purity). After the removal of the DMT-group, the ODNs were characterized by AE-HPLC, and the expected molecular mass was confirmed by ESI-MS and Matrix-assisted laser desorption ionization time-of-flight mass spectrometry (MALDI-TOF) on a Biflex III MALDI (Brucker instruments, Leipzig, Germany).

Mice. All experiments involving animals were sanctioned by the local ethical committee and are in full compliance with the law in the Netherlands. 7-8 week old female Balb/C mice (Harlan) were given oligonucleotides using ALZET 1002 osmotic minipumps (Durect Corporation, Cupertino, Calif., USA) implanted subcutaneously. ODNs and siRNA were dissolved in PBS. Dosages as indicated in the figures.

CH50 hemolytic assay. The hemolytic CH50 assay was used to determine the effect of complement knockdown in the liver on membrane attack complex (MAC) activity in the circulation. This assay measures the hemolytic activity of MAC in serum. Sensitized erythrocytes are added to the sera of mice and the activity of MAC can be measured as the amount of erythrocyte lysis using a spectrophotometer. Blood was drawn from the mice and this was coagulated on ice for 1 hr. Then the serum was isolated aliquoted in 20 ul samples and immediately frozen in liquid nitrogen. The CH50 assay was done using rabbit erythrocytes sensitized using a mouse anti Rabbit erythrocyte polyclonal antiserum (Paul Morgan, Cardiff University). The rabbit erythrocytes were at least 1 months old (but not older than 3 months) before use because this increases the sensitivity of the assay. The sensitized rabbit erythrocytes (50 ul) are incubated in Veronal buffered saline (40 ul) in the presence of 10 ul of mouse serum at 37° C. To obtain 100% lysis value 100 ul water is added. After 30-60 minutes the remaining erythrocytes are spun down and the OD405 nm is measured using a spectrophotometer.

Figure 2:
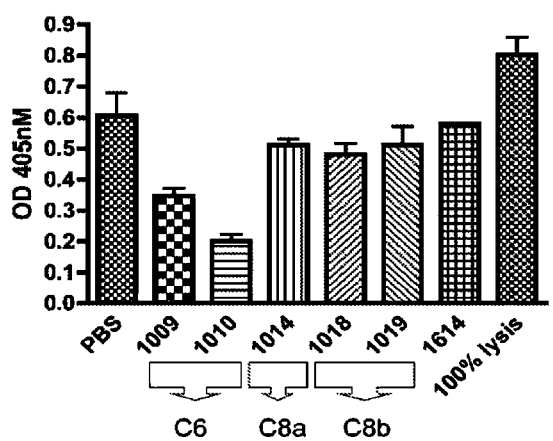
FIG. 2 is a graph showing efficacy of membrane attack complex (MAC) activity in mouse serum after treatment with LNA-modified oligonucleotides targeting complement proteins C6, C8a, or C8b. Oligonucleotides were administered for one week.

FIG. 2 shows that oligo 1009 (SEQ ID NO. 409). Oligo 1010 (SEQ ID NO. 413), Oligo 1014 (C8a application, SEQ ID NO. 327), Oligo 1018 (C8b application, SEQ ID NO. 336), Oligo 1019 (C8b application, SEQ ID NO. 338) showed ability to inhibit MAC formation relative to two controls. All oligonucleotides mediated a knockdown of their intended target in the liver for at least 70% as measured with qPCR. Dosage 5 mg/kg/day for two weeks. Oligo 1614 is a scrambled oligonucleotide control with no activity on complement levels. MAC activity was measured using a CH50 hemolytic assay described above. Data depicted as mean of 5 mice per group±SEM

Example 4 siRNA Construct Reduces C6 mRNA

Procedures outlined above were used to make Oligo 1010 (SEQ ID NO. 413). From 0.5 mg/kg to 5 mg/kg were injected into mice as described above. qPCR was used to measure C6 expression as follows: Animals were sacrificed and liver samples were taken using RNA later (Ambion) as storage solution. Livers were homogenized in trizol using the Magnalyzer and magnalyzer beads (Roche) RNA was isolated using Trizol according to the instructions of the manufacturer (Invitrogen). cDNA was made using oligodT primer and SuperScriptII enzyme (Invitrogen). qPCR was done using Universal probe primers (Roche) and a Lightcycler 480 (Roche). All data was corrected using Hprt1 (hypoxanthine guanine phosphoribosyl transferase 1) as housekeeping gene/ loading control. All reactions were done in triplicate and qPCR conditions were as standard recommended by the manufacturer (Roche). In addition, an LNA modified siRNA homologous was made to the sequence targeted by antisense oligo Oligo 1010 (SEQ ID NO. 413).

An LNA modified siRNA homologous to the sequence targeted by antisense oligo Oligo 1010 (SEQ ID NO. 413) was also designed. This siRNA has LNA modifications on the 3' overhangs of both strands and one LNA at the 5' end of the sense (passenger) strand.

The LNA modified siRNA was synthesized on an automated DNA/RNA synthesizer RNA synthesis cycle (1-5 µmol scale), O2'-TBDMS protected RNA phosphoramidites and common reagents were used and the stepwise coupling yield of all monomers was >99%. For incorporation of modified nucleotides, a coupling time of 10 min was used. Following standard de-protection, purification and work-up, the composition and purity (>80%) of the resulting siRNA was confirmed by MALDI-MS analysis and ion exchange HPLC.

Figure 3:
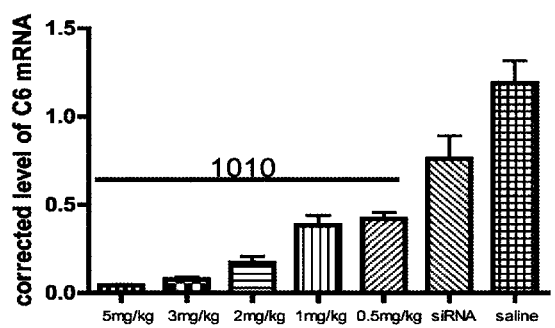
FIG. 3 is a graph showing administration of varying amounts of oligo 1010 (SEQ ID NO. 413) to a mouse versus a corrected level of C6 mRNA. Also shown is results for the corresponding siRNA construct.

FIG. 3 shows that there was a linear correlation between the amount of Oligo 1010 administered to Balb/C mice and the corrected level of C6 mRNA. The figure also shows that the siRNA construct reduced C6 mRNA relative to the control. In particular, Oligo 1010 had a dose effect on C6 mRNA expression as measured with qPCR in the liver of Balb/C mice in vivo as compared to the effect of treatment with the homologous LNA modified siRNA sequence. Data depicted as mean of 5 mice per group±SEM.

Example 5

Nerve Crush Assay

The nerve crush assay measures the effect of complement inhibition on the recovery of peripheral nerves after a crush injury. The assay is generally disclosed by Ramaglia, V. et al. (2007) Jul. 18: 27(29) 7663 and references disclosed therein. Briefly, animals were treated for 14 days with antisense oligonucleotides or PBS as control after which they receive a nerve crush injury. All surgical procedures were performed aseptically under deep isoflurane anesthesia (1.5 v/l isoflurane and 1.0 v/l $O_2$). The left sciatic nerve was exposed via an incision in the upper thigh. The nerve was crushed for 3×10 s periods at the level of the sciatic notch using smooth forceps. The right leg served as control; sham surgery was performed which exposed the sciatic nerve but did not disturb it. The muscle and the skin were then closed with stitches. Mice were under analgesia during the post-operative recovery periods. They were treated with one dose (0.05 mg/kg) of Buprenorphine (Temgesic®, Schering-Plough, The Netherlands) right before the injury and a second dose of analgesic at 1 day post-injury. The sensory function was measured using a footflick test. In this test a variable electric current (0.1-0.5 mA) is given to the foot sole using two stimulation electrodes. A response was scored positive if the animal retracted its paw. The minimal current (mA) needed to elicit a retraction response was recorded. Values are expressed as percentage of normal function (right control leg). Using this assay, at least one oligomer of the invention showed significant activity in the footflick test. In particular, mice receiving the oligomer in suitable carrier showed 50% recovery in the footflick assay at about day 7. Untreated animals showed the same recovery around day 11.

The disclosures of all references mentioned herein (including all patent and scientific documents) are incorporated herein by reference. The invention has been described in detail with reference to preferred embodiments thereof. However, it will be appreciated that those skilled in the art, upon consideration of this disclosure, may make modifications and improvements within the spirit and scope of the invention.

TABLE 3

Nucleic acid sequence encoding human complement component 6 (C6) mRNA (SEQ ID NO: 1). The ATG start site is indicated. (Genbank Ref. NM_000065.2)

SEQ ID No: 1
AACATTTATTTTGACAACCCTCTAGGTGTTGCTAGGCTTCTGGGATATGACAGCATTGCCTTGTGTTAGC

TAGCAATAAGAAAAGAAGCTTTGTTTGGATTAACATATATACCCTCTTCATTCTGCATACCTATTTTTTC

CCCAATAATTTGCAGCTTAGGTCCGAGGACACCACAAACTCTGCTTAAAGGGCCTGGAGGCTCTCAAGGC

ATGGCCAGACGCTCTGTCTTGTACTTCATCCTGCTGAATGCTCTGATCAACAAGGGCCAAGCCTGCTTCT

GTGATCACTATGCATGGACTCAGTGGACCAGCTGCTCAAAAACTTGCAATTCTGGAACCCAGAGCAGACA

CAGACAAATAGTAGTAGATAAGTACTACCAGGAAAACTTTTGTGAACAGATTTGCAGCAAGCAGGAGACT

AGAGAATGTAACTGGCAAAGATGCCCCATCAACTGCCTCCTGGGAGATTTTGGACCATGGTCAGACTGTG

ACCCTTGTATTGAAAAACAGTCTAAAGTTAGATCTGTCTTGCGTCCCAGTCAGTTTGGGGGACAGCCATG

CACTGCGCCTCTGGTAGCCTTTCAACCATGCATTCCATCTAAGCTCTGCAAAATTGAAGAGGCTGACTGC

AAGAATAAATTTCGCTGTGACAGTGGCCGCTGCATTGCCAGAAAGTTAGAATGCAATGGAGAAATGACT

GTGGAGACAATTCAGATGAAAGGGACTGTGGGAGGACAAAGGCAGTATGCACACGGAAGTATAATCCCAT

CCCTAGTGTACAGTTGATGGGCAATGGGTTTCATTTTCTGGCAGGAGAGCCCAGAGGAGAAGTCCTTGAT

AACTCTTTCACTGGAGGAATATGTAAAACTGTCAAAAGCAGTAGGACAAGTAATCCATACCGTGTTCCGG

CCAATCTGGAAAATGTCGGCTTTGAGGTACAAACTGCAGAAGATGACTTGAAAACAGATTTCTACAAGGA

TTTAACTTCTCTTGGACACAATGAAAATCAACAAGGCTCATTCTCAAGTCAGGGGGGGAGCTCTTTCAGT

GTACCAATTTTTTATTCCTCAAAGAGAAGTGAAAATATCAACCATAATTCTGCCTTCAAACAAGCCATTC

AAGCCTCTCACAAAAAGGATTCTAGTTTTATTAGGATCCATAAAGTGATGAAAGTCTTAAACTTCACAAC

GAAAGCTAAAGATCTGCACCTTTCTGATGTCTTTTTGAAAGCACTTAACCATCTGCCTCTAGAATACAAC

TCTGCTTTGTACAGCCGAATATTCGATGACTTTGGGACTCATTACTTCACCTCTGGCTCCCTGGGAGGCG

TGTATGACCTTCTCTATCAGTTTAGCAGTGAGGAACTAAAGAACTCAGGTTTAACCGAGGAAGAAGCCAA

ACACTGTGTCAGGATTGAAACAAAGAAACGCGTTTTATTTGCTAAGAAAACAAAAGTGGAACATAGGTGC

ACCACCAACAAGCTGTCAGAGAAACATGAAGGTTCATTTATACAGGGAGCAGAGAAATCCATATCCCTGA

TABLE 3-continued

Nucleic acid sequence encoding human complement component 6 (C6) mRNA (SEQ ID NO: 1). The ATG start site is indicated. (Genbank Ref. NM_000065.2)

```
TTCGAGGTGGAAGGAGTGAATATGGAGCAGCTTTGGCATGGGAGAAAGGGAGCTCTGGTCTGGAGGAGAA
GACATTTTCTGAGTGGTTAGAATCAGTGAAGGAAAATCCTGCTGTGATTGACTTTGAGCTTGCCCCCATC
GTGGACTTGGTAAGAAACATCCCCTGTGCAGTGACAAAACGGAACAACCTCAGGAAAGCTTTGCAAGAGT
ATGCAGCCAAGTTCGATCCTTGCCAGTGTGCTCCATGCCCTAATAATGGCCGACCCACCCTCTCAGGGAC
TGAATGTCTGTGTGTGTGTCAGAGTGGCACCTATGGTGAGAACTGTGAGAAACAGTCTCCAGATTATAAA
TCCAATGCAGTAGACGGACAGTGGGGTTGTTGGTCTTCCTGGAGTACCTGTGATGCTACTTATAAGAGAT
CGAGAACCCGAGAATGCAATAATCCTGCCCCCCAACGAGGAGGGAAACGCTGTGAGGGGGAGAAGCGACA
AGAGGAAGACTGCACATTTTCAATCATGGAAAACAATGGACAACCATGTATCAATGATGATGAAGAAATG
AAAGAGGTCGATCTTCCTGAGATAGAAGCAGATTCCGGGTGTCCTCAGCCAGTTCCTCCAGAAAATGGAT
TTATCCGGAATGAAAAGCAACTATACTTGGTTGGAGAAGATGTTGAAATTTCATGCCTTACTGGCTTTGA
AACTGTTGGATACCAGTACTTCAGATGCTTACCAGACGGGACCTGGAGACAAGGGGATGTGGAATGCCAA
CGGACGGAGTGCATCAAGCCAGTTGTGCAGGAAGTCCTGACAATTACACCATTTCAGAGATTGTATAGAA
TTGGTGAATCCATTGAGCTAACTTGCCCCAAAGGCTTTGTTGTTGCTGGGCCATCAAGGTACACATGCCA
GGGGAATTCCTGGACACCACCCATTTCAAACTCTCTCACCTGTGAAAAAGATACTCTAACAAAATTAAAA
GGCCATTGTCAGCTGGGACAGAAACAATCAGGATCTGAATGCATTTGTATGTCTCCAGAAGAAGACTGTA
GCCATCATTCAGAAGATCTCTGTGTGTTTGACACAGACTCCAACGATTACTTTACTTCACCCGCTTGTAA
GTTTTTGGCTGAGAAATGTTTAAATAATCAGCAACTCCATTTTCTACATATTGGTTCCTGCCAAGACGGC
CGCCAGTTAGAATGGGGTCTTGAAAGGACAAGACTTTCATCCAACAGCACAAAGAAAGAATCCTGTGGCT
ATGACACCTGCTATGACTGGGAAAAATGTTCAGCCTCCACTTCCAAATGTGTCTGCCTATTGCCCCCACA
GTGCTTCAAGGGTGGAAACCAACTCTACTGTGTCAAAATGGGATCATCAACAAGTGAGAAAACATTGAAC
ATCTGTGAAGTGGGAACTATAAGATGTGCAAACAGGAAGATGGAAATACTGCATCCTGGAAAGTGTTTGG
CCTAGCACAATTACTGCTAGGCCCAGCACAATGAACAGATTTACCATCCCGAAGAACCAACTCCTACAAA
TGAGAATTCTTGCACAAACAGCAGACTGGCATGCTCAAAGTTACTGACAAAAATTATTTTCTGTTAGTTT
GAGATCATTATTCTCCCCTGACTCTCCTGTTTGGGCATGTCTTATTCAGTTCCAGCTCATGACGCCCTGT
AGCATACCCCTAGGTACCAACTTCCACAGCAGTCTCGTAAATTCTCCTGTTCACATTGTACAAAAATAAT
GTGACTTCTGAGGCCCTTATGTAGCCTGTGACATTAAGCATTCTCGCAATTAGAAATAAGAATAAAACCC
ATAATTTTCTTCAATGAGTTAATAAACAGAAATCTCCAGAACCTCTGAAACACATTCTTGAAGCCCAGCT
TTCATATCTTCATTCAACAAATAATTTCTGAGTGTGTATACAGGATGTCAAGTACTGACCAAAGTCCTGA
GAACTCGGCAGATAATAAAACAGACAAAAGCCTTTGCCTTCATGAAGCATACATTCATTCAGGGGTAGAC
ACACAAAAAATGAAATAAACAGGTAAAATATGTAGC
```

TABLE 4A

Selected C6 oligonucleotides, SEQ ID Nos: 2-67

| DNA Sequence | SEQ ID NO: | RNA Sequence | SEQ ID NO: | Reverse Complement | SEQ ID NO: |
|---|---|---|---|---|---|
| | | 1030 CATCTGCCTCTAGAATACAACTCTG | SEQ ID NO: 2 | | |
| ATCTGCCTCTAGAATACAA | 3 | AUCUGCCUCUAGAAUACAA | 10 | UUGUAUUCUAGAGGCAGAU | 17 |
| CATCTGCCTCTAGAATACA | 4 | CAUCUGCCUCUAGAAUACA | 11 | UGUAUUCUAGAGGCAGAUG | 18 |

TABLE 4A-continued

Selected C6 oligonucleotides, SEQ ID Nos: 2-67

| DNA Sequence | SEQ ID NO: | RNA Sequence | SEQ ID NO: | Reverse Complement | SEQ ID NO: |
|---|---|---|---|---|---|
| CTGCCTCTAGAATACAACT | 5 | CUGCCUCUAGAAUACAACU | 12 | AGUUGUAUUCUAGAGGCAG | 19 |
| GCCTCTAGAATACAACTCT | 6 | GCCUCUAGAAUACAACUCU | 13 | AGAGUUGUAUUCUAGAGGC | 20 |
| TCTGCCTCTAGAATACAAC | 7 | UCUGCCUCUAGAAUACAAC | 14 | GUUGUAUUCUAGAGGCAGA | 21 |
| TGCCTCTAGAATACAACTC | 8 | UGCCUCUAGAAUACAACUC | 15 | GAGUUGUAUUCUAGAGGCA | 22 |
| CCTCTAGAATACAACTCTG | 9 | CCUCUAGAAUACAACUCUG | 16 | CAGAGUUGUAUUCUAGAGG | 23 |
| | 1112 | TGGGAGGCGTGTATGACCTTCTCTA SEQ ID NO: 24 | | | |
| GCGTGTATGACCTTCTCTA | 25 | GCGUGUAUGACCUUCUCUA | 32 | UAGAGAAGGUCAUACACGC | 39 |
| GAGGCGTGTATGACCTTCT | 26 | GAGGCGUGUAUGACCUUCU | 33 | AGAAGGUCAUACACGCCUC | 40 |
| AGGCGTGTATGACCTTCTC | 27 | AGGCGUGUAUGACCUUCUC | 34 | AGAAGGUCAUACACGCCU | 41 |
| GGCGTGTATGACCTTCTCT | 28 | GGCGUGUAUGACCUUCUCU | 35 | AGAGAAGGUCAUACACGCC | 42 |
| TGGGAGGCGTGTATGACCT | 29 | UGGGAGGCGUGUAUGACCU | 36 | AGGUCAUACACGCCUCCCA | 43 |
| GGGAGGCGTGTATGACCTT | 30 | GGGAGGCGUGUAUGACCUU | 37 | AAGGUCAUACACGCCUCCC | 44 |
| GGAGGCGTGTATGACCTTC | 31 | GGAGGCGUGUAUGACCUUC | 38 | GAAGGUCAUACACGCCUCC | 45 |
| | 1115 | GAGGCGTGTATGACCTTCTCTATCA SEQ ID NO: 46 | | | |
| TGTATGACCTTCTCTATCA | 47 | UGUAUGACCUUCUCUAUCA | 54 | UGAUAGAGAAGGUCAUACA | 61 |
| GCGTGTATGACCTTCTCTA | 48 | GCGUGUAUGACCUUCUCUA | 55 | UAGAGAAGGUCAUACACGC | 62 |
| CGTGTATGACCTTCTCTAT | 49 | CGUGUAUGACCUUCUCUAU | 56 | AUAGAGAAGGUCAUACACG | 63 |
| GAGGCGTGTATGACCTTCT | 50 | GAGGCGUGUAUGACCUUCU | 57 | AGAAGGUCAUACACGCCUC | 64 |
| AGGCGTGTATGACCTTCTC | 51 | AGGCGUGUAUGACCUUCUC | 58 | GAGAAGGUCAUACACGCCU | 65 |
| GGCGTGTATGACCTTCTCT | 52 | GGCGUGUAUGACCUUCUCU | 59 | AGAGAAGGUCAUACACGCC | 66 |
| GTGTATGACCTTCTCTATC | 53 | GUGUAUGACCUUCUCUAUC | 60 | GAUAGAGAAGGUCAUACAC | 67 |

TABLE 4B

Selected C6 oligonucleotides, SEQ ID Nos: 68-133

| DNA Sequence | SEQ ID NO: | RNA Sequence | SEQ ID NO: | Reverse Complement | SEQ ID NO: |
|---|---|---|---|---|---|
| | 1186 | GCCAAACACTGTGTCAGGATTGAAA (SEQ ID NO: 68) | | | |
| CAAACACTGTGTCAGGATT | 69 | CAAACACUGUGUCAGGAUU | 76 | AAUCCUGACACAGUGUUUG | 83 |
| AACACTGTGTCAGGATTGA | 70 | AACACUGUGUCAGGAUUGA | 77 | UCAAUCCUGACACAGUGUU | 84 |
| ACACTGTGTCAGGATTGAA | 71 | ACACUGUGUCAGGAUUGAA | 78 | UUCAAUCCUGACACAGUGU | 85 |
| CACTGTGTCAGGATTGAAA | 72 | CACUGUGUCAGGAUUGAAA | 79 | UUUCAAUCCUGACACAGUG | 86 |
| CCAAACACTGTGTCAGGAT | 73 | CCAAACACUGUGUCAGGAU | 80 | AUCCUGACACAGUGUUUGG | 87 |
| GCCAAACACTGTGTCAGGA | 74 | GCCAAACACUGUGUCAGGA | 81 | UCCUGACACAGUGUUUGGC | 88 |
| AAACACTGTGTCAGGATTG | 75 | AAACACUGUGUCAGGAUUG | 82 | CAAUCCUGACACAGUGUUU | 89 |
| | 1259 | GCACCACCAACAAGCTGTCAGAGAA (SEQ ID NO: 90) | | | |
| CCAACAAGCTGTCAGAGAA | 91 | CCAACAAGCUGUCAGAGAA | 98 | UUCUCUGACAGCUUGUUGG | 105 |
| CCACCAACAAGCTGTCAGA | 92 | CCACCAACAAGCUGUCAGA | 99 | UCUGACAGCUUGUUGGUGG | 106 |
| ACCAACAAGCTGTCAGAGA | 93 | ACCAACAAGCUGUCAGAGA | 100 | UCUCUGACAGCUUGUUGGU | 107 |

TABLE 4B-continued

Selected C6 oligonucleotides, SEQ ID Nos: 68-133

| DNA Sequence | SEQ ID NO: | RNA Sequence | SEQ ID NO: | Reverse Complement | SEQ ID NO: |
|---|---|---|---|---|---|
| CACCACCAACAAGCTGTCA | 94 | CACCACCAACAAGCUGUCA | 101 | UGACAGCUUGUUGGUGGUG | 108 |
| ACCACCAACAAGCTGTCAG | 95 | ACCACCAACAAGCUGUCAG | 102 | CUGACAGCUUGUUGGUGGU | 109 |
| GCACCACCAACAAGCTGTC | 96 | GCACCACCAACAAGCUGUC | 103 | GACAGCUUGUUGGUGGUGC | 110 |
| CACCAACAAGCTGTCAGAG | 97 | CACCAACAAGCUGUCAGAG | 104 | CUCUGACAGCUUGUUGGUG | 111 |
| 2325 GGGACAGAAACAATCAGGATCTGAA (SEQ ID NO: 112) | | | | | |
| GAAACAATCAGGATCTGAA | 113 | GAAACAAUCAGGAUCUGAA | 120 | UUCAGAUCCUGAUUGUUUC | 127 |
| GGACAGAAACAATCAGGAT | 114 | GGACAGAAACAAUCAGGAU | 121 | AUCCUGAUUGUUUCUGUCC | 128 |
| ACAGAAACAATCAGGATCT | 115 | ACAGAAACAAUCAGGAUCU | 122 | AGAUCCUGAUUGUUUCUGU | 129 |
| AGAAACAATCAGGATCTGA | 116 | AGAAACAAUCAGGAUCUGA | 123 | UCAGAUCCUGAUUGUUUCU | 130 |
| GGGACAGAAACAATCAGGA | 117 | GGGACAGAAACAAUCAGGA | 124 | UCCUGAUUGUUUCUGUCCC | 131 |
| CAGAAACAATCAGGATCTG | 118 | CAGAAACAAUCAGGAUCUG | 125 | CAGAUCCUGAUUGUUUCUG | 132 |
| GACAGAAACAATCAGGATC | 119 | GACAGAAACAAUCAGGAUC | 126 | GAUCCUGAUUGUUUCUGUC | 133 |

TABLE 4C

Selected C6 oligonucleotides, SEQ ID Nos: 134-199

| DNA Sequence | SEQ ID NO: | RNA Sequence | SEQ ID NO: | Reverse Complement | SEQ ID NO: |
|---|---|---|---|---|---|
| 2331 GAAACAATCAGGATCTGAATGCATT (SEQ ID NO: 134) | | | | | |
| GAAACAATCAGGATCTGAA | 135 | GAAACAAUCAGGAUCUGAA | 142 | UUCAGAUCCUGAUUGUUUC | 149 |
| AAACAATCAGGATCTGAAT | 136 | AAACAAUCAGGAUCUGAAU | 143 | AUUCAGAUCCUGAUUGUUU | 150 |
| CAATCAGGATCTGAATGCA | 137 | CAAUCAGGAUCUGAAUGCA | 144 | UGCAUUCAGAUCCUGAUUG | 151 |
| ATCAGGATCTGAATGCATT | 138 | AUCAGGAUCUGAAUGCAUU | 145 | AAUGCAUUCAGAUCCUGAU | 152 |
| ACAATCAGGATCTGAATGC | 139 | ACAAUCAGGAUCUGAAUGC | 146 | GCAUUCAGAUCCUGAUUGU | 153 |
| AATCAGGATCTGAATGCAT | 140 | AAUCAGGAUCUGAAUGCAU | 147 | AUGCAUUCAGAUCCUGAUU | 154 |
| AACAATCAGGATCTGAATG | 141 | AACAAUCAGGAUCUGAAUG | 148 | CAUUCAGAUCCUGAUUGUU | 155 |
| 2335 CAATCAGGATCTGAATGCATTTGTA (SEQ ID NO: 156) | | | | | |
| GGATCTGAATGCATTTGTA | 157 | GGAUCUGAAUGCAUUUGUA | 164 | UACAAAUGCAUUCAGAUCC | 171 |
| CAATCAGGATCTGAATGCA | 158 | CAAUCAGGAUCUGAAUGCA | 165 | UGCAUUCAGAUCCUGAUUG | 172 |
| TCAGGATCTGAATGCATTT | 159 | UCAGGAUCUGAAUGCAUUU | 166 | AAAUGCAUUCAGAUCCUGA | 173 |
| ATCAGGATCTGAATGCATT | 160 | AUCAGGAUCUGAAUGCAUU | 167 | AAUGCAUUCAGAUCCUGAU | 174 |
| AGGATCTGAATGCATTTGT | 161 | AGGAUCUGAAUGCAUUUGU | 168 | ACAAAUGCAUUCAGAUCCU | 175 |
| AATCAGGATCTGAATGCAT | 162 | AAUCAGGAUCUGAAUGCAU | 169 | AUGCAUUCAGAUCCUGAUU | 176 |
| CAGGATCTGAATGCATTTG | 163 | CAGGAUCUGAAUGCAUUUG | 170 | CAAAUGCAUUCAGAUCCUG | 177 |
| 2663 GCTTCAAGGGTGGAAACCAACTCTA (SEQ ID NO: 178) | | | | | |
| CTTCAAGGGTGGAAACCAA | 179 | CUUCAAGGGUGGAAACCAA | 186 | UUGGUUUCCACCCUUGAAG | 193 |
| TCAAGGGTGGAAACCAACT | 180 | UCAAGGGUGGAAACCAACU | 187 | AGUUGGUUUCCACCCUUGA | 194 |
| AGGGTGGAAACCAACTCTA | 181 | AGGGUGGAAACCAACUCUA | 188 | UAGAGUUGGUUUCCACCCU | 195 |
| GCTTCAAGGGTGGAAACCA | 182 | GCUUCAAGGGUGGAAACCA | 189 | UGGUUUCCACCCUUGAAGC | 196 |

TABLE 4C-continued

Selected C6 oligonucleotides, SEQ ID Nos: 134-199

| DNA Sequence | SEQ ID NO: | RNA Sequence | SEQ ID NO: | Reverse Complement | SEQ ID NO: |
|---|---|---|---|---|---|
| CAAGGGTGGAAACCAACTC | 183 | CAAGGGUGGAAACCAACUC | 190 | GAGUUGGUUUCCACCCUUG | 197 |
| AAGGGTGGAAACCAACTCT | 184 | AAGGGUGGAAACCAACUCU | 191 | AGAGUUGGUUUCCACCCUU | 198 |
| TTCAAGGGTGGAAACCAAC | 185 | UUCAAGGGUGGAAACCAAC | 192 | GUUGGUUUCCACCCUUGAA | 199 |

TABLE 4D

Selected C6 oligonucleotides, SEQ ID Nos: 200-221
2727 GAACATCTGTGAAGTGGGAACTATA (SEQ ID NO: 200)

| DNA Sequence | SEQ ID NO: | RNA Sequence | SEQ ID NO: | Reverse Complement | SEQ ID NO: |
|---|---|---|---|---|---|
| GAACATCTGTGAAGTGGGA | 201 | GAACAUCUGUGAAGUGGGA | 208 | UCCCACUUCACAGAUGUUC | 215 |
| CTGTGAAGTGGGAACTATA | 202 | CUGUGAAGUGGGAACUAUA | 209 | UAUAGUUCCCACUUCACAG | 216 |
| ATCTGTGAAGTGGGAACTA | 203 | AUCUGUGAAGUGGGAACUA | 210 | UAGUUCCCACUUCACAGAU | 217 |
| TCTGTGAAGTGGGAACTAT | 204 | UCUGUGAAGUGGGAACUAU | 211 | AUAGUUCCCACUUCACAGA | 218 |
| AACATCTGTGAAGTGGGAA | 205 | AACAUCUGUGAAGUGGGAA | 212 | UUCCCACUUCACAGAUGUU | 219 |
| ACATCTGTGAAGTGGGAAC | 206 | ACAUCUGUGAAGUGGGAAC | 213 | GUUCCCACUUCACAGAUGU | 220 |
| CATCTGTGAAGTGGGAACT | 207 | CAUCUGUGAAGUGGGAACU | 214 | AGUUCCCACUUCACAGAUG | 221 |

TABLE 4E

Selected C6 oligonucleotides, SEQ ID Nos: 222-251

|  |  |  | SEQ ID NO: |
|---|---|---|---|
| 2758 | GCAAACAGGAAGATGGAAA | target | 222 |
|  | GCAAACAGGAAGAUGGAAA | RNA | 223 |
|  | UUUCCAUCUUCCUGUUUGC | Reverse complement | 224 |
| 132 | GAGCAGACACAGACAAATA | target | 225 |
|  | GAGCAGACACAGACAAAUA | RNA | 226 |
|  | UAUUUGUCUGUCUGCUG | Reverse complement | 227 |
| 726 | GGTACAAAACTGCAGAAGAT | target | 228 |
|  | GGUACAAACUGCAGAAGAU | RNA | 229 |
|  | AUCUUCUGCAGUUUGUACC | Reverse complement | 230 |
| 1266 | CAACAAGCTGTCAGAGAAA | target | 231 |
|  | CAACAAGCUGUCAGAGAAA | RNA | 232 |
|  | UUUCUCUGUCUGCUUGUUG | Reverse complement | 233 |
| 1992 | TGGAGAAGATGTTGAAATT | target | 234 |
|  | UGGAGAAGAUGUUGAAAUU | RNA | 235 |
|  | AAUUUCUUCATCUUCUCCA | Reverse complement | 236 |
| 450 | CTGCATTGCCAGAAAGTTA | target | 237 |
|  | CUGCAUUGCCAGAAAGUUA | RNA | 238 |
|  | UAACUUUCUGGCAAUGCAG | Reverse complement | 239 |
| 157 | GATAAGTACTACCAGGAAA | target | 240 |
|  | GAUAAGUACUACCAGGAAA | RNA | 241 |
|  | UUUCCUGGUGUACUUAUC | Reverse complement | 242 |
| 1809 | GGAGAAGCGACAAGAGGAA | target | 243 |
|  | GGAGAAGCGACAAGAGGAA | RNA | 244 |
|  | UUCCUCUUGUCGCUUCUCC | Reverse complement | 245 |
| 566 | GTGTACAGTTGATGGGCAA | target | 246 |
|  | GUGUACAGUUGAUGGGCAA | RNA | 247 |
|  | UUGCCCAUCAACUGUACAC | Reverse complement | 248 |
| 1644 | TGGTGAGAACTGTGAGAAA | target | 249 |
|  | UGGUGAGAACUGUGAGAAA | RNA | 250 |
|  | UUUCUCACAGUUCUCACCA | Reverse complement | 251 |

Table 5A-F: Sequences of human (SEQ ID NO:1), rat (SEQ ID NO: 402) and mouse (SEQ ID NO: 403) complement component 6 (C6). Also shown (shaded boxes) are selected oligomer sequences from the human, rat and mouse (SEQ ID Nos: 252-401).

TABLE 5A

Selected C6 cross-species olimers
SEQ ID NOs: 252-401

```
human_c6   TTGCCTTGTGTTAGCTAGCAATAAGAAAAGAAGCTTTGTTTGGATTAACATATATACCCT
hu_c6_mrnaTTGCCTTGTGTTAGCTAGCAATAAGAAAAGAAGCTTTGTTTGGATTAACATATATACCCT
rat_C6     ------------------------------------------------------------
mouse_c6   --------------------TAGTATGAAGGACGCTTTGGATGCTCACACAAACCCC
```

TABLE 5A-continued

Selected C6 cross-species olimers
SEQ ID NOs: 252-401

```
human_c6   C-TTCATTCTGCATACCTATTTTTTCCCCAATAATTTGCAGCTTAGGTCCGAGGACACCA
hu_c6_mrna C-TTCATTCTGCATACCTATTTTTTCCCCAATAATTTGCAGCTTAGGTCCGAGGACACCA
rat_C6     ------------------------------------------------------------
mouse_c6   TGCTTAGCGTGCGTGTCTTTGGTTTCTACATCCATT--CAGGTT---CCTGAGCACAACT   SEQ ID NO' human_c6   CAAACTCTGCTTAAAGGGCCTGGAGGCTCTC-AAGGCATGGCCAGACGCTCTGTCTTGTA   252-253
hu_c6_mrna CAAACTCTGCTTAAAGGGCCTGGAGGCTCTC-AAGGCATGGCCAGACGCTCTGTCTTGTA
rat_C6     -------------------------------AGGCATGACGAGACATCTCACCTTGTG
mouse_c6   AAGGTCGATTTGAAAGGGTCTGGAGATTGTGGAAGGCATGACCAGACATCTCACCTTGTG
                                          ***** **      *** human_c6   CTTCATCCTGCTGAATGCTCTGATCAACAAGGGCCAAGCCTGCTTCTGTGATCACTATGC   254-255
hu_c6_mrna CTTCATCCTGCTGAATGCTCTGATCAACAAGGGCCAAGCCTGCTTCTGTGATCACTATGC
rat_C6     TTTCATTTTGCTGATCATACTGATTGACAAGAGTGAAGCCTGTTTCTGTGACCACTACCC
mouse_c6   TTTCATTTTGCTGGTCATGCTGATTGACAAGAGTGAAGCCTGTTTCTGTGACCACTACCC
           ***  *    *  ***  *  ***** ***** ***  * human_c6   ATGGACTCAGTGGACCCAGCTGCTCAAAAACTTGCAATTCTGGAACCCAGAGCAGACACAG   256-257
hu_c6_mrna ATGGACTCAGTGGACCCAGCTGCTCAAAAACTTGCAATTCTGGAACCCAGAGCAGACACAG   258
rat_C6     ATGGACTCACTGGTGGAGCTGTTCTAAGTCCTGCAATTCTGGAACCCAGAGCAGACAGAG
mouse_c6   ATGGACTCACTGGTGGAGCTGTTCTAAGTCCTGCAATTCTGGAACCCAGAGCACACAGAG
           ******* * * *      * *********************** human_c6   ACAAATAGTAGTAGATAAGTACTACCAGGAAAACTTTTGTGAACAGATTTGCAGCAAGCA
hu_c6_mrna ACAAATAGTAGTAGATAAGTACTACCAGGAAAACTTTTGTGAACAGATTTGCAGCAAGCA
rat_C6     ACAAATCGTAGTGAACGATTACTATCGGGATAACTCATGCGATCAGCTCTGTACCAAGCA
mouse_c6   ACAAGTAGTAGTGAACGATTACTATTGGAAAAACTTATGCGATAAGCTTTGTATCAAGCA
           **  **** *   ****       *        ****** human_c6   GGAGACTAGAGAATGTAACTGGCAAAGATGCCCCATCAACTGCCTCCTGGGAGATTTTGG   259-260
hu_c6_mrna GGAGACTAGAGAATGTAACTGGCAAAGATGCCCCATCAACTGCCTCCTGGGAGATTTTGG
rat_C6     GGAGACCAGACAGTGCAACGTGGAGACATGTCCCATCAACTGTGTCCTAGGAGACTATGG
mouse_c6   GGAGACCAGAGAGTGCAACTTGCAGACATGTCCCATCAACTGTGTCCTAGGAGACTATGG
           ****  *   **  *  *   * * *****    * ***** * *** human_c6   ACCATGGTCAGACTGTGACCCTTGTATTGAAAAACAGTCTAAAGTTAGATCTGTCTTGCG   261
hu_c6_mrna ACCATGGTCAGTCTGTGACCCTTGTATTGAAAAACAGTCTAAAGTTAGATCTGTCTTGCG   262-264
rat_C6     AACATGGTCAGACTGTGACCCTTGTATTAGAAAACAGGTTAAAGTTAGATCTGTTCTGCG
mouse_c6   GACATGGTCAGACTGTGACCCTTGTACTGAAAAACAGGTTAAAGTTAAATCTGTCCTGCG
             ******* ***********  *** ***** *  ** human_c6   TCCCAGTCAGTTTGGGGGACAGCCATGCACTGCGCCTCTGGTAGCCTTTCAACCATGCAT
hu_c6_mrna TCCCAGTCAGTTTGGGGGACAGCCATGCACTGAGCCTTTGGTAGCCTTTCAACCATGCAT   265-267
rat_C6     CCCAAGTCAGTTTGGGGGACAACCATGCACAGAGGCCCCTGGTGACCTTTCAAGCATGTGT   268
mouse_c6   CCCAAGTCAGTTTGGGGGGCAACCATGCACAGAGGCCCTGGTGACCTTTCAACCATGTGT
             *********   ********  *  * *  *******   * human_c6   TCCATCTAAGCTCTGCAAAATTGAAGAGGCTGACTGCAAGAATAAATTTCGCTGTGACAG   269-271
hu_c6_mrna TCCATCTAAGCTCTGCAAAATTCAAGAGGCTGACTCCAAGAATAAATTTCGCTGTGACAG
rat_C6     CCCATCTGAGCTCTGCAAAATTGAAGAGACTGATTGCAAGAATAAATTCCTCTGTGACAG
mouse_c6   CCCCTCCAAGCTCTGCAAAATTGAAGAGACTAAGTGCAAGAATAAGTTCCTCTGTGACAG
             ** ****************  *****  **    **********  **  *********
```

TABLE 5B

```
human_c6   TGGCCGCTGCATTGCCAGAAAGTTAGAATGCAATGGAGAAAATGACTGTGGAGACAATTC   272-273
hu_c6_mrna TGGCCGCTGCATTGCCAGAAAGTTAGAATGCAATGGAGAAAATCACTGTGGAAACAATTT
rat_C6     TGGGCCCTGTATTCCCAGCAAGTTAAAATGCAATGGAGAGAATCACTGTGGAAACAATTT
mouse_c6   TGGGCCCTGTATTCCCAGCAAGTTAGAATGCAATGGAGAGAATCACTGTGGAAACAATTT   274-275
           *  * * * ** ********* * ******  *** human_c6   AGATGAAAGGGACTGTGGGAGCACAAAGGCAGTATGCACACGGAAGTATAATCCCATCCC
hu_c6_mrna AGATGAAAGGGACTGTGGGAGCACAAAGGCAGTATGCACACGGAAGTATAATCCCATCCC   276-277
rat_C6     AGACGAAAGGAACTGTGGGAGGACAAAGGCAGTATGCTCACACAGAATATAATCCTCTATCCC
mouse_c6   AGATGAAAGGAACTGTGGGAGGACAAAGGCCAGTATGCACACGGATATACACTCCCATCCC   278-280
           *** ****** ********** *******  ****** ***  **  ***  *** *****
```

TABLE 5B-continued

```
human_c6   TAGTGTACAGTTGATGGGCAATGGGTTTCATTTTCTGGCAGGAGAGCCCAGAGGAGAAGT  290-291
hu_c6_mrna TAGTGTACAGTTGATGGGCAATGGGTTTCATTTTCTGGCAGGAGAGCCCAGAGGAGAAGT
rat_C6     CAGTGTGCAGCTGATGGGCGCTGGGTTTCATTTTCTGGCAGGAGAGCCCAGGGAGATGT
mouse_c6   TAGTGTGCAGCTGATGGGCACTGGGTTTCACTTTCTGGCAGGAGAGCCCAGAGGAGAAGT  292
           * ** * ****** ***** *******************  ** human_c6   CCTTGATAACTCTTTCACTGGAGGAATATGTAAAACTGTCAAAAGCAGTAGGACAAGTAA  293-295
hu_c6_mrna CCTTGATAACTCTTTCACTGGAGGAATATGTAAAACTGTCAAAAGCAGTAGGACAAGTAA
rat_C6     CCCTGATAACTCCTTCAGTGGAGGAATATGTAAATCCGTCAGGAGCAGCCGAACGAGTAA
mouse_c6   TCTTGACAACTCTTTCACTGGACCAATATGTAAACTTGTCAAGACCAGTCGAGCCAGTAA
           * * **   ******* *** * *** *  * ***** human_c6   TCCATACCGTGTTCCCCCAATTTGGAAAATGTCGGCTTTGACCCTACAAACTGTCGAAGA  296-298
hu_c6_mrna TCCATACCGTGTTGCGGCCAATCTGGAAAATGTCGGCTTTGAGGTACAAACTGCAGAAGA
rat_C6     TCCACACCCAGTTCCAGCCAATCTTGAAAATTTCAACTTTGAGGTAGAAACTATAGAAGA
mouse_c6   TCCATACCCTGTTTCACCCAATCTGGAAAATGTCAACTTTCAGCTACAAACTATAGAACA  299-301
           ** *  ***    * **** * ***  * *** *   * **     * human_c6   TGACTTGAAAACAGATTTCTACAAGGATTTAACTTCTCTTGGACACAATGAAAATCAACA
hu_c6_mrna TGACTTGAAAACAGATTTCTACAAGGATTTAACTTCTCTTGGACACAATGAAAATCAACA  302-303
rat_C6     TGACTTGAAAACAGATTTCTACAAGGATTTAGCCACTATTGGAAAAAATAAAAATGAAGA
mouse_c6   TGACTTGAAAACAGATTTCTACAAGAATTTAATCTCTTTTGAAAAAAATAAAAATGAAGA
           *********************** *   * ** *    * *  * human_c6   AGGCTCATTCTCAAGTCAGGGGGGGAGCTCTTTCAGTGTACCAATTTTTTATTCCTCAAA  304-306
hu_c6_mrna AGGCTCATTCTCAAGTCAGGGGGGGAGCTCTTTCAGTGTACCAATTTTTTATTCCTCAAA
rat_C6     CCGTTCATTGTCTGGTGAGAAGAAAGACTCTTTCTACGTACCAATTTTTTATTCCTGAAA
mouse_c6   CAGTCTTTCAGTGGATGAAAGGACAAAATTTTTCCCTATACCAATTTCTGATTTCTCAGA
              *       *   *       *     * **      ****   *   * human_c6   GAGAAGTGAAAATATCAACCATAATTCTGCCTTCAAACAAGCCATTCAAGCCTCTCACAA  307-309
hu_c6_mrna GAGAAGTGAAAATATCAACCATAATTCTGCCTTCAAACAAGCCATTCAAGCCTCTCAGAA
rat_C6     GAAAAGTGAAAATTTCCAACGTAACTCAGGCTTCAAAAACGCCATTGAAGCCTCCCAGAA
mouse_c6   GAAAAATGAACATTCCCATTATAGCTCTGCCTTCAACAAAGTCATTAAAGCTTCCCACAA
             **     *   *   * ****** *    * *   ** human_c6   AAAGGATTCTAGTTTTATTAGGATCCATAAAGTGATGAAAGTCTTAAACTTCACAACGAA  310-312
hu_c6_mrna AAAGGATTCTAGTTTTATTAGGATCCATAAAGTGATGAAAGTCTTAAACTTCACAACGAA
rat_C6     GAAGGATTCGAGCTTTGTTAGGATCCATAAGTGATAAAAGTCTTAACTTCACAATGAA
mouse_c6   GAAGGATTCTAGCTTTATCAGGATCCATAAGCTGATAAAAGTCTTAAACTTCACAATGAA
           *****   *  *******     *  ****** **** * human_c6   AGCTAAAGATCTGCACCTTTCTGATGTCTTTTTGAAAGCACTTAACCATCTGCCTCTAGA  313-314
hu_c6_mrna AGCTAAAGATCTGCACCTTTCTGATGTCTTTTTGAAAGCACTTAACCATCTGGCTCTAGA
rat_C6     AACGACAGACCTGCAGCTCTCAGACGTCTTCCTAAAAGCCCTCATCCACCTGCCTTTAGA
mouse_c6   AGCAACAGACCTACAGCTTTCAGATGTCTTCCTGAAAGCCCTTGTCCACCTGCCTTTAGA
           * *  * *       *****  * ***    * * **** human_c6   ATACAACTCTGCTTTGTACAGCCCAATATTCCATGACTTTGGGACTCATTACTTCACCTC
hu_c6_mrna ATACAACTCTGCTTTGTACAGCCCAATATTCGATGACTTTGGGAGTCATTACTTCACCTC  315-317
rat_C6     ATACAACTTTGCTTTGTACAGCCCGATATTTGATGACTTTGGGACCCACTATTTCACCTC  318-320
mouse_c6
```

TABLE 5C

```
mouse_c6   ATACAACTCTGCTGTGTACAGCCGGATATTTGATGACTTCGGGACCCACTACTTCACCTC
           ****** * * ****** *  *** *     ***** human_c6   TGGCTCCCTGGGAGGCGTGTATGACCTTCTCTATCAGTTTAGCAGTGAGGAACTAAAGAA  321-322
hu_c6_mrna TGCCTCCCTGGGAGGCGTGTATGACCTTCTCTATCAGTTTAGCAGTGAGGAACTAAAGAA
rat_C6     AGGCTCCCTTGGGCAAGTATGACCTTCTACCAATTCAGCCGCCAGGAGCTACAGAA
mouse_c6   AGGGTGGCTTGGGGGCAAGTATCACCTTATCTACCAATTCAGCCGCCAGGAGCTACAGAA
            *  *   **  *   * ****   **  *  *    * * * human_c6   CTCAGGTTTAACCGAGGAAGAAGCCAAACACTGTGTCACGATTGAAACAAACAAACGCGT  323-324
hu_c6_mrna CTCAGGTTTAACCGAGGAAGAAGCCAAACACTGTGTCACGATTGAAACAAAGAAACGCGT
rat_C6     CTCAGGTTTAACAGAAGAAGAAACTCGAAACTGTGTCCGGTATGAAACAAAGAAACGTTT
mouse_c6   CTCAGCTTTAACACAAGAAGAAGCTCAAAACTGTGTCCAGTATGAAACTAAGAAACTTAA  325-327
           ***  *** * * ***** *   * ******** * * ****  ***** human_c6   TTTATTTGCTAAGAAAACAAAAGTGGAACATAGGTGCACCACCAACAAGCTGTCAGAGAA
hu_c6_mrna TTTATTTGCTAAGAAAACAAAAGTGGAACATAGGTGCACCACCAACAAGCTGTCAGAGAA
rat_C6     CTTATTTTTACGAAAACATACAAGGAAGACCGGTGTACCACAAATAGGCTGTCTGAAAA
mouse_c6   GTTTCTTTATATGGAAATACACAAGGAAGACACGTGCACCAAAAACAAGCTGTCTGAAAA
             ** **     * ***  *      * ** *  *** *** *    *  * ***** **
```

TABLE 5C-continued

```
human_c6    ACATGAAGGTTCATTTATACAGGGAGCACAGAAATCCATATCCCTGATTCGAGGTGGAAG  328-330
hu_c6_mrnaACATGAAGGTTCATTTATACAGGGAGCAGAGAAATCCATATCCCTGATTCGAGGTGGAAG
rat_C6      GTACAAAGGTTCCTTTTTACAGGGATCGGAGAAATCTATATCCCTGGTCCAGGGCGGGAG  331-333
mouse_c6    ATATGGAGGTTCCTTTTTGCAGGGATCAGAGAAATCCATTTCCCTGGTCCAGGGCGGGAG
              *  ****  *  *  ******  *  ******    ***  **  *    * human_c6    GAGTGAATATGGAGCAGGTTTGGCATGGCAGAAAGGGAGCTCTGGTCTGGACGAGAAGAC  337-338
hu_c6_mrnaGAGTGAATATGGAGCACCTTTCGGATGGGAGAAAGGGAGCTCTGGTCTGGAGGAGAAGAC
rat_C6      GAGTCAGCAGGCAGCAGCCTTGGCTTGGGAGAAGGGCAGCTCTGGTCCAGAGGCGAATGT  399-341
mouse_c6    GAGTCAGCAGGCAGCAGCCYYGGCYYGGGAGAAGGGCACCTCTGGTCCAGAGGAGAATGT
            ****  *    *  *  ****  *  ****    *  ******      * human_c6    ATTTTCTGAGTGGTTAGAATCAGTGAAGGAAAATCCTGGTGTGATTGACTTTGAGCTTGC  342-344
hu_c6_mrnaATTTTCTGAGTGGTTAGAATCAGTGAAGGAAAATCGTGCTGTGATTCACTTTGAGCTTGC
rat_C6      CTTCTCTGAGTGGTTAGAGTCGGTGAAGGAAAACCCTGCTGTGGTTGATTATGAGCTTGC
mouse_c6    CTATTCTGAGTGGCTAGAATCGGTGAAGGAAAACCGTGCTGTAGTTGATTATAAGCTTGC  345-347
              *   ***********  *    *******    ****  *  *  *  ******* human_c6    CCCCATCGTGCACTTGGTAAGAAACATCCCCTGTCCAGTGACAAAAGGGAACAAGCTCAG  348-349
hu_c6_mrnaCCCCATCGTGGGACTTGGTAAGAAACATCCCCTGTGCAGTGACAAAACGGAACAACCTCAG
rat_C6      TCCGATCATCGAGTTGGTCAGAAACATCCCCATGTGCAGTCAGTGACAAAAGGGAAGAACCTCAG  350
mouse_c6    CCCAATTACAGACTTGGTCAGAAACATCCCCATGTGCAGTGACAAAAGGGAAGAAGGTCAG
                    ******    *****  ****  *************** human_c6    GAAAGCTTTGCAAGAGTATGCAGCCAAGTTCGATCCTTGCCAGTGTGCTCCATGCCCTAA  351-352
hu_c6_mrnaGAAAGCTTTGCAAGAGTATGCACCCAAGTTCGATCCTTGCCAGTGTGCTCCATGCCCTAA
rat_C6      GAAAGCCCTTCAAGAATATGGAGCCAAGTTTGACCCTTGCCAATGTGCTCCATGTCCTAA  353-354
mouse_c6    GAGAGCGCTTCAAGAGTATGCACCCAAGTTTGACCCTTGCCAGTGTGCTCCATGTCCCAA
                *    *  *  ***  ***********    *********    ** human_c6    TAATGGCCGACCCCACCCTCTCAGGGACTGAATGTCTGTGTGTGTGTGACAGTGGCACCTA
hu_c6_mrnaTAATGGCCCACCCACCCTCTCAGGGACTGAATCTCTGTCTGTGTGTCAGACTGGCACCTA  355-356
rat_C6      TAATGGCCGCCCCAGGCTCTCAGGCACAGAATGTTTGTGTGTGTGCCAGACTGGTACCTA  357-358
mouse_c6    TAATGGCCCCCCCAGGCTCTCAGGCACGGAATGCCTGTGTGTGTGCCAGAGCGGCACCTA  359-361
            *******        *******    *      *    *  ******** human_c6    TGGTGQGGQCTGTGAGAAACAGTCTCCAGATTATAAATCCAATGCAGTAGACGGACAGTG
hu_c6_mrnaTGGTGAGAACTGTGAGAAACAGTCTCCAGATTATAAATCCAATGCAGTAGACGGACAGTG  362
rat_C6      CGGTGAGAACTGTGAAAAACGGTCCCCAGATTATAAATCGAATGCAGTGGATGGGAACTG  363-365
mouse_c6    CGGTGAGAACTGTGAGCGCAGGTCCCCAGGTTACAAATCTGATGCAGTGGATGGAAACTG
              *************    ***  ****  ***  *****  *******  **  **    *  **
```

TABLE 5D

```
human_c6    GGGTTGTTGGTCTTCCTGGAGTACCTGTGATGCTACTTATAAGAGATCGAGAACCCGAGA  366-367
hu_c6_mrnaGGGTTGTTGCTCTTCCTGGAGTACCTGTGATGCTACTTATAAGAGATCGAGAACCCGAGA
rat_C6      GGCCTGCTGGTCTTCCTGCAGCGCATGCAATGCTGCTTATACGAGGTCAAGGAGCCGGGA  368-369
mouse_c6    (?)CTGCTGGTCTTCCTGGAGTGCGTGCAATGCTCCTTATAGGAGATCAAGAACCCGAGA
            ***  **  ***********    *  **    *****  ******  ***  **  **  *  ***  **

243
human_c6    ATGCAATAATCCTGCCCCCCAACGAGGAGGGAAACGCTGTGAGGGGGAGAAGCGACAAGA  370-372
hu_c6_mrnaATGCAATAATCCTGCCCCCCAACGAGGAGGGAAACGCTGTGAGGGGGAGAAGCGACAAGA
rat_C6      GTGTAATAACCCTGAGCCACACGCGAGGAGGGCGCGCTGTGAGGGGCAAGCATTGGCAAGA
mouse_c6    GTGTAATAACCCTGCGCCACAGCGAGGAGGACAAAAGCTGTGGTGGCAAGGATCAGCAAGA
                *          ****      **        **  *      ***** human_c6    GAAAGACTGCACATTTTCAATCATGAAAACAATGGACAACCATGTATCAATCATGATGA  373-375
hu_c6_mrnaGAAAGACTGCACATTTTCAATCATGAAAACAATGGACAACCATGTATCAATGATGATGA
rat_C6      AGAAGACTGTACATTCTCAATAATGGAAAAGTTGGACAACCCTGCATCAGTGATGATGA
mouse_c6    AGAAGACTGTACAGTCTCAATAATGGAAATGTTGGACAACCATGTATCAATGATGATGA  376-377
              ******  *  *  ***  ****    **    **  ******* human_c6    AGAAATGAAAGAGGTCGATCTTCCTGAGATAGAAGCAGATTCCGGCTGTCCTCAGCCAGT  378-380
hu_c6_mrnaAGAAATGAAAGAGGTCGATCTTCCTGAGATAGAAGCAGATTCCGGGTGTCCTCAGCCAGT
rat_C6      AGAAATAAAAGAAGTAGACCTTGCTGAGCCAGAAGCAGATTCAGGGTGTCCTCAGCCACC
mouse_c6    AGAAATGACAGAGGTAGACCTTGCTGAGCCAGAAGCAGAATCAGGGTGTTCTCAACCACC
            ******  *  ***  **  *  **  **  *****  ********  ******  **  ******  ***

234
human_c6    TCCTCCAGAAAATGGATTTATCCGGAATGAAAAGCAACTATACTTGGTTGGAGAAGATGT
hu_c6_mrnaTCCTCCAGAAAATGGATTTATCCGGAATGAAAAGCAACTATACTTGGTTGGAGAAGATGT  381-383
rat_C6      TCTCCCAGAAAATGCATTTGTCTGGAATGAAAAGAAACTGTACTCAGTCGGGGAGGAAGT
mouse_c6    TCTCCCAGAAAACGCATTTACCTGGAATGACAAGAAACTGTACTCAGTTGGGGAGGAAGT
              **  ********  *  ****  *  ****    *********  *****    ****  **  **  **
```

TABLE 5D-continued

```
human_c6    TGAAATTTCATGCCTTACTGGCTTTGAAACTGTTGGATACCAGTACTTCACATGCTTACC  384-386
hu_c6_mrna  TGAAATTTCATGCCTTACTGGCTTTGAAACTGTTGGATACCAGTACTTCACATCCTTACC
rat_C6      TGAAATTTCATGTCTCACTGGATTCAAAGCTGTGGGATACCAGTACTT        TACC
mouse_c6    TGAAATTTCATGTCTTACTGGATTCACAGCTGTTGGATTCCAGTACTTGAGATGTTTACC  387-388
            *********    *****  *  * **  ***** * *** human_c6    AGACGGGACCTGGAGACAAGGGGATGTGGAATGCCAACGGACGGAGTGCATCAAGCCAGT  389-391
hu_c6_mrna  AGACGGGACCTGGAGACAAGGGGATGTGGAATGCCAACGGACGGAGTGCATCAAGCCAGT
rat_C6      AGACAGAACCTGGAGCCAACGGGATGTCGAATGCCAACGGACCGAGTGCCTCAAACCAGT
mouse_c6    AGACAGAACCTGGAGTCAAGGAGATGTGGAATGCCAAAGGACCTCGTGCCTCAAGCCCGT
            ****  * *****   *  ** ****      * **   ** human_c6    TGTGCAGGAAGTCCTGACAATTACACCATTTCAGAGATTGTATAGAATTGGTGAATCCAT
hu_c6_mrna  TGTGCAGGAAGTCCTGACAATTACACCATTTCAGAGATTGTATAGAATTGGTGAATCCAT  392-393
rat_C6      CGTTCAGGATGTCCTGAGGATCTCCCCATTTCAGAGTGTGTACAAGATTGGGGAATCCAT
mouse_c6    TGTTCAGGATGTCCTGACCATCTCCCCATTTCACAAAGTGTATCAGATTGGGCAATCCAT  394-395
             *  ***  *  ***** *  * *   ** ***** human_c6    TGAGCTAACTTGCCCCAAAGGCTTTGTTGTTGCTGGGCCATCAAGGTACACATGGCAGGG  396-398
hu_c6_mrna  TGAGCTAACTTGCCCCAAAGGCTTTGTTGTTGCTGGGCCATCAAGGTACACATGCCAGGG
rat_C6      TGAGCTGACCTGTCCCAGAGGCTTTGTTGTTGCTGGCCCATCGAGGTATACATGCAAGGA
mouse_c6    TGAGCTGACATGCCCCAGAGGCTTTGTTGTTGCTGGACCATCAAGGTATACATGCAAGGA
            ****     *************    *   * human_c6    GAATTCCTGGACACCACCCATTTCAAACTCTCTCACCTGTGAAAAAGATACTCTAACAAA  399-401
hu_c6_mrna  GAATTCCTGGACACCACCCATTTCAAACTCTCTCACCTGTGAAAAAGATACTCTAACAAA
rat_C6      AGACTCCTGGACACCTCCCATTCCAAATTCTGAGCTGTGAAACAAGATATTCTGACAAA
mouse_c6    AGACTCCTGGAGACCTCCCATTTCAAATTCATTGACCTGTGAACAAGGTGTCAGAGACCA
            **  ***** *  ** ****** * ** **  *  *  **  ** ***   *       *

111         134         156
human_c6    ATTAAAAGGCCATTGTCAGCTGGGACAGAAACAATCAGGATCTGAATGCATTTGTATGTC
hu_c6_mrna  ATTAAAAGGCCATTGTCAGCTGGGACAGAAACAATCAGGATCTGAATGCATTTGTATGTC
rat_C6      GTCAAAGGGCCTTTGTCAACCAGGACAAAAGCAATCAGGATCCGAGTGTGTTTGTATGTC
```

TABLE 5E

```
mouse_c6    TCCGTGAGAAATGATC--CCTTCACAATCTCCTTAACAAGTCAAAGGGCCTTGAA----
                *   *  ** *   ***     *   *  *    *  *  *  * human_c6    TCCAGAAGAAGACTGTAGCCATCATTCAGAAGATCTCTGTGTGTTTGACACAGACTCCAA
hu_c6_mrna  TCCAGAAGAAGACTGTAGCCATCATTCAGAAGATCTCTGTGTGTTTGACACAGACTCCAA
rat_C6      CCCAGAAGAAGACTGTAGCAGTTATTCGGAAGATCTCTGTATATTTGATGAGGGATCCAG
mouse_c6    -CTAAGAGCTGGTTGCCACCCCCTTCCTCCTTATTCCCTCCTAACACCTAAGGCTGTAA
            *                   *             *          * * human_c6    CGATTACTTTACTTCACCCGCTTGTAAGTTTTTGGCTGAGAAATGTTTAAATAATCAGCA
hu_c6_mrna  CGATTACTTTACTTCACCCGCTTGTAAGTTTTTGGCTGAGAAATGTTTAAATAATCAGCA
rat_C6      TCAGTACTTCACTTCATCTGCTTGCAAATTTTTGGCTGAAAAATGTTTAAACAGCAACCA
mouse_c6    AATTTGAATAACAGTCCCCTCTTCCCTATCTCTTTCCGAGTTCCCATGACATC-CAAGGA
                *   **   *   ***    * *  ***     * *   **    *   *  * human_c6    ACTCCATTTTCTACATATTGGTTCCTGCCAAGACGGCCGCCAGTTAGAATGGGGTCTTGA
hu_c6_mrna  ACTCCATTTTCTACATATTGGTTCCTGCCAAGACGGCCGCCAGTTAGAATGGGGTCTTGA
rat_C6      GTTCCACTTTGTCCATGCTGGTTCCTGCCAAGAAGGCCCACAGTTAGAATGGGGTCTTGA
mouse_c6    CATGAGCTGTGCCTGAGCCCAGCTTGACTCCCAAGGCTGTTGAGGAGGATCAAGGCTCTG
               *   * *        *     *          * *         **     * ** human_c6    AAGGACAAGACTTTCAT--CCAACAGCACAAAGAAAGAATCCTGTGGCTATGACACCTGC
hu_c6_mrna  AAGGACAAGACTTTCAT--CCAACAGCACAAAGAAAGAATCCTGTGGCTATGACACCTGC
rat_C6      GAGGCTAAAACTCGCAA--TGAAGAGCACAAAGAGAGTGCCCTGTGGATATGATACTTGC
mouse_c6    GAG-ATAAGATGCAAAGTGCCTGCTGCTTGGCGCCTGACTTCAGCCCCCATGTCAGCAGT
                       **   *        **    *      *  **   * * *  * human_c6    TATGACTGGGAAAAATGTTCAGCCTCCACTTCCAAATGTGTCTGCCTATTGCCCCCACAG
hu_c6_mrna  TATGACTGGGAAAAATGTTCAGCCTCCACTTCCAAATGTGTCTGCCTATTGCCCCCACAG
rat_C6      TATGACTGGGAAAAATGTTCAGCCCACACCTCCAACTGTGTCTGCCTATTGCCCCCACAA
mouse_c6    CGTCCTTTCCCTTGTTCTTTGTACAACTCTCCCTCGACCCCTCCCCTATTTTCCGCGATG
              *   *   *  **   *      **      *    **   **  ****  ** * *

178
human_c6    TGCTTCAAGGGTGGAAACCAACTCTACTGTGTCAAAATGGGATCATCAACAAGTGAGAAA
hu_c6_mrna  TGCTTCAAGGGTGGAAACCAACTCTACTGTGTCAAAATGGGATCATCAACAAGTGAGAAA
rat_C6      TGCCCCAAGGATGAAAACCAACTCCACTGTGTCAAAATGGGATCATCAATGCGTGGGAAA
mouse_c6    TATGCTTTATAAGGAAAGCACCTCAGCTTAAT--AAATGAGACC-TTGATAGGTTTAATC
             *         *  ***  **  *** * *    ** * *   *  * *  **       *
```

TABLE 5E-continued

```
                    200                  222
human_c6    ACATTGAACATCTGTGAAGTGGGAACTATAAGATGTGCAAACAGGAAGATGGAAATACTG
hu_c6_mrna  ACATTGAACATCTGTGAAGTGGGAACTATAAGATGTGCAAACAGGAAGATGGAAATACTG
rat_C6      ACAGTAAACATCTGTACACTGGGAGCCGTGAGGTGTGCAAACAGGAAGGTGGAAATACTG
mouse_c6    T----------------------------------------------------------- human_c6    CATCCTGGAAAGTGTTTGGCCTAGCACAATTACTGCTAGGCCCAGCACAATGAACAGATT
hu_c6_mrna  CATCCTGGAAAGTGTTTGGCCTAGCACAATTACTGCTAGGCCCAGCACAATGAACAGATT
rat_C6      AATCCTGGGAGGTGCTTGGATTAGCA------CTGCTAG--------TGATGAATGAATT
mouse_c6    ------------------------------------------------------------ human_c6    TACCATCCCGAAGAACCAACTCCTACAAATGAGAATTCTTGCACAAACAGCAGACTGGCA
hu_c6_mrna  TACCATCCCGAAGAACCAACTCCTACAAATGAGAATTCTTGCACAAACAGCAGACTGGCA
rat_C6      TATTATTC--AAAAACAACGGACAGGAATGAGGAAAGT-GAATGGATGGGAGCAAAGTA
mouse_c6    ------------------------------------------------------------ human_c6    TGCTCAAAGTTACTGACAAAAATTATTTTCTGTTAGTTTGAGATCATTATTCTCCCCTGA
hu_c6_mrna  TGCTCAAAGTTACTGACAAAAATTATTTTCTGTTAGTTTGAGATCATTATTCTCCCCTGA
rat_C6      TGATAACACATATCTTCAGGAATG------TAATGATAAAACCCATTACTTTGTAT--A
mouse_c6    ------------------------------------------------------------
```

TABLE 5F

```
human_c6    CTCTCCTGTTTGGGCATGTCTTATTCAGTTCCAGCTCATGACGCCCTGTAGCATACCCCT
hu_c6_mrna  CTCTCCTGTTTGGGCATGTCTTATTCAGTTCCAGCTCATGACGCCCTGTAGCATACCCCT
rat_C6      ATAACCTAAACAAAC---TCTTTTTTAAAAAAAACTCATTATA---TGTAAACTAACA-T
mouse_c6    ------------------------------------------------------------ human_c6    AGGTACCAACTTCCACAGCAGTCTCGTAAATTCTCCTGTTCACATTGTACAAAAATAATG
hu_c6_mrna  AGGTACCAACTTCCACAGCAGTCTCGTAAATTCTCCTGTTCACATTGTACAAAAATAATG
rat_C6      AGCCATAAATTGCTG--GCAAAAAAAAAAA----------AAAAAAAAAAAAAAAAA--
mouse_c6    ------------------------------------------------------------ human_c6    TGACTTCTGAGGCCCTTATGTAGCCTGTGACATTAAGCATTCTCGCAATTAGAAATAAGA
hu_c6_mrna  TGACTTCTGAGGCCCTTATGTAGCCTGTGACATTAAGCATTCTCACAATTAGAAATAAGA
rat_C6      ------------------------------------------------------------
mouse_c6    ------------------------------------------------------------ human_c6    ATAAAAC-----------------------------------------------------
hu_c6_mrna  ATAAAACCCATAATTTTCTTCAATGAGTTAATAAACAGAAATCTCCAGAACCTCTGAAAC
rat_C6      ------------------------------------------------------------
mouse_c6    ------------------------------------------------------------ human_c6    ------------------------------------------------------------
hu_c6_mrna  ACATTCTTGAAGCCCAGCTTTCATATCTTCATTCAACAAATAATTTCTGAGTGTGTATAC
rat_C6      ------------------------------------------------------------
mouse_c6    ------------------------------------------------------------ human_c6    ------------------------------------------------------------
hu_c6_mrna  AGGATGTCAAGTACTGACCAAAGTCCTGAGAACTCGGCAGATAATAAAACAGACAAAAGC
rat_C6      ------------------------------------------------------------
mouse_c6    ------------------------------------------------------------ human_c6    ------------------------------------------------------------
hu_c6_mrna  CTTTGCCTTCATGAAGCATACATTCATTCAGGGGTAGACACACAAAAAATGAAATAAACA
rat_C6      ------------------------------------------------------------
mouse_c6    ------------------------------------------------------------ human_c6    ---------------
hu_c6_mrna  GGTAAAATATGTAGC
rat_C6      ---------------
mouse_c6    ---------------
```

The invention claimed is:

1. An in vitro or in vivo method of reducing or inhibiting the expression of COMPLEMENT COMPONENT 6 (C6) in a cell or a tissue, comprising the step of contacting said cell or tissue with an antisense oligomer so that expression of the COMPLEMENT COMPONENT 6 (C6) is reduced or inhibited, wherein the oligomer is
   (a) between about 10 to 50 nucleotides in length having a contiguous nucleobase sequence with at least 80% sequence identity to a complementary region of a nucleic acid which encodes the COMPLEMENT COMPONENT 6 (C6) sequence represented by SEQ ID NO: 1, or a naturally occurring allelic variant thereof,
   (b) is targeted to about nucleotides 112-152, 433-473, 546-586, 706-746, or 1015-1055 from the ATG start site of SEQ ID NO: 1 (starting at the "A"),
   (c) comprises at least one nucleotide analogue, and (c) is capable of reducing the level of C6 mRNA expression in a mammal, and
   wherein the oligomer is
   (d) single-stranded, or
   (e) a gapmer comprising 2 or 3 locked nucleic acid (LNA) monomers at each of the 3' and 5' ends of the oligomer.

2. The method of claim 1, wherein the method further comprises the step of measuring at least one of the Complement Component 6 (C6), mRNA encoding the protein and a membrane attack complex (MAC) following administration of the oligomer.

3. An in vitro or in vivo method of reducing or inhibiting the production of a membrane attack complex (MAC) in a cell or a tissue, comprising the step of contacting said cell or tissue with an antisense oligomer so that expression of the MAC is reduced or inhibited, wherein the oligomer is
   (a) between about 10 to 50 nucleotides in length having a contiguous nucleobase sequence with at least 80% sequence identity to a complementary region of a nucleic acid which encodes the COMPLEMENT COMPONENT 6 (C6) sequence represented by SEQ ID NO: 1, or a naturally occurring allelic variant thereof,
   (b) is targeted to about nucleotides 112-152, 433-473, 546-586, 706-746, or 1015-1055 from the ATG start site of SEQ ID NO: 1 (starting at the "A"),
   (c) comprises at least one nucleotide analogue, and (c) is capable of reducing the level of C6 mRNA expression in a mammal, and
   wherein the oligomer is
   (d) single-stranded, or
   (e) a gapmer comprising 2 or 3 locked nucleic acid (LNA) monomers at each of the 3' and 5' ends of the oligomer.

4. The method of claim 3, wherein the method further comprises the step of measuring at least one of the MAC, the Complement Component 6 (C6) and mRNA encoding the Complement Component 6 following administration of the oligomer.

5. A method for treating, preventing or reducing symptoms of a disorder mediated by undesired activity of the complement system, the method comprising administering an antisense oligomer, wherein the oligomer is
   (a) between about 10 to 50 nucleotides in length having a contiguous nucleobase sequence with at least 80% sequence identity to a complementary region of a nucleic acid which encodes the COMPLEMENT COMPONENT 6 (C6) sequence represented by SEQ ID NO: 1, or a naturally occurring allelic variant thereof,
   (b) is targeted to about nucleotides 112-152, 433-473, 546-586, 706-746, or 1015-1055 from the ATG start site of SEQ ID NO: 1 (starting at the "A"),
   (c) comprises at least one nucleotide analogue, and (c) is capable of reducing the level of C6 mRNA expression in a mammal, and
   wherein the oligomer is
   (d) single-stranded, or
   (e) a gapmer comprising 2 or 3 locked nucleic acid (LNA) monomers at each of the 3' and 5' ends of the oligomer.

6. The method of claim 5, wherein the disorder is a chronic or acute demyelinating neuropathy.

7. The method of claim 6, wherein the disorder is multiple sclerosis (MS), Amyotrophic Lateral Sclerosis (ALS), or Huntington's Disease (HD).

8. The method of claim 7, wherein the method further comprises administering at least one of Rebif® (interferon beta-Ia, Avonex® (interferon beta-Ia), Betaseron® (interferon beta-Ib), Copaxone® (glatiramer acetate), Novantrone® (mitozantrone), and Tysabri® (natalizumab).

9. The method of claim 5, further comprising the administration of one or more of an anti-inflammatory agent and a complement inhibitor.

10. The method of claim 5, wherein the disorder is neuronal trauma or traumatic brain injury.

11. The method of claim 1 or 5, wherein the oligomer further comprises at least one of a modified internucleoside linkage and a modified nucleobase.

12. The method of claim 1 or 5, wherein the nucleotide analogue is a modified sugar moiety selected from the group consisting of: 2'-O-methoxyethyl modified sugar moiety, a 2'-methoxy modified sugar moiety, a 2'-O-alkyl modified sugar moiety, and a bicyclic sugar moiety.

13. The method claim 12, wherein the bicyclic sugar moiety is a locked nucleic acid (LNA) monomer.

14. The method of claim 1 or 5, wherein the oligomer further comprises 2'-deoxynucleotides positioned between the 5' and 3' wing segments and, optionally, one or both of the 5' and 3' ends of the oligomer.

15. The method of claim 11, wherein the modified internucleoside linkage is a phosphorothioate internucleoside linkage.

16. The method of claim 1 or 5, wherein the oligomer is 8, 9, 10, 11, 12, 13, 14, 15, 16, 17, 18, 19, or 20 nucleotides in length.

17. The method of claim 16, wherein the oligomer is between about 10 to about 18 nucleotides in length.

18. The method of claim 1 or 5, wherein the oligomer has at least 90%, 96%, 97%, 98% or 99% sequence identity to a complementary region of a nucleic acid which encodes the Complement Component C6 sequence represented by SEQ ID NO:1.

19. The method of claim of claim 18, wherein the oligomer comprises one, two, or three mismatches with respect to the Complement Component C6 sequence represented by SEQ ID NO: 1.

20. The method of claim 1 or 5, wherein the oligomer is targeted to about nucleotides 132, 453, 566, 726 or 1035 from the ATG start site of SEQ ID NO: 1.

* * * * *